United States Patent [19]

Lodzinski

[11] 4,288,160

[45] Sep. 8, 1981

[54] OPTICAL PROPERTY MEASUREMENT SYSTEM AND METHOD

[75] Inventor: Fred P. Lodzinski, Port Edwards, Wis.

[73] Assignee: Nekoosa Papers Inc., Port Edwards, Wis.

[21] Appl. No.: 543,902

[22] Filed: Jan. 24, 1975

Related U.S. Application Data

[63] Continuation-in-part of Ser. No. 429,637, Dec. 28, 1973, abandoned, and a continuation-in-part of Ser. No. 540,251, Jan. 10, 1975, Pat. No. 4,019,819.

[51] Int. Cl.³ .................... G01N 21/17; G01N 21/86
[52] U.S. Cl. ........................................ 356/73; 356/429
[58] Field of Search .................. 356/72, 73, 173, 176, 356/177, 178, 199, 200, 201, 209, 429; 250/559, 571; 235/151.3; 162/263

[56] References Cited

U.S. PATENT DOCUMENTS

| | | | |
|---|---|---|---|
| 3,228,282 | 1/1966 | Barker, Jr. | 356/199 |
| 3,405,268 | 10/1968 | Brunton | 356/73 |
| 3,827,808 | 8/1974 | Cho | 356/199 |

FOREIGN PATENT DOCUMENTS 323718  2/1972  U.S.S.R. .............................. 356/200

*Primary Examiner*—Vincent P. McGraw
*Attorney, Agent, or Firm*—Hill, Van Santen, Steadman, Chiara & Simpson

[57] ABSTRACT

In an illustrated embodiment, brightness, color, opacity and fluorescent contribution to brightness are measured by an on-line sensing head providing for simultaneous measurement of transmitted and reflected light. By measuring two independent optical parameters, paper optical properties of a partially translucent web are accurately characterized substantially independently of paper grade and weight. The instrument is designed so as to be capable of transverse scanning of a moving paper web on the paper machine, and so as to monitor desired paper optical characteristics with sufficient accuracy to enable on-line control of the optical characteristics of the paper being manufactured. Advantageously, several sets of reflectance and transmittance values based on respective common spectral response functions are sensed continuously and/or simultaneously during movement of the web.

4 Claims, 24 Drawing Figures

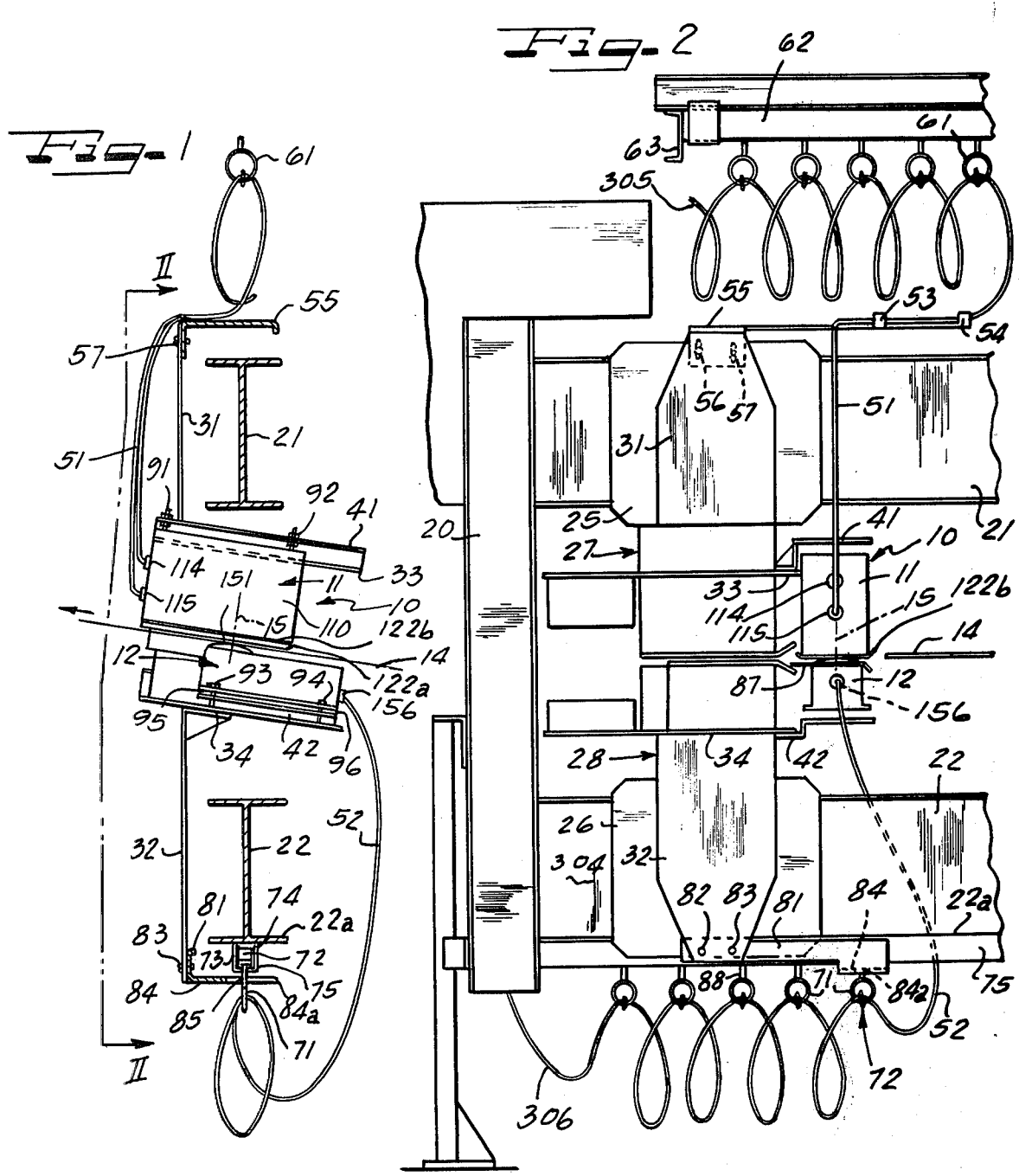

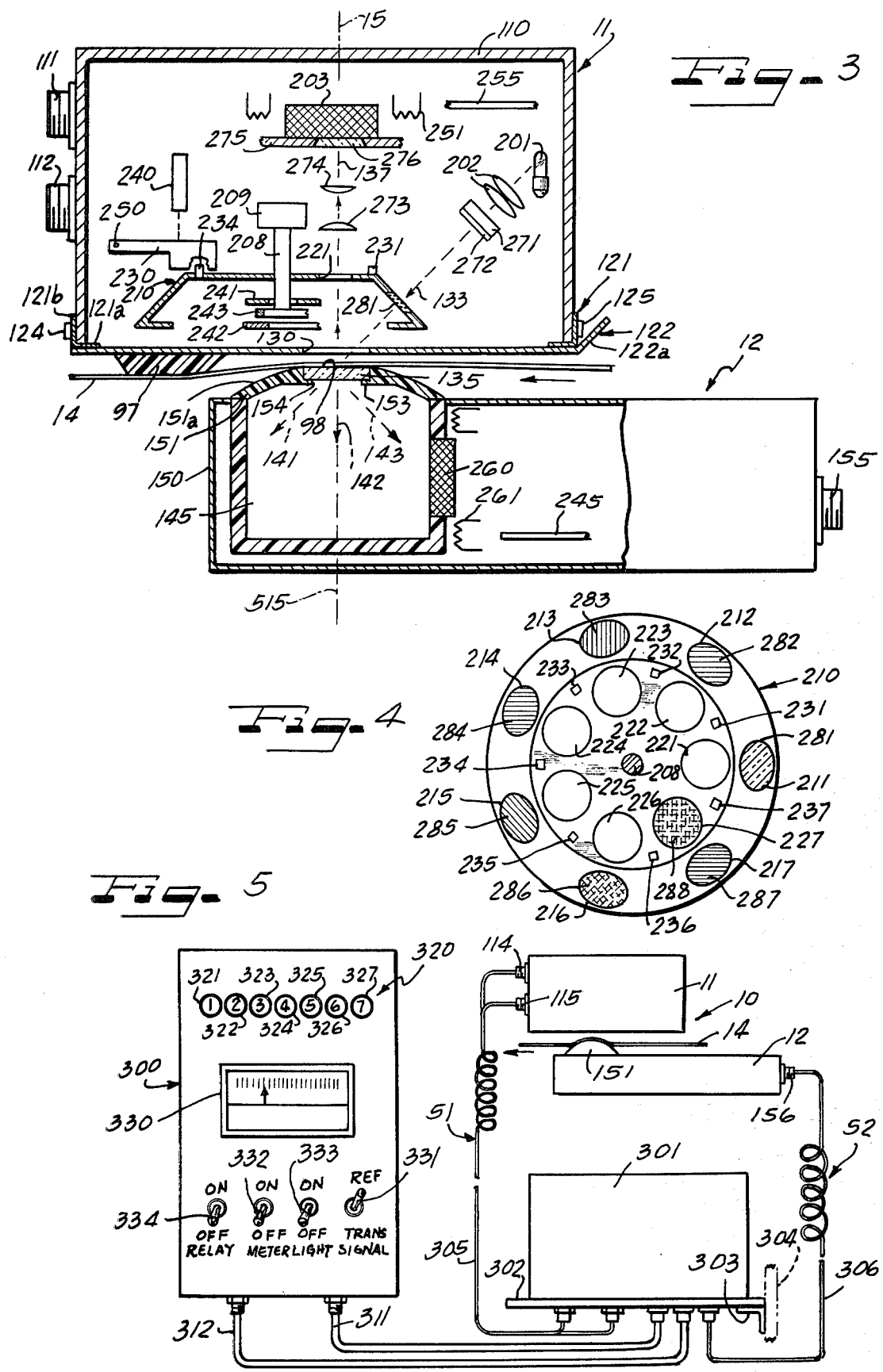

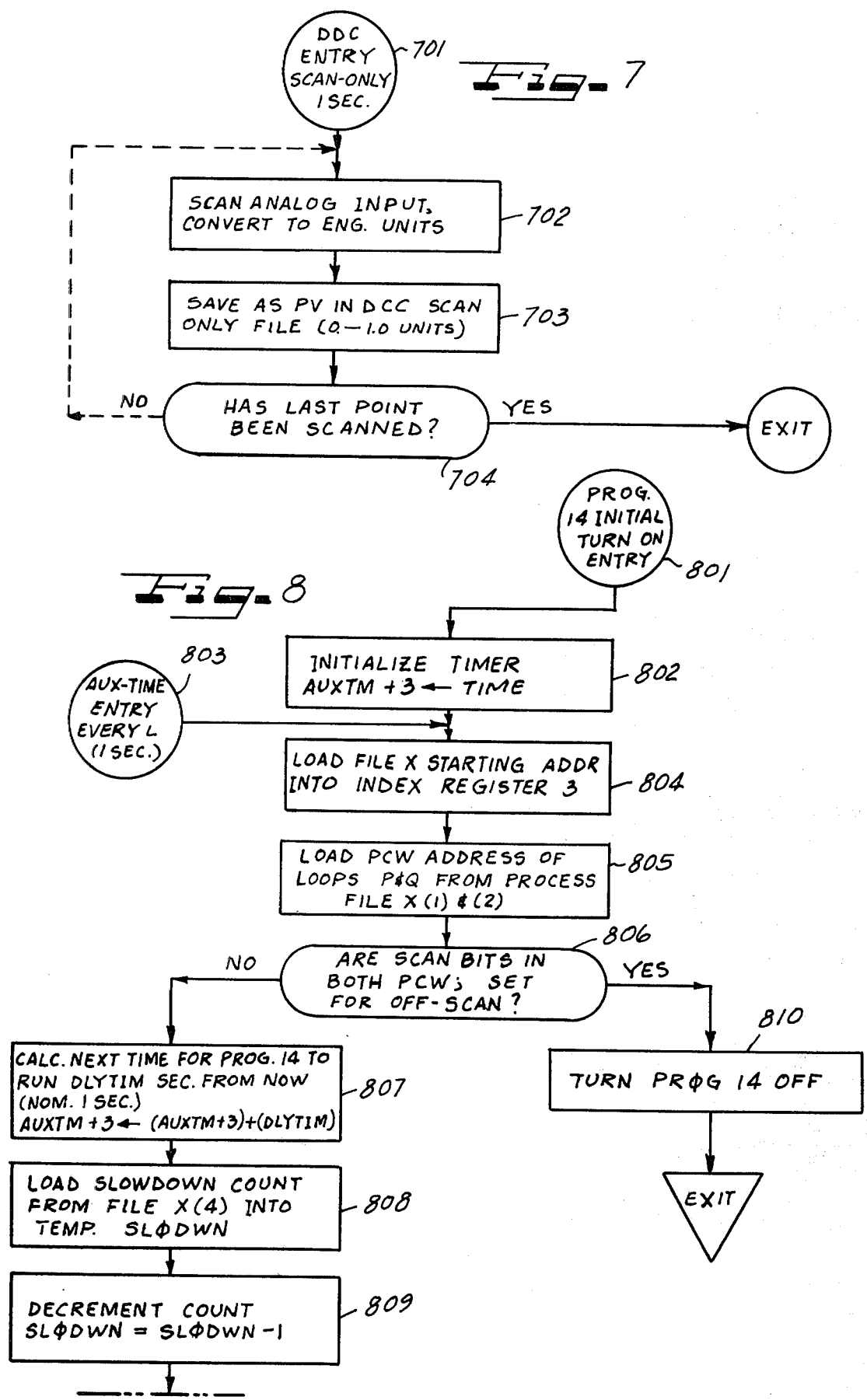

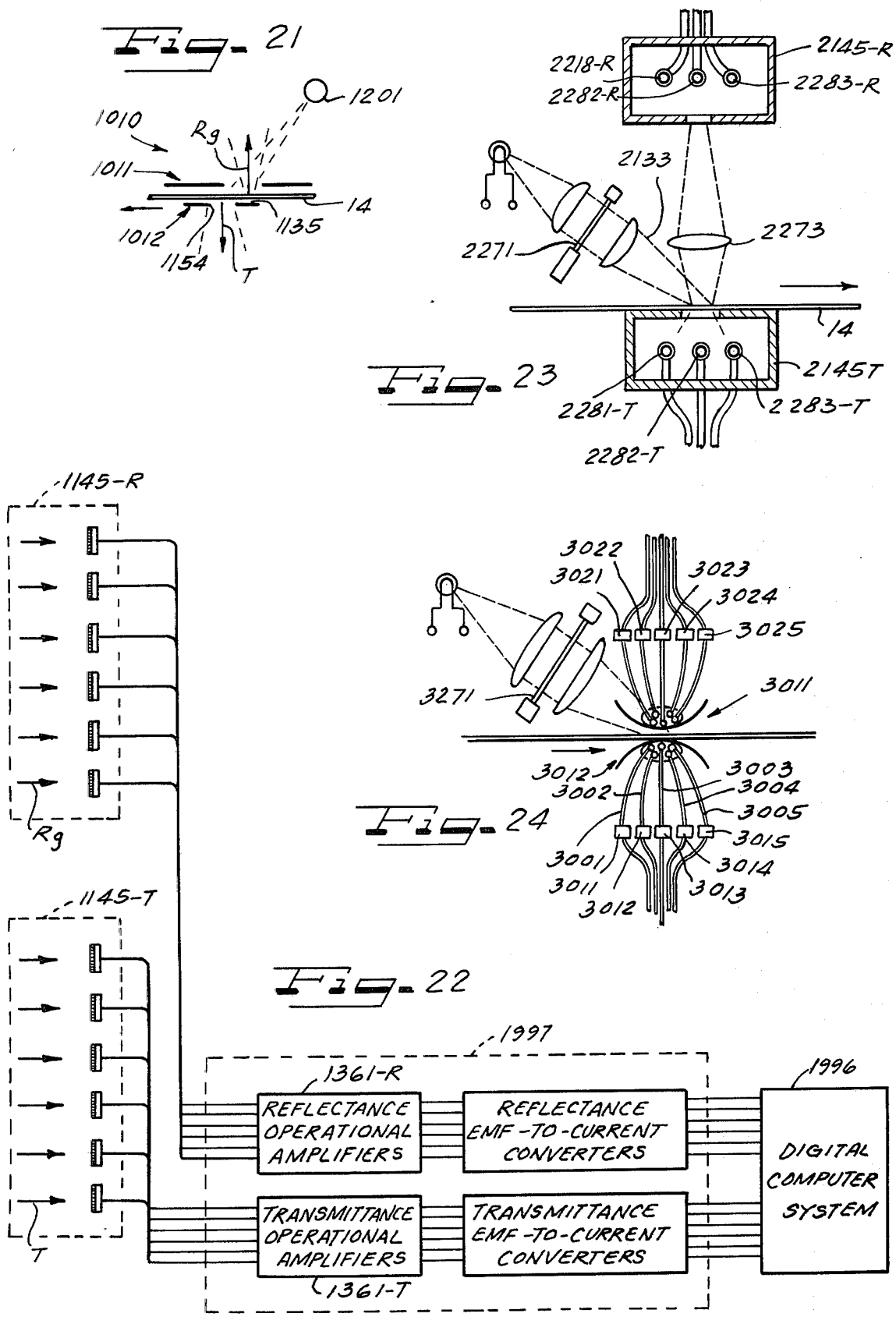

OPTICAL PROPERTY MEASUREMENT SYSTEM AND METHOD

CROSS-REFERENCES TO RELATED APPLICATIONS

The present application is a continuation-in-part of my copending application Ser. No. 429,637 filed Dec. 28, 1973 (now abandoned) and of my copending application Ser. No. 540,251 filed Jan. 10, 1975, now U.S. Pat. No. 4,019,819, and the written disclosure and drawings of each of these copending applications are incorporated herein by reference in their entireties.

BACKGROUND OF THE INVENTION

In the prior art it is known to obtain an indication of color and brightness characteristics of a paper web during manufacture by an on-line measurement of reflectance value (Rg), but this measurement is decidedly different from that necessary for actual color and brightness characterizations. Accordingly, such a measurement must be accompanied by very frequent off-line testing, so as to enable an adequate empirical calibration of the measuring instrument. Further, a separate set of calibration parameters is required for each grade and weight of paper. Off-line instruments which adequately measure these characteristics require that a pad of several thicknesses of paper be exposed to the light source aperture so that a different reflectance value (Roo) is obtained. Obviously this is impossible with an on-line instrument unless the far more inaccessible reel itself is tested.

Only where the on-line measured reflectance value (Rg) approaches the off-line value (Roo), as in instances of paper of extremely high opacity such as heavily coated or heavily dyed paper, can the above problems be minimized to the point where accuracy becomes sufficient for control purposes.

There is some possibility that the prior art includes the sequential measurement of two separate reflectance parameters such as one with a backing of near zero absolute reflectance and one with a white backing, but there appears to be no concept of a multiple property measurement system and method utilizing corresponding multiple sets of parameter measurements based on respective common spectral response functions and the prior art concept may be largely limited to a direct determination of Tappi opacity and/or to an abstract investigation of the feasibility of determining absolute reflectance (Roo) at a given wavelength such as 457 nanometers.

SUMMARY OF THE INVENTION

This invention relates to an optical device and method for sensing optical properties of a substantially homogeneous sheet material, and particularly to an on-the-paper-machine device and method for simultaneously sensing both transmitted and reflected light so as to obtain measurements from which the optical properties of interest can be calculated substantially independently of grade and weight of paper involved.

Accordingly it is an object of the present invention to provide an optical monitoring device and method for sensing optical properties based on measurements made on a single thickness of partially translucent substantially homogeneous sheet material and which measurements sufficiently characterize the actual properties of interest that a minimum of empirical calibration is required regardless of changes in grade and weight of paper.

Another object of the invention is to provide such an optical monitoring device and method capable of accurately sensing two or more optical properties such as brightness, color, opacity and/or fluorescent contribution to brightness preferably essentially continuously, or at least substantially simultaneously, and especially adapted for operation with a continuously moving web.

With such an optical monitoring device is useful off-line for sensing optical properties of a single thickness sample, it is a further important object of the present invention to provide such an optical monitoring device which is of sufficiently light weight and compact construction so as to be adapted for on-line monitoring of the desired optical properties.

Another and further object of the invention is to provide an on-the-paper-machine optical monitoring device of sufficient flexability and accuracy to enable control of desired optical properties during the paper making process.

A unique feature of the on-line optical monitoring device is its ability to essentially simultaneously measure both reflected and transmitted light. By measuring two independent optical parameters it is possible to thoroughly characterize the paper optical properties of a partially translucent web with a minimum of empirical correction for factors such as paper grade and weight. Preferably a plurality of sets of optical parameters are sensed continuously or at least substantially simultaneously.

Other objects, features and advantages of the present invention will become apparent from the following detailed description taken in connection with the accompanying drawings.

BRIEF DESCRIPTION OF THE DRAWINGS

FIG. 1 is a fragmentary somewhat diagrammatic longitudinal sectional view of a paper machine showing in outline a side view of an optical monitoring device in accordance with the present invention operatively mounted on line with the machine;

FIG. 2 is a fragmentary somewhat diagrammatic transverse sectional view of the paper machine of FIG. 1 and taken generally as indicated by the line II—II of FIG. 1 and looking in the direction of the arrows (toward the wet end of the paper machine), the view being taken so as to show in outline a direct front view of the optical monitoring device of FIG. 1;

FIG. 3 is a diagrammatic longitudinal sectional view of one embodiment of an on-the-paper-machine optical monitoring device in accordance with the present invention;

FIG. 4 is a partial diagrammatic plan view of the filter wheel assembly utilized in the monitoring device of FIG. 3;

FIG. 5 is a somewhat diagrammatic view illustrating an optical analyzer unit in electrical association with the optical monitoring device of FIGS. 1-4 and with a power supply unit;

FIG. 7 is a flow chart illustrating an existing direct digital control analog point scan program which has been adapted to allow for the collection and temporary storage of the reflectance and transmittance data acquired from the system of FIGS. 1–6;

FIGS. 8–16 when arranged in a vertical series represent a program fourteen which is designed to read the reflectance and transmittance values stored pursuant to FIG. 7 and generally to control the operation of the system of FIGS. 1–6 and to apply correction factors to the raw reflectance and transmittance data;

FIG. 21 is a diagrammatic view illustrating the embodiment described in the section entitled "Proposed Instrument Design" of the aforementioned copending applications;

FIG. 22 illustrates further details of the embodiment of FIG. 21 as described in the copending applications;

FIG. 23 shows an embodiment similar to that of FIGS. 21 and 22, but with the interior of the transmittance cavity providing the backing for the reflectance measurements; and FIG. 24 shows an embodiment similar to that of FIGS. 21 and 22, but utilizing multiple sets of reflectance and transmittance optical light pipes.

DESCRIPTION OF THE PREFERRED EMBODIMENTS

Figure 6:
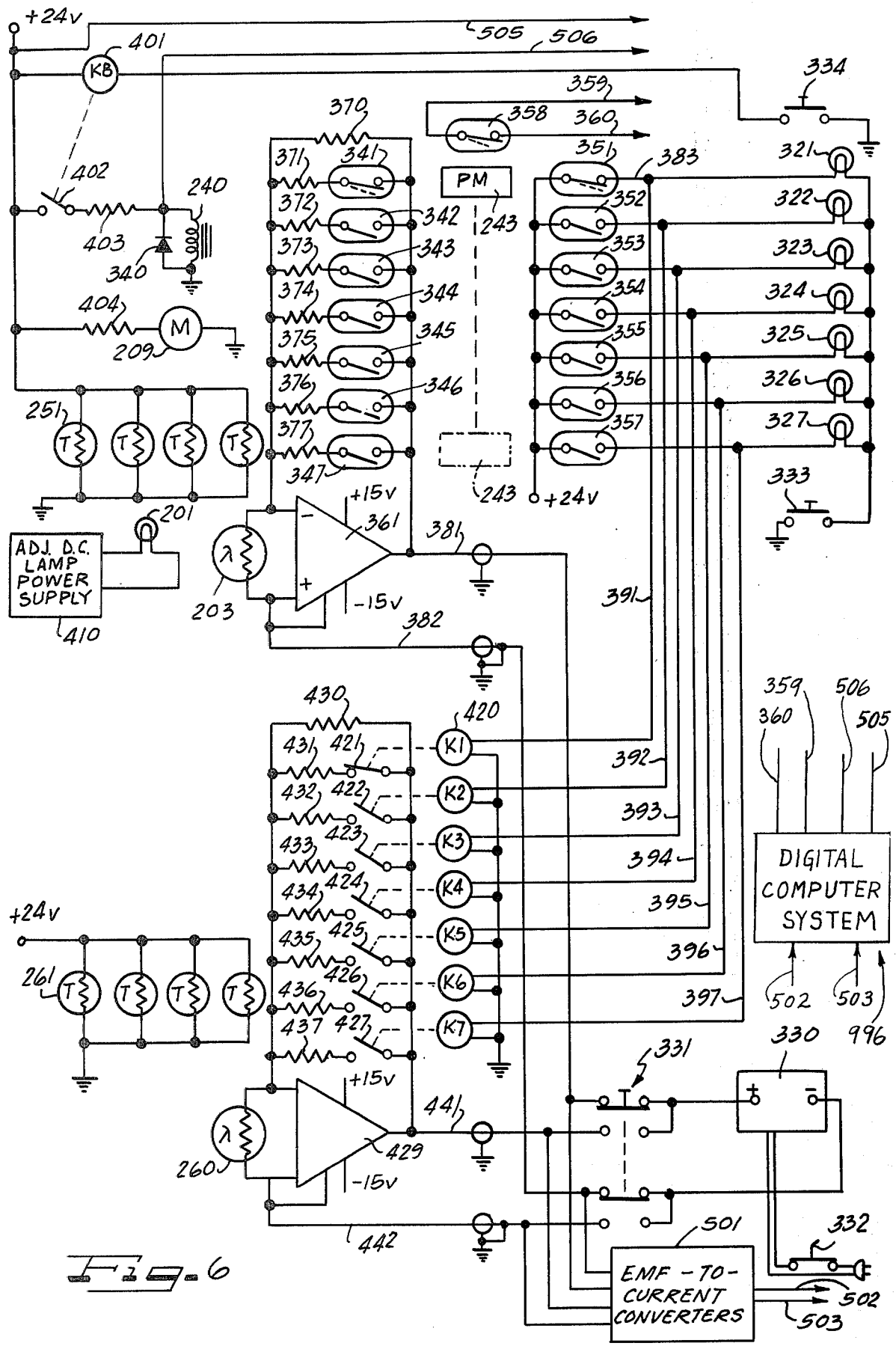
FIG. 6 is an electric circuit diagram illustrating the electrical connections between the various components of FIGS. 1-5.

Detailed Description Of The Apparatus of FIGS. 1 and 2

FIGS. 1 and 2 will serve to illustrate the modifications of an existing paper machine which are required for carrying out a preferred embodiment of the present invention. Referring to FIGS. 1 and 2, an on-the-paper-machine optical monitoring device is diagrammatically indicated at 10 and comprises an upper sensing head 11 and a lower sensing head 12 which are maintained in precise relative alignment and disposed for operative association and transverse scanning movement relative to a paper web located as indicated at 14 in FIGS. 1 and 2. As will be described hereinafter with reference to FIGS. 3 and 4, in a particular design of the optical monitoring device, upper head 11 includes a light source for projecting light onto the web such that a portion of the light is reflected parallel to an optical axis indicated at 15, while a further portion of the light is transmitted through the paper web for collection and measurement by means of the lower sensing head 12.

For purposes of illustration, FIGS. 1 and 2 show portions of an existing web scanner construction which is utilized to scan the web 14 for conventional purposes. The conventional scanner construction includes fixed frame components such as 20, 21 and 22 forming what is known as an "O" type scanner frame. The conventional scanning structure further includes upper and lower slides 25 and 26 for joint horizontal movement along the horizontal beams 21 and 22. Associated with the slides 25 and 26 are movable assemblies 27 and 28 carried by the respective slides 25 and 26 and including vertically disposed plates 31 and 32 and angularly disposed flange members such as indicated at 33 and 34 in FIG. 1. These flange portions 33 and 34 have broad surfaces lying in planes generally parallel to the plane of the web 14 and are utilized for mounting of the monitoring device 10 of the present invention. In particular a top head mounting bracket is indicated at 41 in FIGS. 1 and 2 and is shown as being secured to the existing flange part 33 so as to mount the upper head 11 for scanning movement with the assembly 27. Similarly a lower head mounting bracket is indicated at 42 and is shown as being secured to flange part 34 of the lower movable assembly 28 so as to mount the lower sensing head 12 for scanning movement jointly with the upper sensing head 11.

For the purpose of electrical connection with the monitoring device 10 during its traverse of the web 14, electric cables are indicated at 51 and 52 for electrical connection with the components of the upper sensing head 11 and lower sensing head 12 of the monitoring device 10. The cable 51 is shown as being fastened by means of straps 53 and 54 to a top carrier slide bracket 55. The bracket is shown as being secured by means of fasteners 56 and 57 to the upper portion of vertical plate 31. As indicated in FIG. 2, successive loops of cable 51 are secured to swivel type ball bearing carriers such as indicated at 61. A trolley track 62 is supported from existing channels such as indicated at 63 and mounts the carriers 61 for horizontal movement as required to accommodate the scanning movement of the monitoring device 10 across the width of the web 14. Similarly, successive loops of the cable 52 are fastened to the eyes such as indicated at 71 of a lower series of carriers 72. As seen in FIG. 1 each of the carriers such as 72 includes a pair of rollers such as 73 and 74 riding in the trolley track 75 which is secured directly to the lower flange 22a of beam 22. A lower carrier slide bracket 81 is secured to vertical plate 32 by means of fasteners 82 and 83 and is provided with a horizontally extending flange 84 for engaging with the first of the series of lower carriers 72. In particular, carrier 72 is provided with a shank 85 which extends into a longitudinal slot 84a of flange 84. Thus, the first carrier 72 is interengaged with the bracket 81 and is caused to move with the lower assembly 28 and the lower sensing head 12. The remaining lower carriers such as that indicated at 83 move along the trolley track 75 as necessary to accommodate movement of the monitoring device 10 transversely of the web 14.

While FIGS. 1 and 2 have illustated the optical monitoring device of the present invention as being mounted on line with the paper machine and have further illustrated the case where the monitoring device is to be scanned transversely of the web, it is considered that the optical monitoring device of the present invention would also be of great value if redesigned for bench mounting. By placing a single sheet of paper in a sample mount of the device, a technician could simultaneously test the sample for color, brightness, fluorescence, and opacity in a matter of seconds.

In the illustrated embodiment, however, it is contemplated that the monitoring device 10 will be mounted on line with the paper machine and will be capable of movement to a position clear of the edge of the web as indicated in FIG. 2 at the end of each hour of operation, for example. When the end of a production run for a given web 14 has been reached, or when a web break occurs for any reason (such as accidental severance of the given web), the monitoring device 10 will be moved clear of the edge of the web path as indicated in FIG. 2. Each time the monitoring device 10 is moved to the off-web position shown in FIG. 2 it is preferred that readings be taken of the reflectance and transmittance values (without the web in the optical path) for the purpose of obtaining an updated calibration of the monitoring device. Thus, such updating of calibration may take place automatically (for example under the control of a process control computer controlling the paper manufacturing operation) at hourly intervals and also after web breaks. The monitoring device can, of course, be retracted manually any time desired by the operator for the purpose of checking calibration. By way of example, the monitoring device 10 may be capable of a normal scanning travel over a distance of 115 inches with provision for an additional travel of 16 inches to the position shown in FIG. 2. A flange is indicated at 87 which serves to insure proper re-engagement of the sensing head with the web at the operator's side of the illustrated paper machine (opposite the side indicated in FIG. 2).

The lower head 12 is designed to contact the web 14 during scanning thereof. The design spacing between the upper and lower heads 11 and 12 is 3/16 inch. The optical opening in the upper head 11 is aligned with the optical axis 15 and is to be maintained in alignment with the center of the window in the lower head 12. Four adjusting screws such as those indicated at 91 and 92 are provided for accurate positioning of the upper head 11. Similarly four position adjusting screws such as 93 and 94 serve for the accurate positioning of the lower head in conjunction with set screws such as indicated at 95 and 96. The adjusting screws are located at each corner of mounting brackets 41 and 42.

Modifications of FIGS. 1 and 2 To Insure Accurate Scanning

Where the web is not perfectly horizontal, but instead is curved across its width, it is desirable to provide a web deflecting guide bar as indicated at 97 in FIG. 3 for insuring stable contact between the web 14 and the web engaging surface 98 of the lower sensing head 12. By way of example the guide bar may protrude from the lower surface of the upper sensing head a distance of 5/16 inch so as to overlap with respect to the vertical direction a distance of ⅛ inch relative to the lower sensing head web contacting surface 98. The guide bar 97 may have a width to force down at least about four inches of the width of the web at a section of web centered with respect to web engaging surface 98 of the lower sensing head relative to the machine direction. This insures a minimum of a ⅛ inch bellying of the sheet as it travels over the lower sensing head in all lateral positions of the sensing head.

In order to minimize changes in the 5/16 inch thickness dimension of the guide bar 97 due to wear, the guide bar is provided with a flat web engaging surface 97a which has a dimension in the direction of web movement of about one inch. By way of example, the guide bar may be made of Teflon.

Since the guide bar 97 is not necessary when the web is fed from the calender stack to the reel in a relatively planar configuration, it has not been shown in FIGS. 1 and 2.

Various modifications may of course be made to adapt the monitoring device of the present invention to various types of paper machinery, and to secure any desired degree of accuracy in the joint scanning movement of the upper and lower sensing heads relative to the paper.

Structure Of The Optical Monitoring Device As Shown in FIGS. 3 and 4

Referring to FIG. 3, the upper sensing head 11 is shown as comprising a casing 110 having suitable connectors 111 and 112 for receiving suitable internally threaded fittings 114 and 115, FIG. 1 associated with the electric cable 51. The casing 110 receives a top head shoe 120 including an interior open rectangular frame 121 having a base flange 12a spot welded to shoe plate 122. The upstanding portion 121b engages the adjacent wall of casing 110 along all four sides thereof and is secured to the casing 110 by suitable fastening means such as indicated at 124 and 125 in FIG. 3. An edge 122a of shoe plate 122 is bent up at an angle of 45° at the side of the sensing head 11 facing the wet end of the paper machine, and a similar inclined edge 122b, FIG. 1, is provided at each of the sides of the sensing head so as to present smooth faces to the paper web during scanning movement of the sensing head. The shoe plate 122 is provided with a circular aperture of less than one inch diameter as indicated at 130 centered on the optical axis 15 of the device. In a present embodiment aperture 130 has a diameter of about ⅞ inch. This aperture 130 is preferably of minimum diameter necessary to accommodate the light paths of the instrument. In the illustrated embodiment the light path for the incident light beam as indicated at 133 is directed at an angle of approximately 45° and is focused to impinge on a window 135 at the optical axis 15. A reflected light path as indicated at 137 is normal to the web engaging surface 98 (which is the upper surface of window 135), and is coincident with the optical axis 15, while light transmitted through the web 14 and through the window 135 is directed as indicated by rays 141–143, for example, into an integrating cavity 145 of lower head 12.

The lower head 12 comprises a casing 150 having an annular dished plate 151 secured thereto and providing a generally segmental spherical web-contacting surface 151a surrounding window 135. The window 135 is preferably formed by a circular disk of translucent diffusing material. In the illustrated embodiment the window 135 is made of a polycrystalline ceramic material available under the trademark "Lucalux" from the General Electric Company. This material has physical properties similar to that of sapphire. The opposite faces of window 135 are flat and parallel and the thickness dimension is 1/16 inch. A lip is indicated at 153 for underlying an annular edge portion of window 135. This lip provides a circular aperture 154 having a diameter of about 15/16 inch so that the effective viewing area for the transmitted light is determined by the diameter of aperture 154. The casing 150 is shown as being provided with an electrical connector terminal 155 for receiving a suitable internally threaded fitting 156, FIG. 1, of cable 52.

As diagrammatically indicated in FIGS. 3 and 4, the upper sensing head 11 includes a light source 201, incident optical path means including lenses such as indicated at 202 and a photocell 203 for measuring reflected light returning along the reflected light path 137. A filter wheel 210 is shown diagrammatically as being mounted on a shaft 208 for rotation by means of a low torque motor indicated at 209. As best seen in FIG. 4, the filter wheel includes an outer series of apertures 211–217 for selective registry with the incident light beam path 133, and includes a series of inner apertures 221–227 for selective registry with the reflective light beam path 137. The various apertures may receive suitable filter elements as will hereinafter be explained in detail such that a series of measurements may be taken by successively indexing the filter wheel 210 to successive operating positions. In each operating position one aperture such as 211 is in alignment with the incident beam path 133 and a second aperture such as indicated at 221 is in alignment with the reflected light beam path 137.

By way of example, the motor 209 may be continuously energized during operation of the monitoring device, and the filter wheel may be retained in a selected angular position by engagement of a ratchet arm 230 with one of a series of cooperating lugs 231-237 arranged generally as indicated in FIG. 4 on the filter wheel 210. A solenoid is indicated at 240 as being mechanically coupled with ratchet arm 230 for momentarily lifting the ratchet arm 230 out of engagement with a cooperating lug such as 231 so as to permit the filter wheel to index one position. Immediately upon release of the energization of solenoid 240, the force of gravity returns the ratchet arm 230 to the position shown in FIG. 3 so as to be disposed in the path of the lugs and thus to engage the next lug in succession such as lug 232 as the motor 209 moves the filter wheel 210 into the next operating position.

As will hereafter be explained in greater detail, reed switches are mounted in circles on respective switching boards 241 and 242, FIG. 3, and the filter wheel shaft 208 carries a magnet 243 for actuating a respective pair of the reed switches in each operating position of the filter wheel 210. Thus the position of the filter wheel 210 determines which of the switches on the switching boards 241 and 242 are closed. As will be explained hereinafter, the reed switch on the upper switching board 241 which is closed determines the gain setting of an upper head amplifier at a level appropriate for the set of filters which are in the operating position. The reed switch on the lower switching board 242 which is closed activates a relay on a circuit board 245 in the lower head 12, and such relay in turn sets the lower head amplifier gain at the proper level. As will be explained in connection with the electric circuit diagram for the monitoring device, certain conductors of the cable 51 may be interconnected at a remote location so as to cause an indexing movement of the filter wheel 210. This external command serves to momentarily energize solenoid 240 and lift the ratchet arm 230 about is pivot point 250, allowing the motor 209 to rotate the filter wheel 210. The ratchet arm 230 returns to the position shown in FIG. 3 to catch the next lug on the filter wheel stalling the motor 209.

Four heaters such as indicated at 251 are mounted around photocell 204 so as to minimize the temperature variations of the photocell. A circuit board for mounting an amplifier for photocell 203 and for mounting the gain setting resistances associated with the reed switches is indicated at 255 in FIG. 3.

Referring to the lower head 12, FIG. 3 indicates a photocell 260 for receiving light from the intergrating cavity 145 and a series of heaters such as 261 mounted around the photocell 260 to minimize the temperature variations of the photocell. Circuit board 245 may mount a suitable amplifier for photocell 260, the gain of which being controlled by the relays previously mentioned.

The heaters 251 and 261 in the prototype unit were Pennsylvania Electronics Technology Type 12T55. (These are positive temperature coefficient thermistors with 55° C. switching temperatures.) These heaters will tend to stabilize the temperature since their ability to provide heat decreases as the ambient temperature increases. Above 55° C., they provide essentially no heat at all.

Discussion of Illustrative Operating Details for the Monitoring Device of FIGS. 3 and 4

A basic feature of the illustrated embodiment resides in its ability to measure simultaneously both reflected and transmitted light. While in the illustrated embodiment, the reflected light path 137 and the transmitted light path intersect the web 14 essentially at a common point, reflected light could be obtained from a point on the sample or web offset from the point where light is transmitted through the sample. For example, a backing of some specified reflectance such as a black body of zero or near zero reflectance could be located on the lower sensing head just ahead of or behind the transmitted light receptor compartment (with respect to the machine direction of the sample or the direction of movement of the web). In this case the upper sensing head could contain the light source as well as a reflected light receptor for receiving light reflected from the sample or moving web at a point directly above the backing of specified reflectance. Both the reflected light receptor in the upper sensing head and the transmitted light receptor in the lower sensing head could then supply signals simultaneously and continuously during measurement operations. Many other variations in the arrangement of the optics for measuring both reflected and transmitted light will occur to those skilled in the art.

Referring to the details of the illustrated embodiment, however, and to the case where it is desired to measure brightness, color, opacity and fluorescent contribution to brightness, light source 201, FIG. 3, may consist of a Model 1962 Quartzline lamp operated at 5.8 volts as measured at the lamp terminals. The 45° incident beam path 133 and the normal reflected beam path 137 correspond to those of a standard brightness testor, and a casting (not shown) from a bench type standard brightness tester was used in constructing a prototype of the illustrated embodiment to give rigid support for the optical components such as indicated at 202 and 271-276 in FIG. 3. In the specific prototype unit, a stock thickness polished Corning type 4-69 glass filter 271 and a second type 4-69 filter 272 ground and polished to an appropriate thickness were used in the incident beam path to absorb most of the infrared as well as to give proper spectral response.

The reflected light path 137 included a pair of lenses 273 and 274 which focus the light on a ⅜-inch aperture in the plate 275 of the casting. A piece of diffusing glass 276 is located on the ⅜-inch aperture so that the light distribution over the surface of photocell 203 will be reasonably uniform. A Weston model 856 RR Photronic cell was employed.

The filter wheel 210 is designed and located in such a way that either the incident or the reflected beam or both can be filtered as desired. In the prototype, the wheel 210 was driven by a small motor 209 operated at reduced voltage so that it could operate continuously in a stalled condition.

Commerically available color and brightness meters are usually manufactured with the spectral response filters located in the reflected beam. In the prototype device, and in the later on-machine version here illustrated as well, however, the filters which determine the spectral response of the first six filter positions are located in the incident beam. There are two basic reasons for this choice of design.
  (1) Both the reflected and transmitted light have the same incident intensity and spectral response against which each can be compared. The alternate would necessitate two sets of identical filters, one set located in the reflected beam and another in the transmitted beam—a difficult design to achieve in practice.
  (2) Filters in the incident beam can be used to absorb all ultraviolet light and prevent it from striking the specimen. Thus, fluorescence, a phenomenon not accounted for by Kubelka-Munk theory is avoided.

For reasons explained shortly, the seventh filter position is an exception to the above in that substantial ultraviolet light is intentionally permitted to exist within the incident beam. Outside of the phenomenon of fluorescence the spectral response is independent of whether such filters are located in the incident or the reflected beams.

The spectral response provided by the respective positions of the filter wheel 210 were as follows: (1) papermaker's brightness (TAPPI brightness), (2) blue portion of the $E_c\bar{x}$ function, (3) red portion of the $E_c\bar{x}$ function, (4) $E_c\bar{z}$ function without fluorescence (5) $E_c\bar{y}$ function, (6) $E_a\bar{y}$ function, and (7) $E_c\bar{z}$ function, with fluorescence.

As is understood in the art, the symbols $E_c\bar{x}$, $E_c\bar{y}$, $E_a\bar{y}$, and $E_c\bar{z}$ refer to tristimulus functions of wavelength as defined by the Commission Internationale c l'Éclairage which is identified by the abbreviation C.I.E. and is also known as the International Committee on Illumination. The subscript a in the function designation $E_a\bar{y}$ indicates that the function is based on a standardized illumination designated as C.I.E. Illuminant A, while the subscript c in the other function designations refers to a somewhat different standardized illumination which is designated as C.I.E. Illuminant C.

Filters for providing the above spectral response characteristics in the respective operating positions of the filter wheel 210 have been indicated in FIG. 4 by reference numeral 281-288. In the specific example under discussion, apertures 221-226 are left open. Filter 281 is a standard filter for use in measuring TAPPI brightness, TAPPI referring to the Technical Association of the Pulp and Paper Industry. This filter transmits a narrow band of wavelengths in the vicinity of 457 nanometers.

Filters 282-285 are standard filters for a four-filter colorimeter and are conventionally designated X (blue), X (red), Z, and $Y_C$. These filters provide the wavelength distributions required for the measurement of the C.I.E. X, Y, and Z tristimulus values under Illuminant C.

Filter 286 is conventionally designated as a $Y_A$ filter and is required by the TAPPI standard method for opacity measurements. This is a board band filter producing the C.I.E. Y wavelength distribution for Illuminant A, in conjunction with the source 201 previously described in this section. A discussion bearing on the feasibility of this type of measurement is found in a paper by L. R. Dearth, et al entitled "Study of Instruments for the Measurement of Opacity of Paper, V. Comparison of Printing Opacity Determined with Several Selected Instruments", *Tappi*, volume 53, No. 3 (March, 1970).

With respect to position No. 7 of the filter wheel 210, filters 287 and 288 are conventionally designated as Z (blue) and Z (yellow). As previously indicated, the purpose of the filters is to provide for a determination of the C.I.E. Z tristimulus value with the fluorescence component included. In filter position No. 4, filter 284 serves to remove the ultraviolet component from the incident beam so that a measure of the Z tristimulus value without fluorescence is obtained. In position No. 7 of the filter wheel, however, filter 287 in the incident beam is designed to transmit the ultraviolet component, so that the fluorescent component if any will be transmitted to photocell 203. The ultraviolet absorbing component of the Z type filter means is located in the reflected beam 137, whereas this component is in the incident beam for the No. 4 position. The fluorescent component is lineally related to the difference between the Z tristimulus values determined in the No. 4 and No. 7 positions of the filter wheel 210.

Filters 281-288 have been shown in FIG. 4 with different types of hatching which have been selected to represent generally the different light transmission properties of the filters. In particular, the hatching for filters 281-288 are those for representing white, blue, red, blue, green, orange, blue and yellow light transmission properties. The selection of hatching is primarily for purposes of graphical illustration and is not, of course, an exact representation of the light transmission properties of the respective filters.

Detailed Description of FIGS. 5 and 6

FIG. 5 illustrates diagrammatically the optical monitoring device 10 of FIGS. 1-4, and illustrates by way of example an optical analyzer unit 300 which may be electrically associated with the monitoring device and serve as an operator's console to be disposed at a convenient location adjacent the paper machine. By way of example, the optical analyzer unit may be mounted near the dry end of the paper machine, and may receive conventional alternating current power from the paper machine dry end panel. The optical analyzer unit 300 is illustrated as being coupled with the monitoring device 10 via a power supply unit 301 which is mounted adjacent the vertical column 20, FIG. 2, of the "O" frame along which the monitoring device is to travel in scanning the width of the web. For purposes of diagrammatic illustration, power supply unit 301 is shown as being provided with a mounting plate 302 which is secured by means of a bracket 303 to an end of horizontal beam 22 which has been specifically designated by reference numeral 304 in FIGS. 2 and 5. Referring to FIG. 2, it will be observed that the ends 305 and 306 of cables 51 and 52 are adjacent the end 304 of beam 22 so that this is a convenient location for mounting of the power supply 301. The electrical interconnections between the power supply unit 301 and the optical analyzer unit 300 are indicated as extending via a signal conduit 311 and a control conduit 312. By way of example, the signal conduit 311 may contain shielded electric cables for transmitting millivolt signals from the analogue amplifiers of the upper and lower sensing heads 11 and 12. The control conduit 312 may contain conductors which are respectively energized to represent the angular position of filter wheel 210, and may also contain a conductor for controlling the indexing movement of the filter wheel as will be explained in detail in connection with FIG. 6.

Referring to the optical analyzer unit 300 of FIG. 5, the front panel of the unit has been diagrammatically indicated at 320 as being provided with a series of lamps 321-327 for indicating the angular position of the filter wheel 210 within the upper sensing head 11. The lamps 321-327 have been numbered 1 through 7 in correspondence with the seven positions of the filter wheel, and the color of the lamps, for example, may be selected so as to signify the characteristics of the filters located in the openings of the filter wheel such as those indicated at 211-217.

In order to provide a visual indication of the amplitude of the millivolt signals supplied from the sensing heads 11 and 12, a suitable meter is indicated at 330 and a selector switch is indicated at 331 for selectively supplying to the meter the analogue signal from the upper sensing head 11 or from the lower sensing head 12. A switch 332 is indicated for controlling the supply of conventional alternating current power to the meter, and a second switch 333 is indicated for controlling the supply of energizing power for the lamps 321-327. Another switch 334 may be momentarily actuated so as to index the filter wheel 210 to a desired station. The switches 331-334 may, of course, take any desired form, and have merely been indicated diagrammatically in FIG. 5.

Referring to FIG. 6, various of the components previously referred to have been indicated by electrical symbols, and for convenience of correlation of FIG. 6 with FIGS. 1 through 5, the same reference characters have been utilized. In particular, FIG. 6 shows symbolically a light source 201, associated photocells, 203 and 260, filter wheel drive motor 209, control solenoid 240, and permanent magnet 243 which rotates with the filter wheel 210 so as to represent the angular position of the filter wheel. Also shown in FIG. 6, are the four heaters 251 associated with photocell 203, and the four heaters 261 associated with the photocell 260. Further, lamps 321-327, millivoltmeter 330 and switches 331-334 of the optical analyzer unit 300 have been symbolically indicated in FIG. 6.

Referring first to the components associated with the upper sensing head 11, there is illustrated in the upper left part of FIG. 6 a diode 340 connected across solenoid 240. For diagrammatic purposes, permanent magnet 243 is shown arranged between two series of reed switches 341-347 and 351-357. A further reed switch 358 is indicated for actuation in the number 1 position of the filter wheel 210 along with switches 341 and 351. The conductors 359 and 360 associated with switch 358 may be connected with the optical analyzer unit 300, and may be connected via the optical analyzer unit 300 with a remote computer, where the illustrated apparatus forms part of a computer control system for controlling the associated paper machinery.

The reed switches 341-347 are shown as being associated with an operational amplifier 361, so that switches 341-347 serve to select the desired value of feed back resistance for the amplifier in each position of the filter wheel 210. Thus, switches 341-347 served to selectively connect in parallel with resistance 370, additional resistance values 371-377, respectively, for adjusting the total resistance between the input and output terminals of the amplifier 361. Thus, in the number 1 position of the filter wheel, permanent magnet 243 is in a position to actuate switch 341, and connect resistance value 371 in parallel with resistor 370. As will hereinafter be explained, resistance means 371-377 may include variable resistors for adjustment so as to provide the desired gain of amplifier 361 in the respective filter positions, or fixed resistance values may be inserted as indicated, once the desired values have been determined for a given filter wheel. As indicated in FIG. 6, the output of amplifier 361 may be transmitted by means of shielded cables 381 and 382. These cables form part of the overall cable indicated at 51 in FIG. 5 leading from the upper sensing head 11 to the power supply unit 301.

Also forming part of the cable 51 would be the conductors such as indicated at 383 from the respective reed switches 351-357. These conductors such as 383 would connect with respective conductors 391-397 of cable 52 leading from the power supply 301 to the lower sensing head 12.

Included as part of the power supply unit 301 would be components such as relay actuating coil 401, associated normally open contact 402, and resistors 403 and 404 shown at the upper left in FIG. 6. Further, the power supply would include an adjustable direct current lamp power supply component 410 for supplying a precisely adjusted or controlled electrical energization for light source 201. Further, of course, the power supply would supply the required direct current operating potentials for the upper sensing head as indicated in FIG. 6.

The lower left section of FIG. 6 illustrates the electrical components of the lower sensing head 12. In the lower sensing head, conductors 391-397 control energization of the operating coils of respective relays K1 through K7. With the permanent magnet 243 in the number 1 position, reed switch 351 is closed, and operating coil 420 of relay K1 is energized closing the associated relay contact 421. The remaining relays K2 through K7 are deenergized, so that the respective associated contacts 422-427 remain open. The contacts 421-427 serve to control the resistance in the feed back path of operational amplifier 429 in conjunction with resistor 430 and resistance means 431-437. As explained in reference to the upper sensing head, resistance means 431-437 may include adjustable resistors, or fixed resistors as shown selected to provide the desired gain of amplifier 429 for the respective positions of the filter wheel 210. The shielded cables 441 and 442 from the output of amplifier 429 connect with power supply unit 301 as part of cable 52. The outputs from the amplifiers 361 and 429 are conducted from the power supply unit 301 to the optical analyzer unit 300 via signal conduit 311, and within the optical analyzer unit connect with respective terminals of the selector switch 331 as indicated at the lower part of FIG. 6. Thus, in the upper position of the selector 331, the output of amplifier 361 is connected with the meter 330, while in the lower position of selector 331, the output of amplifier 429 is supplied to the meter 330. Of course, the optical analyzer 300 may further include analogue to digital converters for converting the outputs of the amplifiers 361 and 429 to digital form for transmission to a remote computer, for example. It will be apparent to those skilled in the art that the remote computer could be programmed to control the sequential actuation of relay 401 during each increment of scanning movement of the monitoring device 10 so as to obtain readings from each desired sampling region of the web 14 for each of the seven positions of the filter wheel 210. The remote computer would then be in a position to correspondingly determine the average optical characteristics of a given length section of the paper web 14, for example, and control suitable inputs to the paper machine so as to maintain desired optical characteristics of the paper being manufactured. Alternatively, of course, the arrangement of FIGS. 1-6 can be utilized simply to take readings from the meter 330 for each filter wheel position during scanning of the web, so as to obtain readings reflecting the optical characteristics of the length sections of the web so scanned. Still further, of course, the circuitry of FIGS. 5 and 6 can be utilized either with the monitoring device located in a fixed position relative to the width of the web (by means of a C-type frame), or with the device off-line from the paper machine, so as to obtain desired readings from the meter 330 for each position of the filter wheel 210 during optical excitation of a single sheet sample of the web held in a sample holder so as to be disposed essentially as indicated for the web 14 in FIG. 3.

Exemplary Commercially Available Components

Commercially available components which are included in the present design of FIGS. 1-6 are as follows.

Main power supply. Lambda Electronics Corporation Model LQS-DA-5124 providing a direct current (DC) output voltage of 24 volts and a maximum current at 40° C. of 5 amperes.

Reed switches. For reflectance amplifier gain settings—Model MMRR-2, and for transmittance amplifier gain settings-Model MINI-2, manufactured by Hamlin, Inc. The relays in the lower sensing head of Type 821A of Grigsby-Barton, Inc.

Operational amplifiers, Model 233J chopper stabilized amplifiers of Analog Devices, Inc. Model 904 power supply supplying plus or minus 15 volts with a minimum full load output current of plus or minus 50 milliamperes.

Digital panel meter (used for off-line studies and for on-line operation before being interfaced with the computer). Weston Model 1290.

Filter wheel advance solenoid Type T 12×13-C-24 volt DC flat plug plunger of Guardian Electric Manufacturing Company. Antibottoming washer made of polyurethane rubber. Operation of the solenoid until interfaced with the computer has been with the use of a time adjusted relay, namely a Model CG 102A6 transistorized repeat cycle timer of G. & W. Eagle Signal Co.

Filter wheel drive motor. Type 1AD3001 Siemens brushless DC motor. The drive belt and pulleys for coupling the motor 209 with the shaft 208 are specified as positive drive belt FS-80 and positive drive pulleys FC5-20 and FC5-40 of PIC Design Corporation, a Benrus subsidiary. The belt has a stainless steel core and the pulleys have a ¼ inch diameter bore.

Computer Interfacing

In preparing the monitoring device for on-line operation on the paper machine, the zero to 140 millivolt DC signals from the sensing heads will be supplied to respective emf-to-current converters of component 501, FIG. 6. As an example, Rochester Instrument Systems Model SC-1304 emf-to-current converters may be used. Such a converter will provide an output of 10 to 50 milliamperes DC suitable for driving an analog to digital converter at the computer. The emf-to-current converters will provide an isolated input and output so that grounding will not be a problem.

The converters are component 501, will be housed with optical analyzer 300, FIG. 5, and will connect with respective points thirty one of Groups five hundred and six hundred (not shown) at the control computer analog signal input via conductors such as indicated at 502 and 503 in FIG. 6.

Conductors 505 and 506, FIG. 6, associated with filter wheel indexing solenoid 240, FIGS. 3 and 6, may extend within control conduit 312, FIG. 5, and connect with the control computer output terminals at a location designated Group forty two hundred and six, point nineteen (not shown). (Switch 334 should remain open (off) during computer operation of FIGS. 1-6.)

Conductors 359 and 360, FIG. 6, may connect with an input of the control computer at a location designated Group fourteen hundred, point twenty-three (not shown).

DISCUSSION OF AN EARLIER PROTOTYPE SYSTEM

Structure and Operation of a Prototype Optical Monitoring Device

A prototype optical monitoring device was first constructed so as to test the feasibility of the concepts of the present invention. As a result of the experimental work with the prototype system, a preferred system has been designed and will hereinafter be described in greater detail. Since the operation of the prototype system is somewhat different from that of the later designed system, a description of the prototype system will serve to illustrate alternative features and an alternative method of operation in accordance with the present invention.

In the original setting up of the prototype system, the upper and lower sensing heads should be brought into proper alignment and spacing. The spacing should be just under ¼-inch between the case 110 and the surface of the diffusing glass of window 135. (In the prototype unit, there were no additional parts between the case 110 and window 135 such as the shoe plate 122 shown in FIG. 3.) The lower sensing head should be moved laterally in all directions to locate the point where the maximum reading occurs from photocell 260 as well as the point of least sensitivity to relative movement of the upper and lower sensing heads. In an initial calibration of the prototype monitoring device, potentiometers are included as part of the resistance means 371-377 and 431-437 and are adjusted for the respective positions of the filter wheel 210 to give the correct readings for the reflectance and transmittance of the diffusing glass 135 (in the absence any paper sample between the upper and lower sensing heads). The values which were used in this initial calibration are indicative of percentage absolute reflectance and transmittance on a scale of 100, and are as follows:

TABLE 1

Table Showing Exemplary Calibration for the Prototype System-
Diffusing Glass Reflectance and Transmittance Values With No Paper Specimen Present

| Filter Wheel Position No. | Reflectance Value, RSD (Millivolts) | Transmittance Value, TSD (Millivolts) |
|---|---|---|
| 1 | 35.4 | 54.0 |
| 2 | 35.0 | 56.1 |
| 3 | 34.4 | 56.9 |
| 4 | 34.6 | 56.6 |
| 5 | 34.7 | 56.4 |
| 6 | 34.5 | 56.6 |

TABLE 1-continued

Table Showing Exemplary Calibration
for the Prototype System-
Diffusing Glass Reflectance and Transmittance
Values With No Paper Specimen Present

| Filter Wheel Position No. | Reflectance Value, RSD (Millivolts) | Transmittance Value, TSD (Millivolts) |
| --- | --- | --- |
| 7 | 34.8 | 0.6* |

*The transmittance value of the No. 7 filter position is not needed, and consequently a low amplification of this signal was arbitrarily selected.

The readings in millivolts can be converted to other desired units by comparing the readings in millivolts for a given paper specimen with the readings obtained with a standard laboratory instrument, measuring the reflectance of the specimen with the laboratory instrument while backing the paper sheet with a piece of Lucalux and a black body. By measuring the reflectance of the single sheet backed with a black body (no fluorescence), the value of transmittance for the specimen can be calculated and this calculated value utilized for calibrating the lower sensing head. If the fluorescent component is included in the laboratory instrument, and if fluorescence is involved, the fluorescence component can be determined by means of a standard reflection meter, and the fluorescent component can then be subtracted from the measured data before making the calculation of transmittance.

The laboratory testing of the prototype system confirmed that a monitoring device such as illustrated in FIGS. 1-4 should have a potential accuracy equal to that of comparable off-line testers provided certain web scanning requirements are met.

Laboratory tests were run on color standard samples of the grades and colors usually run on the paper machine shown in FIGS. 1 and 2. In addition, a variety of opaques, and a variety of colored 50 pound and 70 pound offsets were included in the tests. A four centimeter diameter circle was scribed on each sample to insure that all tests would be done within the same 12 square centimeter section of the sample. Values of $R_o$, $R_{oo}$, and TAPPI opacity measurements were made on the available standard laboratory instruments. All test were made on the felt side of the sample with the grain in the standard direction. For $R_{oo}$ measurements, the samples were backed by piles of tabs cut from the edge of the same sheet of paper. In addition to the TAPPI opacity measured on the standard opacimeter, TAPPI opacity was calculated via Kubelka-Munk theory from data obtained with a standard automatic color-brightness tester.

The sample paper samples were clamped to a holder which held the sample under tension with the lower head of the monitoring device bellying $\frac{1}{8}$-inch to $\frac{1}{4}$-inch into the sheet. The grain of the sheet was oriented parallel to the longitudinal axis of the upper sensing head (that is the machine direction of the sheet was in the same orientation as would occur on the paper machine as indicated in FIGS. 1 and 2). The felt side was always up. Care was taken to make sure that the tested area was within the twelve square centimeter circle scribed on the sample.

The transmittance and reflectance readings were taken from a digital volt meter attached to the output terminals of amplifiers 361 and 429. Calibration data was taken off the Lucalux with no sheet present. Test values were taken on all filters with the sheet in place. The transmittance and reflectance values were keyed into a standard calculator with the calibration data. The calculator was programmed to calculate the color (in C.I.E. X, Y, Z, for example), fluorescent component, brightness, TAPPI opacity and printing opacity (based on $Y_c$). By supplying the basis weight, the computer could also be requested to calculate s, the scattering coefficient (an index of the effect of pigment efficiency and fiber surface area), and k, the absorption coefficient (an index of the effectiveness of dyes in the sheet). The coefficients s and k are essentially independent of basis weight. Kubelka-Munk theory is the basis of the calculations used.

All of the samples were tested without changing the relative position of the two sensing heads. One set of data was obtained with the heads in a variety of positions to determine the effect of geometric variations.

Since fluorescence is not compatible with Kubelka-Munk theory, the prototype system was carefully designed so that all data used for Kubelka-Munk analyses have excluded fluorescence. The prototype system measures fluorescence separately. A fluorescent contribution is determined from the prototype data by subtracting the Z distribution reflectance without fluorescence (filter wheel position No. 4) from the Z distribution reflectance with fluorescence (filter wheel position No. 7), and multiplying by the appropriate factor.

An independent check on fluorescence measurements, a modified brightness tester was utilized which had a filter wheel allowing for standard brightness and Z distribution filters to be put in the reflected beam. In addition, the filter wheel contained brightness and Z distribution filters which had been modified by removing the ultraviolet absorbing component of these filters. A special mount allows the operator to put the appropriate ultraviolet absorbing filter in the incident beam. Thus, measurements of brightness and C.I.E. Z tristimulus, with and without fluorescence, could be made. Fluorescent contributions were calculated by difference. Some measurements were made on signal sheets with a standard backing. Most of the samples were measured with an infinite pack of tabs. The incident beam filter of the prototype's No. 7 position was such that it permitted about twice the standard quantity of ultraviolet light to strike the specimen. Consequently, measurements of the fluorescent contribution measured on the modified brightness tester and the prototype system correlated well (correlation coefficient of 0.992) but the modified brightness tester value is only 0.528 as large as that measured by the prototype system. Calculations of prototype data now involve calculation of the fluorescent component by multiplying the difference of filter positions No. 7 and No. 4 by 0.528.

Because only one fluorescent dye (Tinopal) in all of the paper specimens was used, the fluorescent contribution needed to be measured only once. The prototype data provides a basis for measuring the fluorescent component Z. Measurements by an independent laboratory showed that the paper specimens do not fluoresce significantly in the X (red) or Y distributions; therefore, fluorescent contributions need only be determined for the blue colored distributions. A linear regression was run on the independent laboratory data which demonstrated that the fluorescent component for X (blue) can be predicted by multiplying the fluorescent component for Z by 1.204. A regression run on fluorescent data from the modified brightness tester shows that the fluorescent contribution for brightness can be calculated by multiplying the fluorescent contribution for Z by 0.864. In summary, fluorescent contributions are calculated by the following formulas:

$F_Z = 0.528$ (Z reflectance with fluorescence minus Z reflectance without fluorescence.)

$F_{X(blue)} = 1.204 \, F_Z$ $F_{Brightness} = 0.864 \, F_Z$

These fluorescent contributions are added to the respective calculated $R_{oo}$ values when calculating optical properties from prototype data. The test results for fluorescent and non-fluorescent papers agree with values measured on the standard automatic color-brightness tester.

Discussion of the Results of Mechanical Life Testing of the Prototype System and Design Features Selected for the Preferred System In Light of Such Life Testing The following details concerning the results of life testing of the prototype system are considered to reflect minor problems of construction and operation which considered individually are readily corrected for by those skilled in the art. In order to minimize the burden of the total number of such minor problems, and thus to expedite practice of the prototype system, solutions to the various problems which were encountered are briefly referred to.

The filter wheel is advanced by a low torque stallable motor. A timing belt links sprockets on the motor and the filter wheel shaft. The original timing belt had a dacron core. The core of the original belt broke in two places resulting in stretching and eventual loss of teeth. Uneven rate of rotation of the filter wheel occurred due to binding of the belt. Eventually, the plastic drive sprocket broke. Both sprockets were replaced with stainless steel sprockets and the timing belt was replaced with a belt containing a steel core. Installation of the steel sprockets and steel core belt revealed that excessive belt tension could stall the motor. The motor mount holes were slotted allowing the motor to pivot slightly around one mounting screw. Belt tension was adjusted by pivoting the motor. It is concluded that future models should include an idler wheel or some other means of adjusting the tension of the timing belt.

Some problems were experienced with respect to indexing of the filter wheel with the ratchet arm sticking on the tooth so that the ratchet arm does not clear the tooth when a command is given to index the filter wheel. The remedy has been to reduce the roughness of the mating surfaces by filing on the tooth, or smoothing the tooth with a stone. In future models, the shapes and/or smoothness of the ratchet arm and the teeth should be altered to minimize sticking. One solution would be to provide the ratchet arm and the teeth with highly polished mating surfaces.

The ratchet arm is lifted by a 24 volt direct current solenoid. After some time, the plunger of the solenoid became magnetized and would stick to the inside of the coil. This "hanging up" would prevent the ratchet arm from catching the next tooth. A resistor was installed in series with the solenoid coil to reduce the strength of the magnetic field. The plunger of the solenoid was coated with a special material. The coated plunger worked well for about three months before it, too, magnetized enough to hang up. The solution adopted was to provide the solenoid with a flat topped plunger which is stopped at the end of its stroke by a bumper of rubber-like material.

The response of a photocell is somewhat temperature sensitive. For this reason, it is necessary to keep the photocells at a constant temperature. Ambient temperatures on the O-frame of the No. 6 paper machine indicated in FIGS. 1 and 2 have been measured as high as 118° F.(48° C.) in the summer. The photocells in both heads are mounted in massive metal blocks. Each metal block has four thermistor heaters mounted in close proximity to the photocell. These thermistors have switching temperatures of 55° C., (that is about 130° F.). The intention of this design was to add enough heat to the instrument to hold the temperature steady at about 55° C. During bench studies, this temperature was never reached due to the low capacity of the heaters. At machine room temperatures, however, the instrument temperature may reach 55° C.

During the bench studies, it was found that the heaters did minimize temperature variations. The few degrees of temperature variation that were observed during normal operation usually occurred slowly. Changes in instrument temperature affected the output signal less than acticipated. Based on this experience in the laboratory, the maximum variation in head temperature should be less than 3° F. per hour. Temperature variations of this magnitude will not have a significant effect on the output signal. Long term temperature changes would be corrected for by the calibrations each time the head goes off web.

In the laboratory, there was a minimum of dirt problems. On the machine, however, the hole could allow dirt to enter the upper head. Up to a point, dirt on the lenses and filters will be corrected for by the periodic calibration routine. Excessive dirt, however, will reduce the sensitivity of the instrument and may even affect its accuracy. Periodic cleaning of the lexses and filters will be required. If dirt accumulates too rapidly, it may be necessary to attach an air purge to the upper head.

The lower head of the prototype system is completely sealed so that no dirt problem is anticipated inside the lower head. Because the Lucolux window is in contact with the sheet, friction will keep it clean.

Most of the filters consisted of two or three component parts. There have been some problems with dirt getting between the components of the filters.

The case on the lower head as well as the case on the upper head should allow most general maintenance and trouble-shooting to be done without dismounting the head. A completely removable case would be desirable. At a minimum access should be provided for the following: (1) convenient light bulb change, (available on the prototype), (2) cleaning of lenses, (available on the prototype), (3) cleaning of the filters. (Access is presently available to one side of each filter. The side which is most likely to collect dirt is not accessible in the prototype.) (4) The amplifier. The amplifier is a standard plug-in module. In the event of a breakdown it could be replaced in seconds if it is accessible. Furthermore, it is necessary to remove the amplifier to do any trouble-shooting on the gain circuitry. (5) The circuit board holding all of the gain control resistors. The choice of gain circuitry is controlled by reed switches which are not accessible on the prototype without a partial disassembly of the instrument. Malfunctions of the reed switches, however, can easily be diagnosed by removing the amplifier and taking resistance measurements on the gain control circuits. There is also the possibility of mechanical or electrical damage to a resistor or a potentiometer mounted on this circuit board. With proper access a damaged part could be replaced in five to twenty minutes. (6) The photocell. With proper access, the photocell could be replaced quickly and easily. (7) The heater. The heater are adjacent to the photocell and are generally just as easily serviced. (8) Indexing mechanism. The present accessibility to the ratchet teeth, rachet arm and solenoid is adequate but not very convenient on the prototype. A certain amount of access to these parts is needed to correct chronic indexing problems such as sticking and "hanging up".

The filters are presently mounted in the filter wheel of the prototype by spring clips. Most of the filters are compound filters containing as many as four component pieces of glass. During laboratory trials, increases in the optical density of a filter were frequently observed which could not be corrected by cleaning the surfaces of the filter. Upon removing one of the filters, it was discovered that foreign material was collecting between the components of the compound filter. The use of lens cleaning solution on the filters may have accelerated the problem if capillary action drew foreign material between the components. A set of gaskets and some type of threaded mount should be used to mount the filters in such a way as to minimize foreign material (including cleaning solutions) from getting between the components of compound filters.

In mounting the prototype sensing heads on an O-frame, it is necessary to bring the geometric alignment of the heads as close to their optimum relationship as possible. The original intention was to set the gap between the heads with the aid of a spacer; however, flexibility of the sheet metal case of the prototype upper sensing head prevented the use of a spacer for setting the gap. Accordingly, the shoe plate 122 of the new upper sensing head shown in FIG. 3 has been made of a thickness and consequent rigidity so as to enable the use of a spacer gauge to set the gap between the upper and lower heads. (The gap is reduced by 1/16 inch to 3/16 inch because of the thickness of shoe plate 122.)

The gap between the heads is a most critical dimension as far as calibration and reproducability is concerned. In the prototype it was intended to calibrate relative to an average gap, thus correcting the readings for variations in the gap from the average gap.

One of the criteria used in designing the prototype was minimum head length in the machine direction. Unfortunately, the upper head was turned 90° in order to give the prototype unit the same geometry as the General Electric Brightness Meter, Automatic Color-Brightness Tester, and Hunterlab Color Meter. In this new position, the prototype head is $12\frac{1}{4}$ inches long in the machine direction plus $2\frac{1}{2}$ inches for cable connectors. Redesign should be possible to reduce the machine direction dimension to about 8 inches and to relocate the position of the cable connections.

The lining of the case for the upper head should be matte as well as black to prevent reflection of ambient light within the case and a possible spurious effect on the photocell reading.

Conclusions from Mechanical Testing of the Prototype System

Following the correction of miscellaneous start up problems the prototype system was found to function well mechanically. As a test of its durability, the prototype system was placed in continuous operation for a period of over ten months and no serious mechanical problems resulted except the failure of the solenoid. The solenoid failure was expected and the replacement solenoid is of a design which is expected to give a long service life. The light application of silicone lubricant spray to the indexing control ratchet arm and cooperating teeth corrected a problem of malfunctioning of the filter wheel indexing mechanism (which occurred on two occasions during the ten months). The prototype system was not intended to be a low maintenance instrument; however, the experience during the durability test with the prototype in continuous operation indicates that the prototype system should operate on a paper machine with an acceptably small amount of down time.

DISCUSSIOIN OF LABORATORY TESTING OF FIGS. 3-6

Laboratory Operation of the System of FIGS. 3-6

In the prototype system, potentiometers are included as part of the resistance means 371-377 and 431-437 and are adjusted for the respective positions of the filter wheel 210 to give desired values such as given in the foregoing Table 1. In the preferred system of FIGS. 3-6, these potentiometers for adjusting amplifier gain are omitted and are replaced with fixed resistors 371-377 and 431-437 selected to give scale readings from meter 330 in the respective filter wheel positions which are well above the values given in the preceding Table 1. This is intended to improve the stability and increase the sensitivity of measurement.

In calculating optical parameters from measurements relative to various samples, values were first established for the reflectance RD of the diffuser 135, FIG. 3, in the absence of a paper specimen, for each filter wheel position. Initially calculated values for RD were used in a first computation of optical values, and then the values of RD were adjusted slightly to give the best agreement with the corresponding optical measurements by means of the standard automatic color-brightness tester. The following table shows the reflectance values which were established for certain laboratory testing of the system of FIGS. 3-6.

TABLE 2

Table Showing Reflectance of the Diffusing Glass With No Paper Specimen Present in a Laboratory Test of the System of FIGS. 1-6

| Filter Wheel Position No. | Symbol | Diffusing Glass Reflectance Value |
|---|---|---|
| 1 | RD1 | 0.349 |
| 2 | RD2 | 0.347 |
| 3 | RD3 | 0.355 |
| 4 | RD4 | 0.349 |
| 5 | RD5 | 0.354 |
| 6 | RD6 | 0.354 |
| 7 | RD7 | 0.349 |

The transmittance of the diffusing glass 135 need not be known since the ratio of the transmittance of the diffusing glass and paper (in series) to the transmittance of the diffusing glass is employed in calculating the desired optical parameters.

A computer program was developed to process the data collected during laboratory operation of the monitoring device 10 as well as to compare the calculated reflectance value $R_{oo}$ and the calculated fluorescent components with the data collected with the standard automatic color-brightness tester. A listing of the symbols employed in a symbolic statement of the computer program in the Fortran computer language utilized in this laboratory study is set forth in Table 3 on the following pages.

TABLE 3

Listing of Symbols (Including Input Data Symbols and Output Data Symbols With a Brief Indication of Their Significance).

| | Input Data Symbols |
|---|---|
| RSD | OMOD scale reading for reflectance with no paper specimen in place. (Filters 1 through 6.) |
| RSP | OMOD scale reading for reflectance with paper specimen in position. (Filters 1 through 6.) |
| TSD | OMOD scale specimen reading for transmittance with no paper specimen in place. (Filters 1 through 6.) |
| TSP | OMOD scale reading for transmittance with paper specimen in position. (Filters 1 through 6.) |
| RSD7 | OMOD scale reading for reflectance with no specimen in place. (No. 7 filter.) |
| RSP7 | OMOD scale reading for reflectance with paper specimen in position. (No. 7 filter.) |
| $AR_{oo}FC$ | ACBT reflectance including the fluorescent component. |
| AFC | ACBT fluorescent component. |
| RSD4 | OMOD scale reading for reflectance with no paper specimen in place. (No. 4 filter.) |
| RSP4 | OMOD scale reading for reflectance with paper specimen in position. (No. 4 filter.) |
| GC | Grade Correction as determined by the difference between $R_{oo}FC$ and $AR_{oo}FC$ for each sample and each filter. |
| | Output Data Symbols |
| $R_o$ | Reflectance of a single sheet backed with a black body (no fluorescence) as calculated from OMOD data. |
| T | Transmittance of a single sheet backed with a black body (no fluorescence) as calculated from OMOD data. |
| $R_{oo}$ | Reflectance of an opaque pad (no fluorescence) as calculated from OMOD data. |
| $R_{oo}FC$ | Reflectance of an opaque pad (including fluorescence) as calculated from OMOD data. |
| $AR_{oo}FC$ | Reflectance of an opaque pad (including fluorescence) ACBT. |
| DIFF | Difference between $R_{oo}FC$ and $AR_{oo}FC$. |
| FC | Fluorescent component OMOD. |
| AFC | Fluorescent component ACBT. |
| GC | Grade Correction as determined by the difference between $R_{oo}FC$ and $AR_{oo}FC$ for each sample and each filter. |
| Additional Symbols | Used in the Computation of the Output Data from the Input Data) |
| RK | Reflectance correction factor (assigned a value of 1.000 for laboratory operation). |
| TK | Transmittance correction factor (assigned a value of 1.000 for laboratory operation). |
| RD | Value representing the absolute reflectance of the diffuser (on a scale of zero to 1.000) as adjusted to give best agreement with optical measurements by means of the standard automatic color-brightness tester. (The values given in Table 2 are used for laboratory operation.) |
| RPD | Reflectance of paper specimen when backed with the diffuser, as calculated from current values of RK, RD, RSD, and RSP. |
| TPD | Transmittance of paper speciment and diffuser in series, as calculated from current values of TK, |

TABLE 3-continued

Listing of Symbols (Including Input Data Symbols and Output Data Symbols With a Brief Indication of Their Significance).

TSD, and TSP.

In the foregoing listing of symbols, the letters of the symbol OMOD are taken from the phrase on-machine optical device; however, this particular section of the specification refers to a system essentially conforming to the system of FIGS. 3-6 operated to measure optical properties of individual paper sheets under laboratory conditions. (The laboratory work here reported was with an earlier version of the monitoring device designed for on-machine operation, prior to adoption of a thickened shoe plate 122. The standard spacing between the upper and lower sensing heads for the earlier version was ¼ inch, rather than 3/16 inch as with the final version of on-machine device as specifically shown in FIG. 3.) The OMOD scale readings are obtained from the meter 330, FIGS. 5 and 6, with the filter wheel 210, FIGS. 3 and 4, in the respective positions to activate the respective filters 281-286 (indicated as "Filters 1 through 6" in the preceding listing) and to activate filters 287 and 288 (indicated as "No. 7 filter" in the listing), and with switch 331, FIG. 5, in its upper position to measure reflectance, and in its lower position to measure transmittance. As to reflectance measurements, the cavity 145 is considered to form essentially a black body backing for the diffusing glass 135.

The symbol "ACBT" in the foregoing listing of symbols is used to designate a measurement made on the standard commercially available automatic color-brightness tester. The brightness measurement obtained from the ACBT represents a value accepted as standard in the U.S. Paper industry. A further appreciation of the importance of the fact that the OMOD measurements can closely conform to this industry standard is gained from a consideration of the article by L. R. Dearth et al "A Study of Photoelectric Instruments for the Measurement of Color Reflectance, and Transmittance, XVI. Automatic Color-Brightness Tester", *Tappi, The Journal of the Technical Association of the Pulp and Paper Industry*, Vol. 50, No. 2, February 1967, pages 51A through 58A. As explained in this article, the ACBT is photometrically accurate, and the spectral response is correct for the measurement of both color and standard brightness. The spectral response of the ACBT very nearly matches the theoretical CIE functions as indicated by the special technique for determining spectral response. This involves the determination of the tristimulus values for deeply saturated colored glass filters a very rigorous check on the spectral response, especially when it is noted that colored papers are less saturated.

The symbols in the foregoing Listing of Symbols which as shown include lower case characters may also be written exclusively with capital letters. This form of the symbols is convenient for computer printout. The alternate forms of these symbols are as follows: $AR_{oo}FC$ or AROOFC; $R_o$ or RO; $R_{oo}$ or ROO and $R_{oo}FC$ or ROOFC.

TABLE 4

Symbolic Statement of the Computer Program (Used for Processing the Data Obtained During the Laboratory Operation of the System of FIGS. 3-6)

6PS FORTRAN    D  COMPILER

TABLE 4-continued

Symbolic Statement of the Computer Program
(Used for Processing the Data Obtained During the
Laboratory Operation of the System of FIGS. 3-6)

|  |  |  |
|---|---|---|
|  |  | C    OMOD (220) |
| S.0001 |  | WRITE (6,2001) |
| S.0002 | 2001 | FORMAT (1H, 'SAMPLE', 6X, 'RD', 12X, 'T', 12X, 'ROO', 9X, 'ROOFC', 9X, 1'AROOFC', 10X, 'DIFF', 7X, 'FC', 7X, 'AFC', 7X, 'GC', /) |
| S.0003 |  | READ (5,1000) RK, TK, RD1, RD2, RD3, RD4, RD5, RD6 |
| S.0004 | 102 | M=O |
| S.0005 |  | READ (5,1000) RSD4, RSP4 |
| S.0006 | 1000 | FORMAT (10F8.0) |
| S.0007 | 100 | READ (5,1001) IA, IN, ID, RSD, RSP, TSD, TSP, RSD7, RSP7, AROOFC, AFC, R |
| S.0008 | 1001 | FORMAT (I2, I2, A4, 9F8, 0) |
| S.0009 |  | GO TO (11, 12, 13, 14, 15, 16), IN |
| S.0010 | 11 | RD=RD1 |
| S.0011 |  | GO TO 17 |
| S.0012 | 12 | RD=RD2 |
| S.0013 |  | GO TO 17 |
| S.0014 | 13 | RD=RD3 |
| S.0015 |  | GO TO 17 |
| S.0016 | 14 | RD=RD4 |
| S.0017 |  | GO TO 17 |
| S.0018 | 15 | RD=RD5 |
| S.0019 |  | GO TO 17 |
| S.0020 | 16 | RD=RD6 |
| S.0021 | 17 | RPD=((RD*RSP*RK)/RSD) |
| S.0022 |  | RPD4=RD4*RSP4*RK/RSD4 |
| S.0023 |  | TPDOTD=(TSP*TK)/TSD |
| S.0024 |  | RO=(RPD−(RD*(TPDOTD**2)))/(1.−(RD* TPDOTD)**2) |
| S.0025 |  | T=(TPDOTD*(1.−(RD*RPD)))/(1.−(RD*TPDOTD)**2) |
| S.0026 |  | A=((1.+(RO2))−(T2))/RO |
| S.0027 |  | ROO=(A/2.)-SQR[(((A/2.)**2)−1.)] |
| S.0028 |  | RPD7=RD4 *RSP7*RK/RSD7 |
| S.0029 |  | IF (IN−2)1, 2, 3 |
| S.0030 | 3 | GO TO (7, 7, 7, 4, 7, 7), IN |
| S.0031 | 1 | FC=(RPD7−RPD4)*.450 |
| S.0032 |  | GO TO 6 |
| S.0033 | 2 | FC=(RPD7−RPD4)*.570 |
| S.0034 |  | GO TO 6 |
| S.0035 | 4 | FC=(RPD7−RPD4)*.510 |
| S.0036 | 6 | ROOFC=ROO+FC |
| S.0037 |  | GO TO 30 |
| S.0038 | 7 | ROOFC=ROO |
| S.0039 |  | FC=0.0 |
| S.0040 | 30 | IF (IA−2)18, 19, 19 |
| S.0041 | 18 | ROOFC=ROOFC+R |
| S.0042 |  | GO TO 20 |
| S.0043 | 19 | ROOFC=ROOFC−1 |
| S.0044 | 20 | DIFF=ROOFC−AROOFC |
| S.0045 |  | GO TO (21,22), IA |
| S.0046 | 21 | WRITE (6,2000)ID,RO,T,ROO, ROOFC, AROOFC, DIFF, FC, AFC, R |
| S.0047 | 2000 | FORMAT (IH A4, 7X, 2(F8.6, 4X), 4 (F10.6, 4X), 2(F5.4, 4X), '+', F4.3) |
| S.0048 |  | TO TO 23 |
| S.0049 | 22 | WRITE (6,2002)ID, RO, T, ROO, ROOFC, AROOFC, DIFF, FC, AFC, R |
| S.0050 | 2002 | FORMAT (IH, A47X, 2(F8.6, 4X), 4 (F10.6, 4X), 2(F5.4, 4X), '−', F4.3) |
| S.0051 | 23 | M=M+1 |
| S.0052 |  | IF(M−6) 100,102,102 |
| S.0053 | END |  |
|  |  | SIZE OF COMMON OOOOO |
|  |  | PROGRAM 01930 |
|  |  | END OF COMPILATION MAIN |

In the foregoing Table 4, the symbols representing basic mathematical operations were as follows:

| Operation | Symbol | Example |
|---|---|---|
| Addition | + | A+B |
| Subtraction | − | A−B |
| Multiplication | * | A*B |
| Division | / | A/B |
| Exponentiation | ** | $A**B(A^B)$ |
| Equality | = | A=B |

To indicate more concretely the calculations which are performed, the following Table 5 will illustrate exemplary input and output data for a given sample. The meaning of the various symbols will be apparent from the listing of the symbols of Table 3:

TABLE 5

Table Showing Exemplary Input and Output Data for a Given Sample

Sample No. 1, white Nekoosa Offset-60 pound paper, specimen A RK=1.000, TK=1.000

| Filter Wheel Position No. Input Data | 1 | 2 | 3 | 4 | 5 | 6 |
|---|---|---|---|---|---|---|
| RD | 0.349 | 0.347 | 0.355 | 0.349 | 0.354 | 0.354 |
| RSD | 0.515 | 0.529 | 0.583 | 0.636 | 0.525 | 0.596 |
| RSP | 1.161 | 1.187 | 1.339 | 1.422 | 1.191 | 1.357 |
| TSD | 1.422 | 1.625 | 1.627 | 1.702 | 1.625 | 1.546 |
| TSP | 0.236 | 0.256 | 0.354 | 0.277 | 0.335 | 0.326 |
| RSD7 | 0.568 | 0.568 | 0.568 | 0.568 | 0.568 | 0.568 |
| RSP7 | 1.381 | 1.381 | 1.381 | 1.381 | 1.381 | 1.381 |
| AROOFC | 0.837 | 0.829 | 0.847 | 0.830 | 0.839 | 0.844 |
| AFC | 0.034 | 0.034 | 0.0 | 0.036 | 0.0 | 0.0 |
| RSD4 | 0.636 | 0.636 | 0.636 | 0.636 | 0.636 | 0.636 |
| RSP4 | 1.422 | 1.422 | 1.422 | 1.422 | 1.422 | 1.422 |
| GC | −0.006 | −0.014 | −0.021 | −0.007 | −0.009 | −0.012 |
| RO | 0.779777 | 0.772313 | 0.803330 | 0.773563 | 0.792249 | 0.794690 |
| T | 0.120798 | 0.115319 | 0.155529 | 0.118812 | 0.148337 | 0.151546 |
| ROO | 0.812093 | 0.800173 | 0.874419 | 0.803542 | 0.849399 | 0.856230 |
| ROOFC | 0.836794 | 0.824838 | 0.853419 | 0.831337 | 0.840399 | 0.844230 |
| AROOFC | 0.837000 | 0.829000 | 0.847000 | 0.830000 | 0.839000 | 0.844000 |
| DIFF | −0.000206 | −0.004162 | 0.006419 | 0.001337 | 0.001399 | 0.000230 |
| FC | .0307 | .0387 | .0 | .0348 | .0 | .0 |
| AFC | .0340 | .0340 | 0 | .0360 | .0 | .0 |

TABLE 5-continued

Table Showing Exemplary Input and Output Data for a Given Sample

Sample No. 1, white Nekoosa Offset-60 pound paper, specimen A RK=1.000, TK=1.000

| Filter Wheel Position No. Input Data | 1 | 2 | 3 | 4 | 5 | 6 |
|---|---|---|---|---|---|---|
| GC | −.006 | −.014 | −.021 | −0.007 | −.009 | −0.12 |

In the foregoing table showing exemplary input and output data, the input and output data symbols have been shown as they are actually printed out by the computer with all letters capitalized. In the text, certain of the input and output data symbols are shown in a more conventional manner with subscripts since the symbols are more familiar in such form.

The data such as exemplified in Table 5 are based on a single determination for each specimen. The "grade correction" GC is based on the average difference between $R_{oo}FC$ and $AR_{oo}FC$ for two specimens, specimens A and B.

The data as exemplified in Table 5 show that there is generally good agreement between the calculated $R_{oo}FC$ and $AR_{oo}FC$ values. The spread in values for the duplicate specimens (A and B) is good with the exception of several samples. Some difficulty was experienced in positioning the specimen on the monitoring device 10 to give reproducible results. The difficulty should be minimized when the unit is placed "on-machine". The grade correction GC takes this discrepancy into consideration so the correction should be established "on-machine".

The RD values shown in Table 5 were punched into the first data card along with the values for RK and TK for input to the computer in advance of a desired computation. The factors RK and TK were included as factors in the computations so that the transmittance and reflectance values could be adjusted independently, if desired. In this evaluation, RK and TK were left at 1.000. (Calculated values for RD were used in a first computer run and then the values were adjusted slightly to give the best agreement with the standard automatic color-brightness tester. The values for RD shown in Table 5 are the slightly adjusted values utilized in obtaining the data discussed in this section of the specification.)

A second set of data for the same fourteen samples was collected using the monitoring device in the same condition as for the collection of the data previously given. All of the variables were left the same to see how closely the data could be reproduced for the identical specimens. The agreement was quite good except for samples 8 and 14. It appears that the paper may not have been lying flat in one or the other tests. The grade correction GC on some of the grades was changed and the second set of data was again calculated for samples 1, 2, 4, 5, 6, 8 and 14. This improved the agreement between the monitoring device and the standard automatic color-brightness tester.

The reflectance head of the monitoring device was then lowered 0.025 inch and another set of data was collected for the same seven samples. The same ACBT data was used. The data show that lowering the reflectance head reduces the reflectance while transmittance remains essentially unchanged. The effects are not as large as was expected and could be corrected through adjustment of RK; however, the variables RK, TK and GC were again held constant.

The reflectance head was then raised to a spacing of 0.050 inch (0.025 inch above the normal position for these tests), and another set of data was collected for the same seven samples. The effects were larger than when the reflectance head 11 was lowered. Again, an adjustment of RK would improve the agreement.

It was concluded from these test results that a change of plus or minus 0.025 inch from "normal position" is larger than can be tolerated. An estimate of a reasonable tolerance, based on this and earlier work, would be plus or minus 0.010 inch from "normal position".

All of the variables used in calculating the data for samples 1, 2, 4, 5, 6, 8 and 14, after the initial change in the grade correction GC, were held the same to determine the effects of changing the reflectance head position. The same input data for the case of the reflectance head being raised 0.025 inch were processed again but with RK equal to 0.975 instead of 1.000. This reduces the reflectance value to the proper level. The data obtained in this way show good agreement between the monitoring device and the standard automatic color-brightness tester. Apparently the factor RK can be used quite effectively in adjusting for some variation in the geometric relationship of the upper and lower sensing heads. It would be preferred, of course, to maintain proper alignment and spacing.

A second set of samples were evaluated after returning the reflectance head to its normal spacing from the transmittance head. Before calculating new output data, the computer program of Table 4 was corrected in statements S.0022 and S.0028 by changing RD to RD4. The corrected computer program has been shown herein since the error in the previously referred to data was insignificant in most cases. Thus with the corrected computer program, the input data for the second set of samples were processed. The values RK and TK were set to 1.000 and the same grade corrections were used as for samples 1, 2, 4, 5, 6, 8 and 14 previously referred to.

Conclusions drawn from all of the data are that the grade correction GC will handle errors resulting from less than ideal characteristics of the monitoring device 10 such as the relatively wide bandwidth of light transmitted in the various filter positions in comparison to the requirements of Kubelka-Munk theory and the fact that this theory applies strictly only to diffuse light rather than collimated light as actually employed in the illustrated monitoring device 10. This correction must be established "on-machine". Use of the diffusing glass 135 to calibrate the monitoring device 10 will handle changes in light level, photocell sensitivity and amplifier gain. The reflectances RD of the diffusing glass 135 for the various filters as established in the present work are set forth in the previous Table 2 entitled "Table Showing Reflectance of the Diffusing Glass With No Paper Specimen Present in a Laboratory Test of the System of FIGS. 1-6".

As previously mentioned, the transmittance of the diffusing glass 135 need not be known as the ratio of the transmittance of the diffusing glass and paper (in series), identified by the symbol TSP, to the transmittance of the diffusing glass 135, identified by the symbol TSD, is employed as will be apparent from the explanation of the calculations employed set forth hereinafter.

The fluorescent component is handled through the difference in reflectance as measured with the number 4 and the number 7 filters (RPD7 minus RPD4). The factors used in the subject computations, for filters number 1, 2 and 4, are 0.500, 0.600 and 0.550 respectively. This means of determining the fluorescent contribution FC appears to be successful.

The factor RK whereby the reflectance can be adjusted to account for misalignment or incorrect spacing seems to function better than was expected.

The following examples will serve to explain the calculations of the output data for the different filter positions in greater detail.

TABLE 6

Table Showing
Exemplary Calculation of Paper
Optical Parameter

Calculation of $R_o$, T, $R_{oo}$, FC and $R_{oo}$FC from OMOD data with the No. 1 filter in position.
Input: RSD1, RSP1, TSD1, TSP1, RSD7, RSP7, TK, RK, RSD4, RSP4, RD1, RD4, and GC1
Calculation:
RPD1 = (RD1 × RSP1 × RK)/RSD1
RPD4 = (RD4 × RSP4 × RK)/RSD4
RPD7 = (RD4 × RSP7 × RK)/RSD7
TPD/TD = (TSP1 × TK))/TSD1
$R_o$ = [RPD1 − (RD1(TPD/TD)$^2$)]/[RD1(TPD/TD)$^2$)]
T = [(TPD/TD)(1 − (RD1 × RPD1))]/[1 − (RD1(TPD)$^2$)]
A = (1 + $R_o^2$ − T$^2$)/$R_o$ $R_{oo}$ = (A/2) − $\sqrt{(A/2)^2 - 1}$
FC = 0.500 (RPD7 − RPD4)
$R_{oo}$FC = $R_{oo}$ + FC + GC1
Calculation of $R_o$, T, $R_{oo}$, FC and $R_{oo}$FC from OMOD data with the No. 2 filter in position
Input: RSD2, RSP2, TSD2, TSP2, RSD7, RSP7, TK, RK, RSD4, RSP4, RD2 and GC2.
Calculation:
RPD2 = (RD2 × RSP2 × RK)/RSD2
RPD4 = (RD4 × RSP4 × RK)/RSD4
RPD7 = (RD4 × RSP7 × RK)/RSD7
TPD/TD = (TSP2 × TK)/TSD2
$R_o$ = [RPD2 − (RD2(TPD/TD)$^2$)]/[1 − (RD2(TPD/TD)$^2$)]
T = [(TPD/TD)(1 − (RD2 × RPD2))]/[1 − (RD2(TPD/TD)$^2$)]
A = (1 + $R_o^2$ − T$^2$)/$R_o$ $R_{oo}$ = (A/2) − $\sqrt{(A/2)^2 - 1}$
FC = 0.600(RPD7 − RPD4)
$R_{oo}$FC = $R_{oo}$ + FC + GC2
Calculation of $R_o$, T, $R_{oo}$, FC and $R_{oo}$FC from OMOD data with the No. 3 filter in position
Input: RSD3, RSP3, TSD3, TSP3, TK, RK, RD3 and GC3
Calculation:
RPD3 = (RD3 × RSP3 × RK)/RSD3
TPD/TD = (TSP3 × TK)/TSD3
$R_o$ = [RPD3 − (RD3(TPD/TD)$^2$)]/[1 − (RD3(TPD/TD)$^2$)]
T = [(TPD/TD)(1 − (RD3 × RPD3))]/[1 − (RD3(TPD/TD)$^2$)]
A = (1 + $R_o^2$ − T$^2$)/$R_o$ $R_{oo}$ = (A/2) − $\sqrt{(A/2)^2 - 1}$
FC = 0.0
$R_{oo}$FC = $R_{oo}$ + FC + GC3
Note:
The calculations for Filters No. 5 and 6 are carried out in the same manner as for filter No.3 except that the appropriate filter data are employed. FC is made equal to zero for filters No. 3, 5 and 6 for all samples.
Calculation of $R_o$, T, $R_{oo}$, FC and $R_{oo}$FC from OMOD TABLE 6-continued Table Showing
Exemplary Calculation of Paper
Optical Parameter data with the No. 4 filter in position.
Input: RSD4, RSP4, TSD4, TSP4, RSD7, TK, RK, RD4 and GC4.
Calculation:
RPD4 = (RD4 × RSP4 × RK)/RSD4
RPD7 = (RD4 × RSP7 × RK)/RSD7
RPD/TD = (TSP4 × TK)/TSD4
$R_o$ = [RPD4 − (RD4(TPD/TD)$^2$)]/[1 − (RD4(TPD/TD)$^2$)]
T = [(TPD/TD)(1 − (RD4 × RPD4))]/[1 − (RD4(TPD/TD)$^2$)]
A = (1 + $R_o^2$ − T$^2$)/$R_o$ $R_{oo}$ = (A/2) − $\sqrt{(A/2)^2 - 1}$
FC = 0.550(RPD7 − RPD4)
$R_{oo}$FC = $R_{oo}$ + FC + GC4

On the basis of further experimental data, the factors relating the fluorescent component, as measured on the monitoring device, to the fluorescent component as measured with the standard automatic color-brightness tester, have the following presently preferred values for filter wheel position numbers 1, 2 and 4: 0.528, 0.636, and 0.456, respectively.

DISCUSSION OF THE ON-MACHINE SYSTEM OF FIGS. 1-6

Set Up Procedure For the System of FIGS. 1-6

In the prototype system, potentiometers were included as part of the gain control resistance means and were adjusted for the respective positions of the filter wheel 210 to give values correlated directly with absolute reflectance and transmittance of the diffusing glass, such as given in the foregoing Table 1. In the preferred system of FIGS. 1-6, however, these potentiometers for adjusting amplifier gain are omitted and are replaced with fixed resistors 371-377 and 431-437 selected to give scale readings from meter 330 in the respective filter wheel positions which are well above the values given in Table 1. The higher gain values selected for the amplifiers 361 and 429 in the preferred system are intended to provide improved stability and increased sensitivity of measurement.

The upper and lower sensing heads are placed at a spacing of 3/16 inch by means of a gauging plate made of 3/16 inch Teflon. The incident beam 133 forms a light spot of elliptical configuration on the planar upper and surface 98 of the diffusing window 135. The major axis of the elliptical light spot has a length of about ⅝ inch and is parallel to the direction of web movement, i.e. the machine direction, while the minor axis has a length of about ⅜ inch and is at right angles to the machine direction. The reflected beam 137 consists of the total light reflected from a circular spot of approximately ⅜ inch diameter. This viewed area lies substantially within the elliptical illuminated area on surface 98; however, the two essentially coincide in the direction of the minor axis of the illuminated spot.

Since the effective optical aperture 154, FIG. 3, of the lower sensing head is of a diameter of about 15/16 inch, the system will be insensitive to a certain amount of lateral offset between the optical axis 15 of the upper sensing head and the optical axis 515 of the lower sensing head.

In setting up the system, the position of the lower sensing head may be adjusted laterally so that the spot formed by the incident beam 133 is essentially centered on the surface 98 of window 135.

The optimum relationship between the upper and lower sensing heads can be precisely detected by observing the reflectance output from the upper sensing head (in any position of the filter wheel 210) as the heads are moved relative to one another while maintaining the spacing of 3/16 inch between the heads. When the correct geometrical relationship is attained between the incident beam 133, the reflected beam path 137 and the plane of the surface 98 of the window 135, the reflectance signal will have a maximum value.

With the upper and lower sensing heads in the optimum geometric relationship, and with the incident beam impinging on the central part of surface 98, it is considered that relative shifting between the upper and lower heads in the plane of surface 98 over a range of plus or minus $\frac{1}{8}$ inch in any lateral direction should have an insignificant effect because of the flat planar configuration of surface 98.

Direct Digital Control Analog Point Scan Subroutine of FIG. 7

The program subroutine of FIG. 7 accepts digital information from the analog to digital converters of component 501, FIG. 6, at one second intervals. Referring to FIG. 7 where the blocks containing the flow chart steps are individually numbered in their operational sequence, the step 701 represents the entry into the subroutine at one second intervals. Step 702 shows the acceptance of an analog input and conversion to engineering units. Step 703 indicates saving such converted input as a process variable in a scan only file of the digital control computer. A type of control computer which has utilized such a scan program for a number of years for collecting data in an overall paper machine direct digital control system is the General Electric Company PAC 4020 Process Control Computer. Minor additions to the existing program routine will allow for the collection of the reflectance and transmittance data by means of the existing computer system. A suitable computer interface between monitoring device 10 and such a control computer has been described previously. Block 702 suggests that valid reflectance and transmittance values might be limited to a range from 0 to 1.0 units, for example. In this event the program could include provision for checking that the collected reflectance and transmittance values were within the range and for printing out a message or the like if invalid data is received.

Block 704 indicates the sequential reading of process data input points in a predetermined order until the last data input point has been scanned, whereupon the computer exits from the subroutine.

Process File (FILE X) for the Data Acquisition and Data Reduction Programs

The arrangement of FILE X which is utilized during acquisition of data from the system of FIGS. 1-6 and conversion thereof to desired output paper optical quantities can be visualized from the following Table 7. In the first column of Table 7, sequential memory locations of the process file have been assigned sequential numbers beginning with zero. A convenient label has been assigned to certain groups of sequential memory locations, and this is also given in the first column. (The term FILE X is used to designate all of the locations zero through one hundred forty while subsequent labels refer to only the subadjacent group of sixteen locations or less.)

In general the significance of the various stored data will be apparent from the descriptions given in the righthand column of Table 7 and from the use of the stored data as indicated by the flow charts of FIGS. 8-20.

TABLE 7

FILE X (Process File For the Data Acquisition and Data Reduction Programs

| Label and Relative Location of File | Description of Stored Data |
|---|---|
| FILE X | |
| 0 | STATUS |
| 1 | PCW ADR LOOP P (REFLECTION CELL) |
| 2 | PCW ADR LOOP Q (TRANSMISSION CELL) |
| 3 | PFA GAGE HEAD POSITION (TAG 129) |
| 4 | SLOW DOWN COUNT |
| 5 | SLOW DOWN INITIAL VALUE COUNT |
| 6 | FILTER WHEEL POSITION INDEX EST. (I) |
| 7 | PFA BASIS WEIGHT AVG. (TAG. BOO) |
| 8 | MINIMUM ON SHEET HEAD POS. |
| 9 | INITIALIZATION INDEX (K) |
| 10 | FILTER WHEEL CYCLE COMPLETION INDEX (CYCLE) |
| 11 | SMOOTHING CONSTANT (ALPHA) |
| CTABL | |
| 12 (0,0) | STANDARDIZATION CORR. FACTOR, CTABLE=(C) |
| 13 (1,0) | |
| 14 (2,0) | |
| 15 (3,0) | |
| 16 (4,0) | |
| 17 (5,0) | |
| 18 (6,0) | |
| 19 (7,0) | SPARE |
| 20 (0,1) | |
| 21 (1,1) | |
| 22 (2,1) | |
| 23 (3,1) | |
| 24 (4,1) | |
| 25 (5,1) | |
| 26 (6,1) | |
| 27 (7,1) | SPARE |
| STTABL | |
| 28 (0,0) | STANDARDIZATION INPUT DATUM, ST=(R*) |
| 29 (1,0) | |
| 30 (2,0) | |
| 31 (3,0) | |
| 32 (4,0) | |
| 33 (5,0) | |
| 34 (6,0) | |
| 35 (7,0) | SPARE |
| 36 (0,1) | ,″ = (T*) |
| 37 (1,1) | |
| 38 (2,1) | |
| 39 (3,1) | |
| 40 (4,1) | |
| 41 (5,1) | |
| 42 (6,1) | |
| 43 (7,1) | SPARE |
| RGTABL | |
| 44 (0,0) | NOMINAL BACKING REFLECT., RG = (Rg) |
| 45 (1,0) | |
| 46 (2,0) | |
| 47 (3,0) | |
| 48 (4,0) | |
| 49 (5,0) | |
| 50 (6,0) | |
| 51 (7,0) | SPARE |
| 52 (0,1) | NOMINAL DIFFUSER TRANS. ″ =(Td) |
| 53 (1,1) | |
| 54 (2,1) | |
| 55 (3,1) | |
| 56 (4,1) | |
| 57 (5,1) | |

TABLE 7-continued
FILE X (Process File For the Data Acquisition and Data Reduction Programs)

| Label and Relative Location of File | Description of Stored Data | |
|---|---|---|
| 58 (6,1) | | |
| 59 (7,1) | SPARE | |
| VTABL | | |
| 60 (0,0) | CORRECTED & SMOOTHED INPUT NFCELL=R | |
| 61 (1,0) | | |
| 62 (2,0) | | |
| 63 (3,0) | | |
| 64 (4,0) | | |
| 65 (5,0) | | |
| 66 (6,0) | | |
| 67 (7,0) | SPARE | |
| 68 (0,1) | " = TDP | |
| 69 (1,1) | | |
| 70 (2,1) | | |
| 71 (3,1) | | |
| 72 (4,1) | | |
| 72 (5,1) | | |
| 74 (6,1) | | |
| 75 (7,1) | SPARE | |
| SGTABL | | |
| 76 (0,0) | REFLECTANCE SPECIFIC GRADE CORR., SGCF | |
| 77 (1,0) | | |
| 78 (2,0) | | |
| 79 (3,0) | | |
| 80 (4,0) | | |
| 81 (5,0) | | |
| 82 (6,0) | | |
| 83 (7,0) | SPARE | |
| 84 (0,1) | TRANSMITTANCE SPECIFIC GRADE CORR. | |
| 85 (1,1) | | |
| 86 (2,1) | | |
| 87 (3,1) | | |
| 88 (4,1) | | |
| 89 (5,1) | | |
| 90 (6,1) | | |
| 91 (7,1) | SPARE | |
| OUTABL | | |
| 92 (0) | PRINTING OPACITY | (POPAC) |
| | Y REFL=ILLUM.A-.89 BACKING | (YAR89) |
| 94 (2) | TAPPI OPACITY | (TOPAC) |
| 95 (3) | X-TRI . STIMULUS | (XTRI) |
| 96 (4) | Y-TRISTIMULUS | (YTRI) |
| 97 (5) | Z . TRISTIMULUS | (ZTRI) |
| 98 (6) | HUNTER L | (LH) |
| 99 (7) | HUNTER A | (AH) |
| 100 (8) | HUNTER B | (BH) |
| 101 (9) | BRIGHTNESS WITH FLUOR. & INF BACKING | (BRRINF) |
| STABL | | |
| 102 (0) | SCATTER COEFFICIENT | (S) |
| 103 (1) | | |
| 104 (2) | | |
| 105 (3) | | |
| 106 (4) | | |
| 107 (5) | | |
| 108 (6) | | |
| 109 (7) | SPARE | |
| KTABL | | |
| 110 (0) | ABSORPTION COEFFICIENT | (K) |
| 111 (2) | | |
| 113 (3) | | |
| 114 (4) | | |
| 115 (5) | | |
| 116 (6) | | |
| 117 (7) | SPARE | |
| RSTABL | | |
| 118 (0,0) | STANDARDIZATION BACKING REFL REFERENCE (Rs) | |
| 119 (1,0) | | |
| 120 (2,0) | | |
| 121 (3,0) | | |
| 122 (4,0) | | |
| 123 (5,0) | | |
| 124 (6,0) | | |
| 125 (7,0) | SPARE | |
| 126 (0,1) | STANDARIZATION DIFFUS. TRANS. REFERENCE (Ts) | |
| 127 (1,1) | | |
| 128 (2,1) | | |
| 129 (3,1) | | |
| 130 (4,1) | | |
| 131 (5,1) | | |
| 132 (6,1) | | |
| 133 (7,1) | SPARE | |
| MPAR | | |
| 134 (0) | FLUOR SLOPE EMPIRICAL CONSTANT | |
| 135 (1) | $X_b$-FLUOR/Z-FLUOR. RATIO | FCON |
| 136 (2) | $B_r$-FLUOR/Z-FLUOR RATIO | FCON |
| 137 (3) | RESET VALUE OF FILTER CYCLE INDEX | ICYCLE |
| 138 (4) | BASIS WT AVG. (FLOATING POINT) | BW |
| 139 (5) | EMPIRICAL OVERALL REFL. CORR. FACTOR | CORR |
| 140 (6) | EMPIRICAL OVERALL TRANS. CORR. FACTOR | CORR |

In referring to locations of FILE X in the program flow charts of FIGS. 8-20, the relative location of FILE X is indicated by the number in parenthesis. Thus FILE X(4) refers to relative location number four of FILE X as given in Table 7. File X(138) corresponds to MPAR(4) in Table 7, and both refer to relative location number one hundred and thirty eight. FILE X(four) is an alternative to FILE X(4), and is used in the text to avoid any possible confusion with drawing reference numerals.

The following general discussion of successive locations or groups of locations of FILE X, taken in numerical order, will serve as an introduction of the description of the program routines of FIGS. 8-20. Contemplated modifications of the programs and of FILE X will be discussed in a later section.

In location O of FILE X, the Status word includes a bit number 23 which is set to a logical one when conditions are met for making standardizing calculations. For example, the OMOD should be off sheet and the beta gauge with which the OMOD is mounted for scanning movement should be in its standardizing mode. The set condition of bit 23 is responded to by the program to bypass data smoothing and to store data in a special table STTABLE at locations 28-34 and 36-42 of Table 7. The condition of bit 23 is reset to logical zero when the filter wheel has indexed through seven positions or if the beta gauge completes standardization before the complete set of OMOD standardization data is collected.

Locations 1 and 2 of FILE X may store the PCW (process control word) addresses for Loops P and Q. Loop P is a subroutine for controlling the processing of reflectance data and Loop Q is concerned with the processing of transmittance data. These loops begin at FIG. 13 of Program Fourteen.

Location three of FILE X, contains the address of the DDC scanner file containing the position of the sensing head 10 along its path of traverse of the web. This position is monitored by the Scan-Only (DDC) routine of FIG. 7 and is stored in the scan system file identified by TAG one hundred twenty nine. A current value of sensing head position is transferred from the referenced DDC file into location three of FILE X periodically.

Location four of FILE X stores a SLOWDOWN COUNT index value which is used to cause a specified number of dummy readings at each filter wheel position to be made after each advance of the filter wheel to allow time for the OMOD electronics to reach steady state, and to allow for any transient error in synchronization between the DDC Scan-Only routine of FIG. 7 and the Data Reduction routine (Program Fourteen) of FIGS. 8-16 which runs at one second intervals under the control of the RTMOS Scheduler (a computer real time operating system of the General Electric Co.).

Location five of FILE X stores a SLOWDOWN INITIAL VALUE COUNT which is used when a processing cycle is being initiated.

Location six of FILE X of Table 7 stores an index value I which represents the estimated filter wheel position, based on the number of actuations of the filter wheel indexing solenoid, since the initial filter wheel position wherein reed switch 358, FIG. 6, is closed in response to the proximity of permanent magnet 243, FIGS. 3 and 6. In the computer program, the successive filter wheel positions are designated 0, 1, 2, 3, 4, 5 and 6, and result in spectral response distributions designated $B_R$ (brightness), $X_B$ (blue portion of the $E_c\bar{x}$ function), $X_R$ (red portion of the $E_c\bar{x}$ function), Z ($E_c\bar{z}$ function without fluorescence), $Y_C$ ($E_c\bar{y}$ function), $Y_a$($E_a\bar{y}$ function), and $Z_{FL}$($E_c\bar{z}$ function, with fluorescence).

Location seven of FILE X serves to store the address of the DDC file for basis weight average. TAG BOO, which is used by Program Fourteen to access the basis weight data and store it in location MPAR (4) in floating point format. This will be used by Program Forty-Two during the reduction of data.

Location eight of FILE X stores a value for the minimum on-sheet head position. When the head position is less than such minimum value, a standardization cycle may be set in motion by Program Fourteen.

Location nine of FILE X contains the value of an initialization index K which is used to determine when all seven smoothed input values have been initialized to equal the latest unsmoothed input for each of the reflectance and transmittance channels.

Location ten of FILE X stores a filter wheel cycle completion index designated CYCLE that can be used to determine when a specified number of filter wheel cycles have been completed through the last filter wheel position (position six in the programming notation). This prevents the data reduction program (Program Forty-Two) of FIGS. 17-20 from running until a specified number of data sets have been collected since the last time it ran or the unit was standardized.

Figure 14:
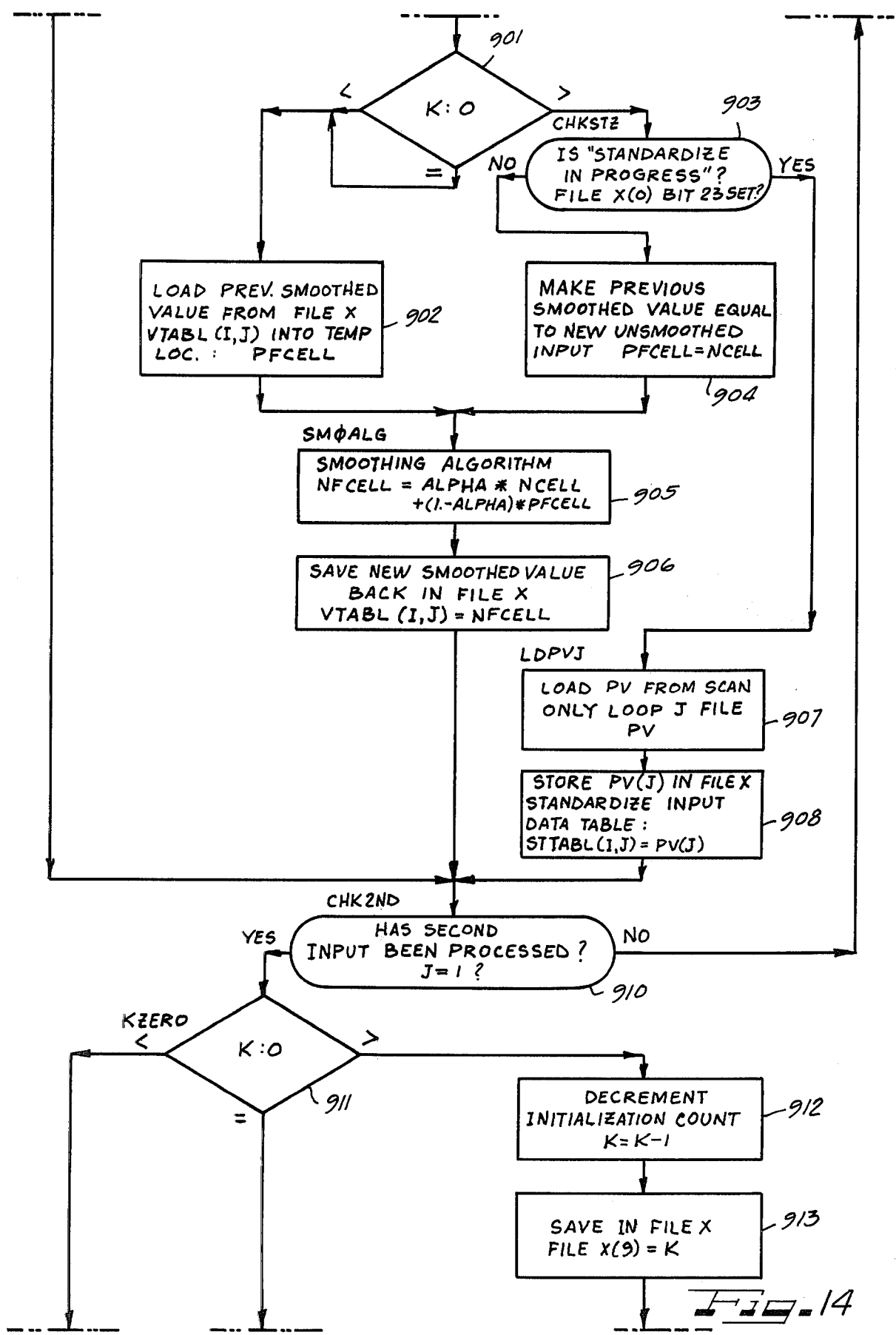

Location eleven of FILE X stores a smoothing constant ALPHA which is used in smoothing the input data from FIGS. 1-6 by Program Fourteen, as indicated in FIG. 14.

A temporary location index J is used to point to either the reflectance vector tables or the transmittance vector tables. J is equal to zero to indicate reflectance, and is equal to one to designate transmittance. Each of the tables such as CTABL of table 7 has a first set of locations (e.g. 12 through 18) which can become active while J is equal to zero and a second set of locations (e.g. 20 through 26) which can be selected when J is equal to one. Thus the sets of two numerals in parenthesis at locations 12 through 133 represent respectively the value of the filter wheel position index I and the J index value corresponding to the location.

The table CTABL at locations 12-18 and 20-26 of the process file of Table 7 is used to store a standardization correction factor C. The reflection values of the factor C for the respective filter wheel positions are stored in locations 12-18 and are active when J=0, and I=0, 1, 2, 3, 4, 5 and 6, respectively. Similarly the transmission values for the lower sensing head and the respective filter wheel positions are stored in locations 20-26, which are selected when J=1 and I=0, 1, 2, 3, 4, 5 and 6, respectively.

The table ST TABL, stores data from the OMOD system of FIGS. 1-6 in the standardization mode with the heads in the off-sheet position.

The table RG TABL stores the value RG, the nominal reflectance of the backing for the web in the off-sheet position, for the respective filter wheel positions, and also the value TD, the nominal transmittance of the diffusing window 135 in the off-sheet position. These values may be experimentally determined as previously explained and inserted into table RG TABL at start up of the system.

Table VTABL serves to store input data after it has been processed by Program Fourteen of FIGS. 8-16. The raw data is corrected on the basis of the most recent standardization values from table ST TABL and, multiplied by the correction factors C from table CTABL, and exponentially smoothed by means of the subroutine of FIG. 14 before being stored in the VTABL locations.

The SG TABL table of the process file of Table 7 stores the specific grade correction factors SGCF.

The OUTABL locations store the output quantities as computed under the control of the Data Reduction Program Forty Two of FIGS. 17-20.

The tables STABL and KTABL store the scatter coefficient S and the absorption coefficient K which together serve to characterize the paper web being monitored.

Optical Property Data Acquisition Subroutine of FIGS. 8-16 (Program Fourteen)

The subroutine of FIGS. 8-16 is referred to as Program Fourteen (or Program 14) and is designed to perform various data acquisition functions as indicated in the flow chart.

It is believed that the flow chart of FIGS. 8-16 will be self-explanatory given the foregoing comments concerning Table 7. The following Tables 8-16 are a tabulation of the blocks of the subroutine with supplementary comments to indicate the meaning of any abbreviations, or to paraphrase any possibly cryptic statements. (Arabic numerals within the blocks in FIGS. 8-20 do not refer to reference numerals of FIGS. 1-6. This is indicated in the following tabulation by spelling of such numerals so far as feasible.)

TABLE 8

Supplementary Explaination of the Program Steps of FIG. 8

| Program Step | Comment |
|---|---|
| 801 | Program Fourteen initial point at start up. |
| 802 | The timer location designated AUXTUM +3 receives an intial value. (Equal to the present time). |
| 803 | The point of entry each time the timer location AUX-TIME reaches a value L, i.e. every one second. |
| 804 | Load the starting address of File X into index register three. |
| 805 | Load PCW (process control word) addresses of loops P and Q from lacations one and two of FILE X. (See Table 7.) |
| 806 | Are scan bits in both of the process control words referred to in block 805 set for off-scan? |
| 807 | If decision at block 806 is no, calculate the next time for Program Fourteen to run DLYTIM (delay time) seconds from the present time. (The value of DLYTIM is nominally one second.) Add DLYTIM to the present value of AUXTIM+3 to register a new time AUXTIM+3. |
| 808 | Load value of SLOWDOWN COUNT from location four of FILE X into the temporary register SLODWN. |
| 809 | Decrement the count in SLODWN by one. |
| 810 | If answer to decision of block 806 is yes, turn Program Fourteen off and exit from the program. |

TABLE 9

Figure 9:
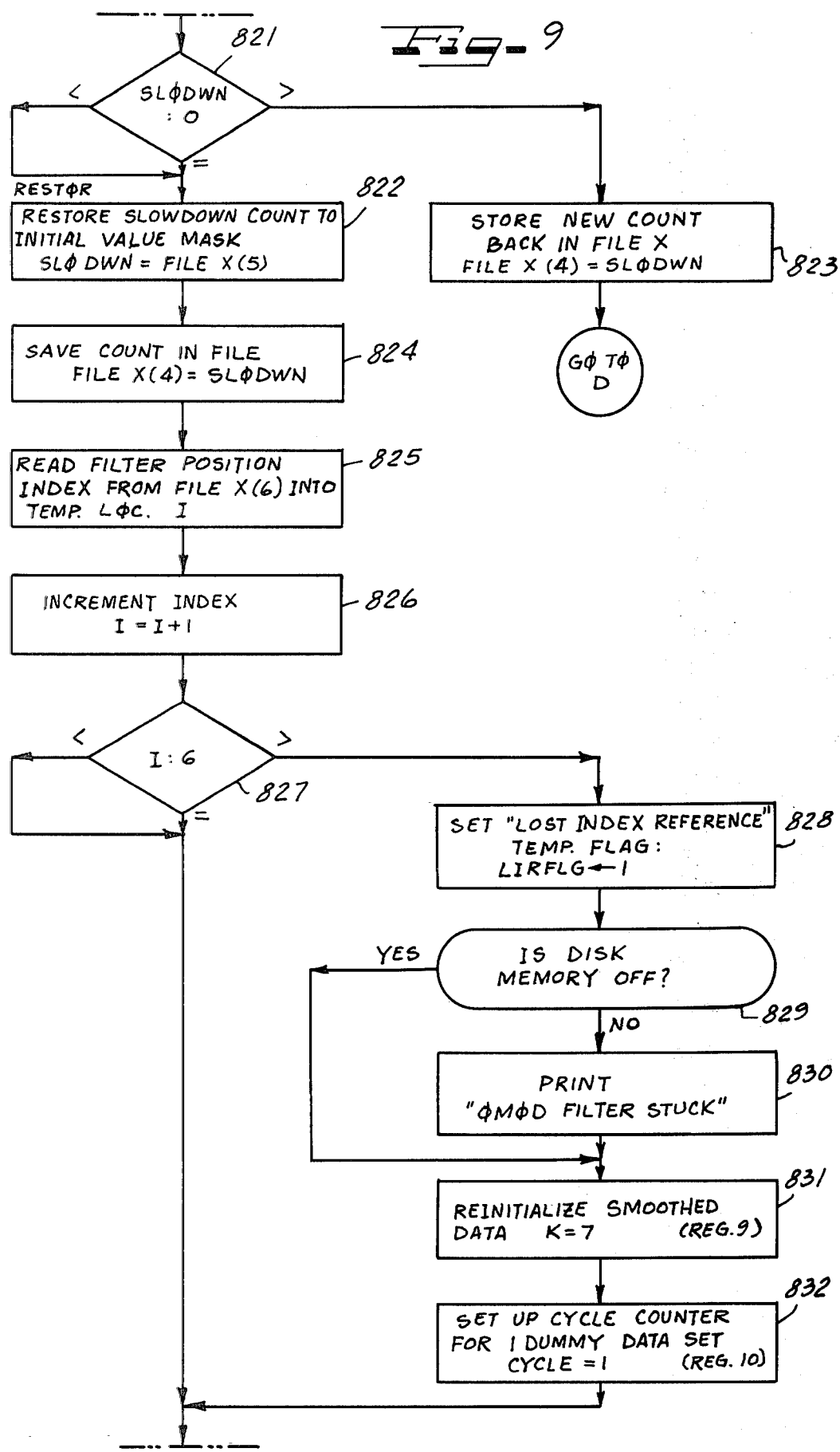

Supplementary Explanation of the Program Steps of FIG. 9

Figure 10:
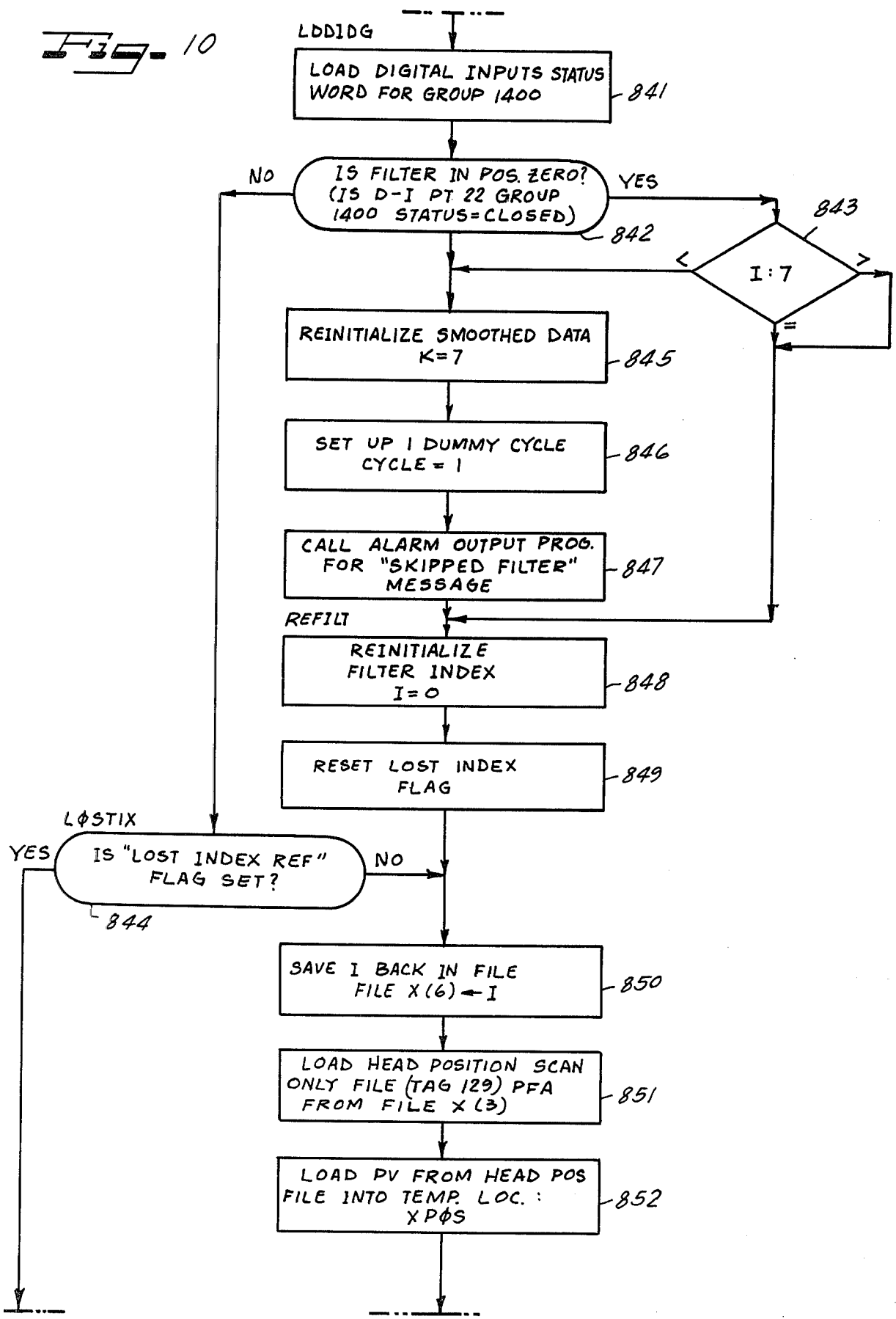
Figure 16:
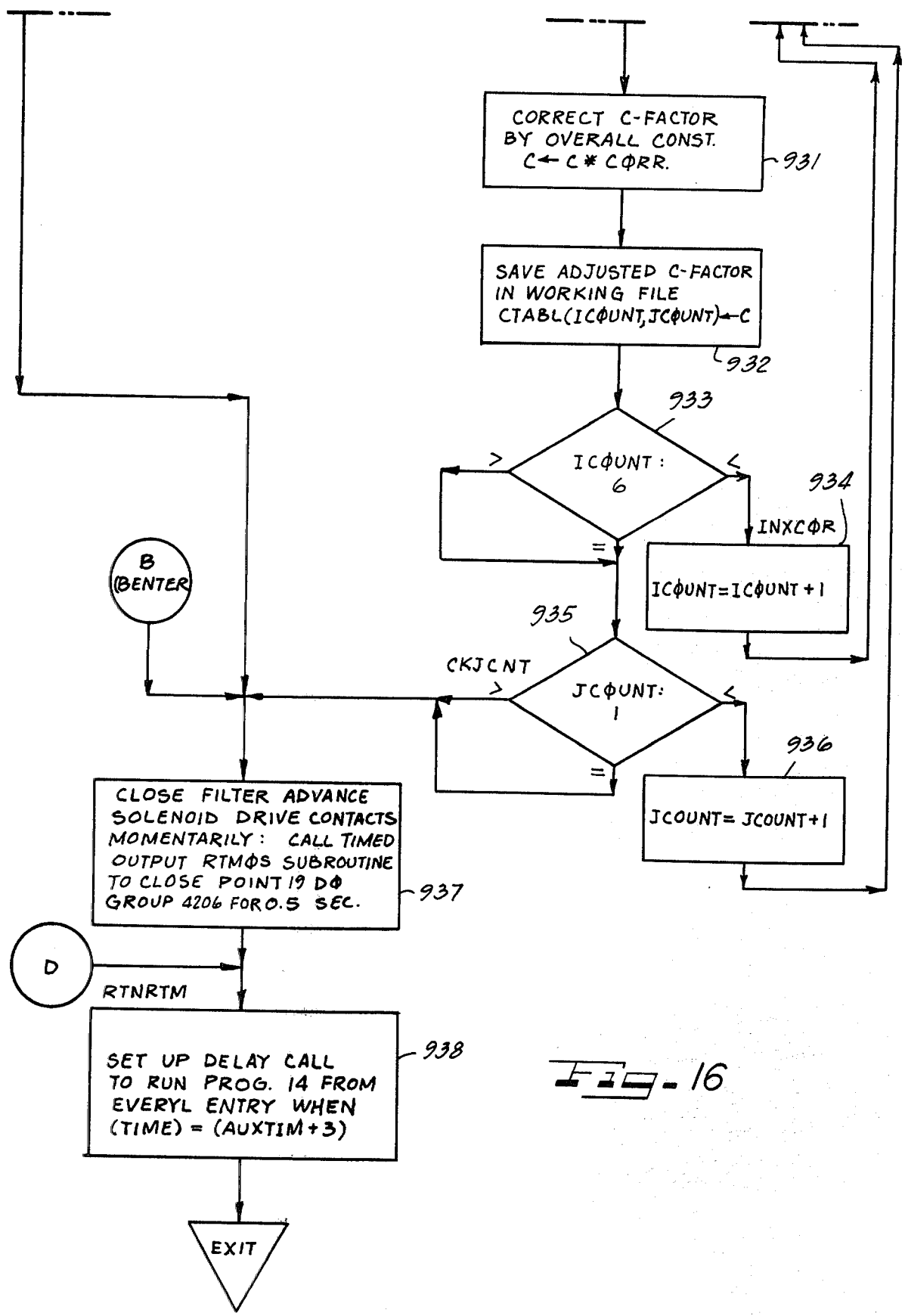

| Program Step | Comment |
|---|---|
| 821 | Compare the count value in SLODWN with zero, if SLODWN is equal to or less than xero, go to block 822, if SLODWN is greater than zero, go to block 823. |
| 822 | Insert SLOW DOWN INITIAL VALUE COUNT from File X(five) into the SLODWN register. |
| 823 | Store the decremented count value in SLODWN in SLOW DOWN COUNT at FILE X(four), and go to point D of the program, shown in FIG. 16. |
| 824 | Place the count transferred from FILE X(five) at block 822 into FILE X(four) labeled SLOW DOWN COUNT. |
| 825 | Read content of FILE X(six) into temporary location I. |
| 826 | Add one to temporary location 1. |
| 827 | Compare I and six; if I equal to or less than six, go to LDDIDG, block 841 of FIG. 10; if I is greater than six, go to block 828. |
| 828 | Put a one in temporary flag location LIRFLG. |
| 829,830 | If disk memory is operating print out that the indicated message. |
| 831 | Set the K value in location nine of FILE X to seven. |
| 832 | Set CYCLE value in location ten of FILE X to one, and go to LDDIDG, block 841, FIG. 10. |

TABLE 10

Supplementary Explanation of the Program Steps of FIG. 10

| Program Step | Comment |
|---|---|
| 841 | Load the contents of the memory location that indentifies the status of the digital input group (Group 1400) to which the zero position filter contacts 358, FIG. 6, are connected. |
| 842 | Is the filter wheel in position zero, i.e. the position shown in FIG. 3? This is determined from bit position twenty-two of the STATUS word loaded in step 841. If bit position twenty-two indicates that the contacts of reed switch 358, FIG. 6, are closed, then go to block 843. If the contacts are open, go to LOSTIX, block 844. |
| 843 | If value in temporary location I is less than seven, go to block 845. If I is equal to or greater than seven go to REFILT, block 848. |
| 844 | Is a value one in the temporary flag location LIRFLG? (See block 828, FIG. 9.) |
| 845 | Set FILE X (nine) to seven. |
| 846 | Set FILE X (ten) to one. |
| 847 | If the filter wheel is indexing properly, the I value will be incremented by the step of block 826, FIG. 9, so that I will equal seven at block 843. Since I was less than seven, apparently the filter wheel has failed to index each time it was commanded to do so. Block 847 provides for the print out by means of an alarm output program under these conditions. |
| 848 | Set location six of FILE X to zero. |
| 849 | Set LIRFLG to zero. |
| 850 | Insert current value of I in FILE X (six). |
| 851 | Load the head traverse position File Address from FILE X(three). |
| 852 | Load the process variable (PV) of block 851 into the temporary location XPOS. |

TABLE 11

Figure 11:
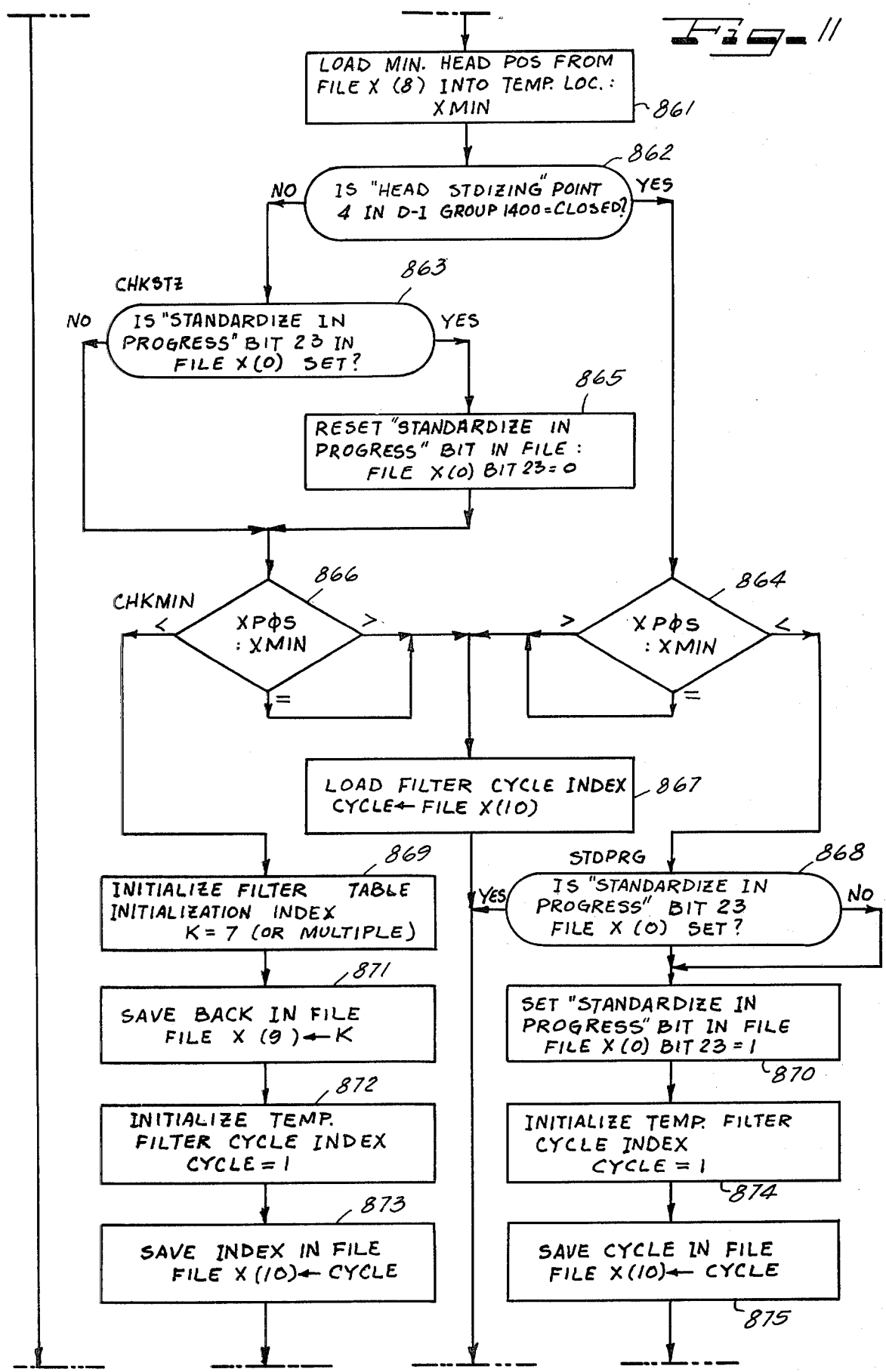

Supplementary Explanation of the Program Steps of FIG. 11

| Program Step | Comment |
|---|---|
| 861 | Load the content of FILE X(eight) into the temporary location XMIN. |
| 862 | Is the beta gauge in a standardizing mode as indicated by point four in the digital input status word for group fourteen hundred?. Point four refers to the bit four position of the status word. If the beta gauge is not in standardizing mode, go to block 864. |
| 863 | Is the OMOD shown to be in standardizing mode by bit position twenty three of FILE X (zero). If the OMOD is being standardized, go to block 865. If standardization is not in progress go to block 866. |
| 864 | Compare the value of XPOS(See block 852 FIG. 10) with the value of XMIN See block 861). If XPOS is equal to or greater than XMIN, go to block 867. If XPOS is less than XMIN, go to block 868. |
| 865 | Reset bit position twenty three of FILE X(zero) to zero. |
| 866 | Compare XPOS and XMIN. |
| 867 | Load content of FILE X(ten) into the temporary register CYCLE. |
| 868 | Is bit position twenty three of FILE |

TABLE 11-continued

Supplementary Explanation of the Program Steps of FIG. 11

Figure 12:
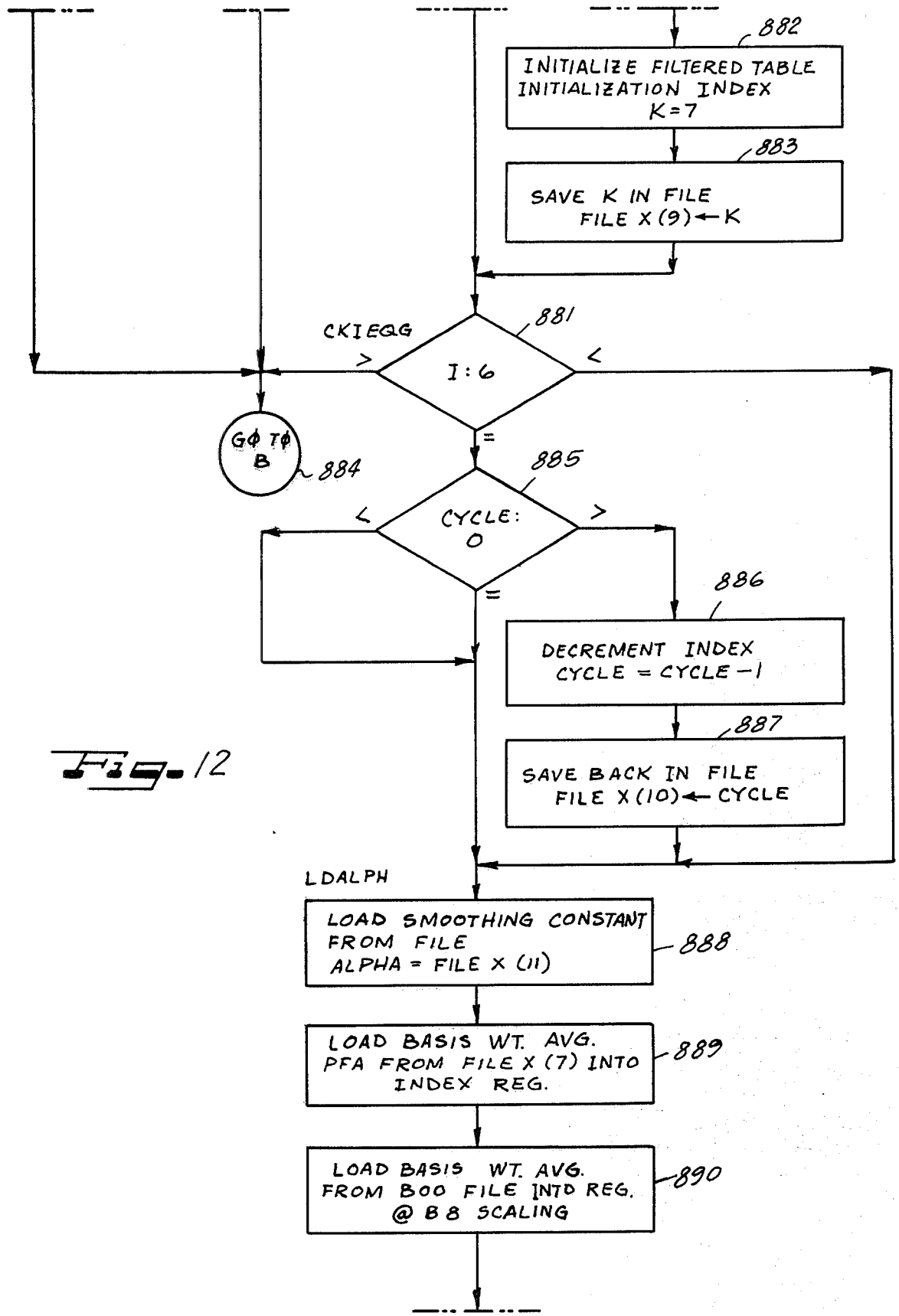

| Program Step | Comment |
|---|---|
| | X(zero set? If yes, go to comparison block 881, FIG. 12. If not, proceed with standardization beginning at block 870. |
| 869 | Set temporary register K to seven or a multiple of seven. |
| 870 | Set bit position twenty three of FILE X(zero) to the logical one state. |
| 871 | Put the value of K (see block 869) into FILE X(nine). |
| 872 | Set temporary register CYCLE to logical one state. |
| 873 | Place content of CYCLE in FILE X (ten). |
| 874 | Same as block 872. |
| 875 | Same as block 873. |

TABLE 12

Supplementary Explanation of the Program Steps of FIG. 12

| Program Step | Comment |
|---|---|
| 881 | Compare value in temporary register I with six. |
| 882 | Continuation from block 875, FIG. 11. Same comment as for block 869. |
| 883 | Same as block 871. |
| 884 | Go to BENTER location, FIG. 16, after an affirmative decision at block 844, FIG. 10; or after execution of step 873, FIG. 11; or if I is greater than six at block 881. |
| 885 | Compare CYCLE and zero. |
| 886 | Decrement CYCLE by one if CYCLE was greater than one at block 885. |
| 887 | Same as 873. |
| 888 | Load content of FILE X(eleven) into temporary register ALPHA. |
| 889 | Load content of FILE X(seven) into the index register (BOO File Address) |
| 890 | Load BOO process variable into A-register with fixed point scaling of B8 |

TABLE 13

Figure 13:
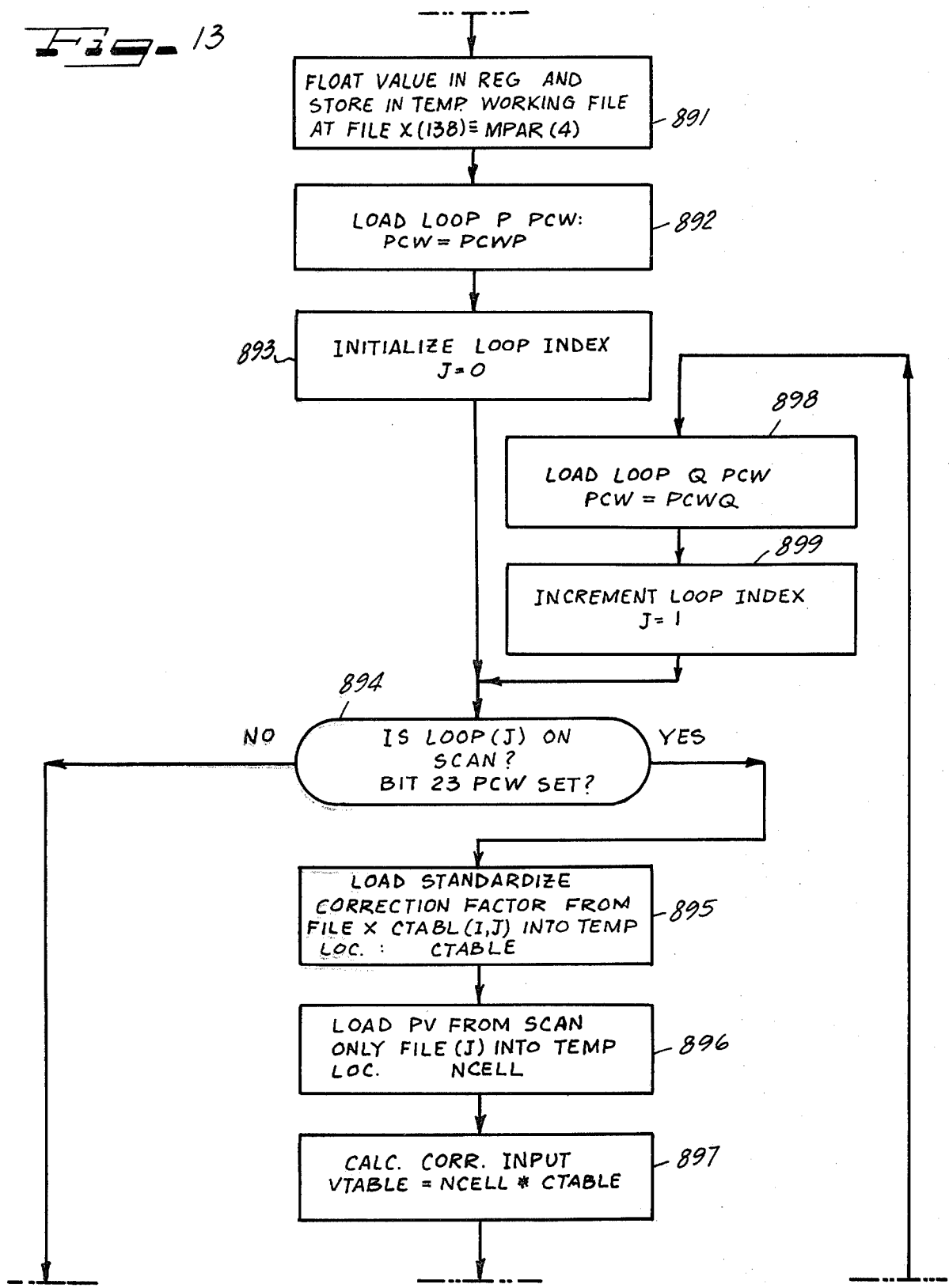

Supplementary Explanation of the Program Steps of Fig. 13

| Program Step | Comment |
|---|---|
| 891 | Convert content at B8 SCALING (See block 890, FIG. 12) to floating point notation and store converted value in FILE X(one hundred thirty eight), which is also designated MPAR, location four in Table 7. |
| 892 | Load the process control word PCWP at the address given at FILE X(one) into the register PCW. |
| 893 | Set register J to zero. |
| 894 | Is bit position twenty three of the process control word (PCW) of LOOP (J) set? If not, go to block 910, FIG. 14. If yes, go to block 895. |
| 895 | Load the content of CTABL of FILE X for the location corresponding to the current values of I and J into temporary location CTABLE. |
| 896 | Load the process variable (PV) from the Scan Only File PF(J) into the temporary location NCELL. |
| 897 | Calculate the corrected input value by multiplying the content of NCELL by the content of CTABLE, and store in |

TABLE 13-continued

Supplementary Explanation of the Program Steps of Fig. 13

| Program Step | Comment |
|---|---|
| | the table VTABLE of FILE X(See Table 14) in the location corresponding to current values of I and J. Go to block 901, FIG. 14. |
| 898 | After a negative decision at block 910, FIG. 14, the loop P subroutine is initiated by loading the process control word PCWQ whose address is given at FILE X(two) into the temporary register PCW. |
| 899 | Increment the value stored in location J to one. |

TABLE 14

Supplementary Explanation of the Program Steps of FIG. 14

| Program Step | Comment |
|---|---|
| 901 | Compare the value in temporary location K with zero. If K is equal to or less than zero, go to block 902. If K is greater than zero, go to CHKSTZ, block 903. |
| 902 | Load content of current location of VTABL (I,J) from FILE X into the temporary location PFCELL. |
| 903 | Is bit twenty three of the status word in FILE X (zero) set |
| 904 | Transfer content of NCELL (see block 896, FIG. 13) into the temporary location PFCELL. |
| 905 | Apply the smoothing algorithm by calculating the sum of ALPHA times NCELL and (one minus ALPHA) times PFCELL, and store the result in NFCELL. |
| 906 | Transfer the content of NFCELL to the appropriate location of VTABL (I,J) in FILE X. (See Table 7.) |
| 907 | Load the PV from Scan Only LOOP J, i.e. Process FILE PF (J) into temporary register PV (J). |
| 908 | Store the content of PF (J) in table STTABL (I,J) of FILE X at a location corresponding to the current values of I and J. See Table 7. |
| 910 | Has loop Q been processed? If not, enter loop Q at block 898, FIG. 13. If the content of temporary location J is equal to one, go to block 911. |
| 911 | Compare the content of temporary location K with zero. If K is less than zero, go to the B entry location BENTER, FIG. 16. If K equals zero, go to block 921, FIG.15. If K is greater than zero, go to block 912. |
| 912 | Decrement the count in K by one. |
| 913 | Store the content of K in FILE X(nine). Go to BENTER location in FIG. 16. |

TABLE 15

Figure 15:
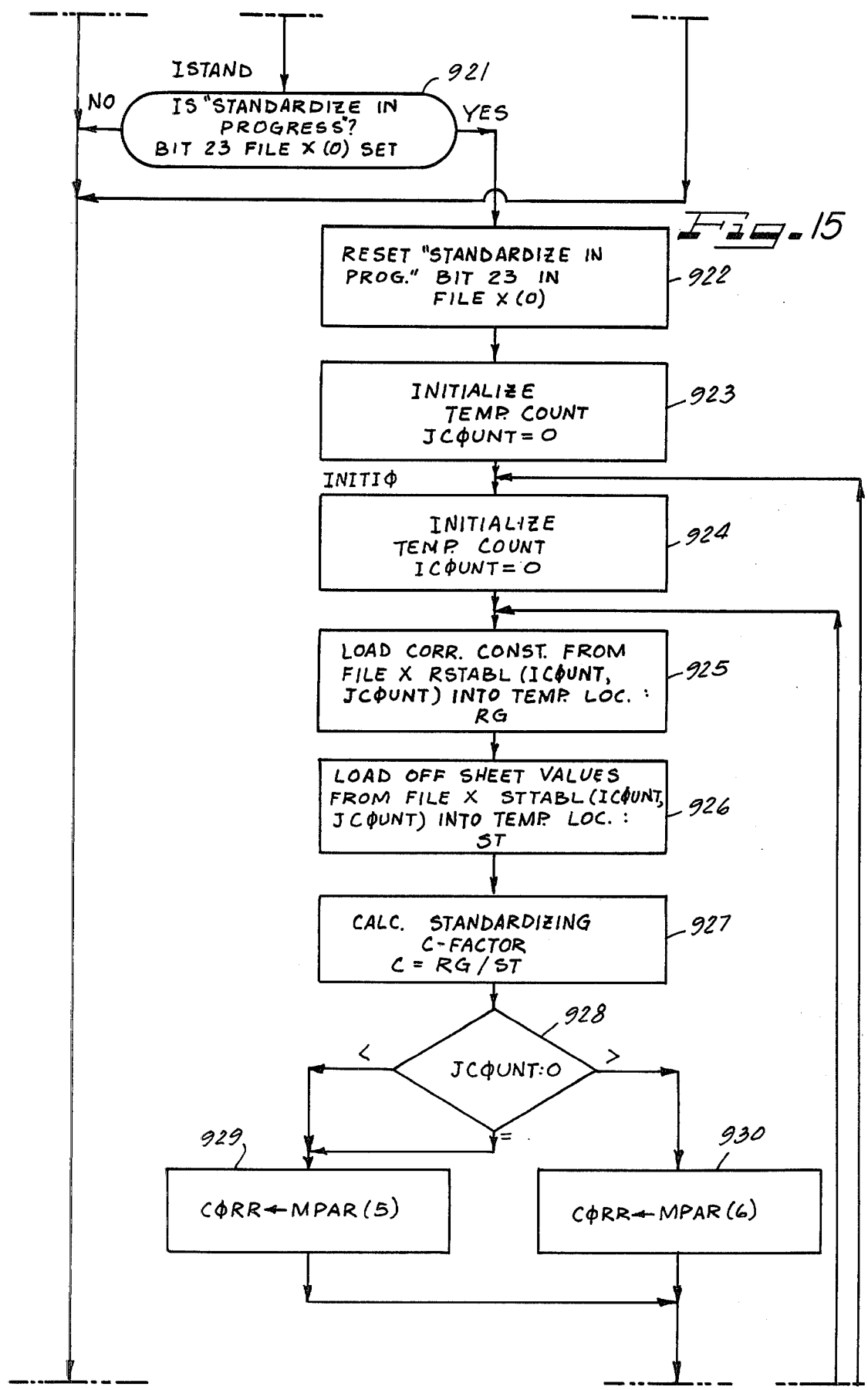

Supplementary Explanation of the Program Steps of FIG. 15

| Program Step | Comment |
|---|---|
| 921 | Is bit position twenty three of the STATUS word from FILE X(zero) set? If not, go to BENTER location of FIG. 16. If affirmative, go to block 922. |
| 922 | Reset bit position twenty three of FILE X(zero). |
| 923 | Set temporary register J COUNT to zero. |

TABLE 15-continued
Supplementary Explanation of the Program Steps of FIG. 15

| Program Step | Comment |
|---|---|
| 924 | Set temporary register I COUNT to zero. |
| 925 | Load the correction constant from the appropriate location of RSTABL, Table 7, into the temporary location RG. |
| 926 | Load the standardization value from the appropriate location of STTABL, Table 7, into the temporary location ST. |
| 927 | Calculate the standardizing C factor by dividing RG by ST and store in temporary location C. |
| 928 | If J COUNT is less than or equal to zero, go to block 929; otherwise go to block 930. |
| 929 | Transfer the value stored at FILE X (one hundred thirty nine) to temporary location CORR. |
| 930 | Transfer the value stored at FILE X (one hundred forty) to temporary location CORR. |

TABLE 16
Supplementary Explanation of the Program Steps of FIG. 16

| Program Step | Comment |
|---|---|
| 931 | Multiply the value in temporary location C (see block 927) by the value in CORR and store the adjusted C factor in C. |
| 932 | Store value in C in FILE X at CTABL at current values of I COUNT and J COUNT |
| 933 | Compare I COUNT to six. If I COUNT is less than six, go to block 934. |
| 934 | Increment I COUNT by one and reenter at block 925, FIG. 15 |
| 935 | Compare J COUNT and one. If less than one, go to block 936. |
| 936 | Increment J COUNT by one and reenter at block 924, FIG. 15. |
| 937 | The computer output contact at point nineteen of digital output (DO) group forty two hundred and six (not shown) is closed by the computer in response to this program step to energize solenoid 240, FIGS. 3 and 6, from the plus 24 volt supply and conductors 505 and 506 |
| 938 | Program Fourteen reschedules itself to run again in approximately one second. |

Comments Regarding Program Fourteen

1. The values stored under RSTABL (118-133) will be identical to the values stored under RGTABL(-44-59) and, therefore, the former table will be eliminated when the necessary program changes are also made. The RK and TK correction factor approach allows this simplification of the calculations.

2. Program Fourteen can be further revised to eliminate the need for the nominal diffusor transmittance, $T_d$, completely. Manipulation of the terms of the equations involved permits this elimination. Note referring to Table 4, S.0023, that TPDOTD, the ratio of TPD/TD, is equal to (TSP* TK)/TSD, eliminating the need to know the absolute value of TD. TD is the computer symbol representing $T_d$, the transmittance of the diffuser. Refer also to the paragraph following Table 2.

3. Program Fourteen also calls for the re-initialization of the algorithm which smooths the "raw" reflectance and transmittance after each standardization. It is presently considered that this re-initialization will not only be unnecessary, but would add to control problems. Consequently, this will likely be changed so that this smoothing goes on indefinitely after a run start-up. (Note: Do not confuse the smoothing of the "raw" data from the paper with the correction factors acquired during standardization—The latter will not and likely should not be smoothed at all.)

4. Program Fourteen has not as yet been debugged. Debugging can only be accomplished after connecting the computer to the system of FIGS. 1-6 via an A to D converter. It is considered that such debugging is a routine matter well within the skill of the art. It may be noted that the OMOD is now on line as shown in FIGS. 1-6 and data collection has begun.

Summary of Operation of Program Fourteen

Program Fourteen is designed to perform various functions described as follows:

1. Sequentially read the reflectance and transmittance values stored in the Process File until both values for each of the seven OMOD filter positions are obtained.

It takes about two seconds from the time the filter wheel is advanced until the photocell readings reach a near equilibrium condition. Program Fourteen is, however, linked timewise to the DDC scan program and is programmed to run every second also. Consequently, any data acquired before the photocells reach a near equilibrium condition, will be liable to intolerable error. Program Fourteen solves this problem by processing data on a multisecond interval basis only, e.g., every 2, 3, 4, etc., seconds depending upon the choice of the value of the term SLOWDOWN which inserted in File X(five).

2. Check the OMOD to see if it is operating properly and issue alarms if it is not. "OMOD Filter Stuck" and "Skipped Filter" alarm messages were made available.

The upper OMOD head is designed with an extra reed switch 358, FIG. 6, which closes when the brightness filter is in the optical train pathway. (Previous description herein refers to the brightness filter as the first position; however, Program Fourteen refers to it as the zero position.) The computer program checks the status of this switch as being open or closed by means of Point 22-Group 1400. The filter index is initialized back to zero each time the status of Point 22-Group 1400 is closed. Discrepancies, should they occur between the expected filter index based on the incremented count and the actual filter position can be readily recognized by this program. This serves as the basis for the alarms previously mentioned.

3. Determine when and how often the optical property Data Reduction Program, No. Forty Two, (see FIGS. 17-20) is to be run. This is controlled by the value chosen for the term "CYCLE".

4. Read the OMOD head position and the average basis weight of the paper being produced and store for use in subsequent calculations or program logic tests. This information is readily available from a basis weight control program which has been in use for several years.

5. Correct the "raw" reflectance and transmittance data by multiplying each of the fourteen values by the appropriate correction factor. The values of these correction factors are updated by the last standardization sequence which occurred prior to their actual use (see 7 below).

6. Exponentially smooth each of the corrected reflectance and transmittance values and store for subsequent calculations.

Exponential smoothing requires a previous value to act upon; however, such previous value is not available for run startup, etc. An initialization technique involving an initialization index, k, is employed to solve this problem. The degree of smoothing is determined by the value chosen for α (ALPHA).

7. Initialize and control the automatic standardization of the OMOD.

The OMOD heads are mounted next to an Electronic Automation Inc. (EA) basis weight gauge in a piggyback fashion. This EA system utilizes an "O" frame to permit scanning the full web width. It is also designed to automatically retract the carriage 25, 26, FIG. 2, of the scanning mechanism upon which the basis weight gauge and OMOD are mounted, to an offsheet position (FIG. 2) at 1-hour intervals. Program Fourteen takes advantage of this schedule to standardize the OMOD at the same time that the basis weight gauge is being standardized. When offsheet, the very durable Lucalux backing 135, FIG. 3, is always in position to permit checks of its reflectance and transmittance. Due to its durability and inertness, the latter should remain unchanged for long periods of time. In addition, the moving web will insure its cleanliness prior to each standardization occurrence. Consequently, this standardization procedure will allow for accurate updating of the correction factors for each filter position. In so doing, it compensates for any changes which may inadvertently occur in the light source, filters, photocells, lenses, electronic amplification, etc.

Two overall geometrical correction factors are also employed at this point of the program to adjust for any relative head spacing or alignment change that may also inadvertently occur. Experimental data has shown that the same geometrical correction can be used for each reflectance measurement. The values of these two factors are, however, not determined automatically, but must be determined by external means involving offline audit testing by comparing OMOD readings with those of off-line standard laboratory instruments before being fed into the proper computer storage. Initial values of these two factors will be unity; in which case, the relative head geometry will be assumed to be in standard condition and no geometrical correction factor required.

The alternative to using these geometrical correction factors is to realign and/or respace the heads when needed. In the case of minor adjustments, the former approach is clearly the more desirable where the heads are in an inaccessible location and functioning on a high-speed paper machine with little downtime available for such mechanical readjustments.

Program fourteen as presently devised, does not call for the exponential smoothing of the correction factors updated upon each standardization. This could be easily changed should on-line experience indicate that such smoothing is desirable.

8. Control the advance of the OMOD filter wheel 210, FIG. 4, to the next filter position at the desired time interval. This is accomplished by the computer 996, FIG. 6, directing the closure of a loop 505, 506, FIG. 6, which energizes the solenoid. The energized solenoid lifts the rachet arm 230, FIG. 3, clear of the lug against which it was previously braced. The filter wheel shaft is under a continuous torque, tending to rotate it at all times. Thus, it begins to rotate when freed of the holding ratchet arm; but it is stopped again at the next lug, since by then the solenoid attached to the ratchet arm is once again de-energized by computer command. The low torque motor 209, FIG. 6, designed to be stalled indefinitely without harm provides the necessary filter wheel torque.

9. Program fourteen reschedules itself to run again in approximately 1 second.

Optical Property Data Reduction Subroutine of FIGS. 17-20 (Program Forty Two)

The purpose of this program is to reduce the corrected reflectance and transmittance data into terms with which papermakers are familiar and upon which paper optical specifications are based; e.g., brightness, opacity, color and fluorescence. A description of this program follows.

The following Tables will serve to supplement the labels applied to the blocks of the flow chart illustrating this program.

TABLE 17

Figure 17:
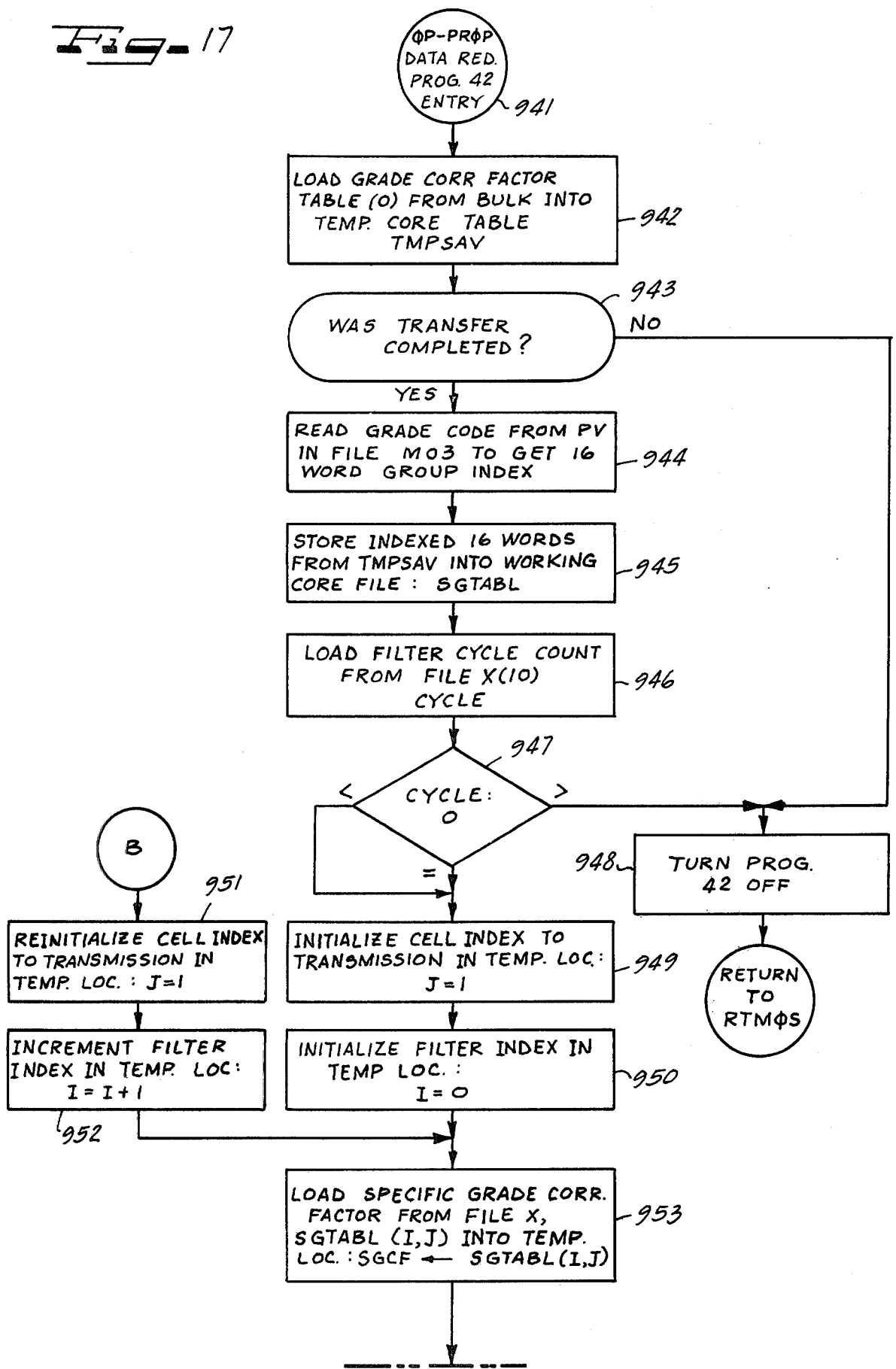
FIGS. 17–20 when arranged in a vertical sequence represent a data reduction program forty-two whose purpose is to reduce the corrected reflectance and transmittance data as produced by the program of FIGS. 8–16 into terms with which papermakers are familiar and upon which paper optical specifications are based, e.g. brightness, opacity, color and fluorescence.

Supplementary Explanation of the Program Steps of FIG. 17

| Program Step | Comment |
|---|---|
| 941 | Entry to Program Forty Two |
| 942 | Load grade correction factor table from bulk storage into the temporary core storage table TMPSAV. |
| 943 | Was transfer to TMPSAV completed? |
| 944 | Read the grade code from the process variable input file MO3 to obtain a sixteen word group index. |
| 945 | Transfer TMPSAV into the working core file SGTABL. |
| 946 | Load content of FILE X (ten) into CYCLE. This register is decremented during operation of Program Fourteen. |
| 947 | Compare CYCLE and zero. |
| 948 | If cycle is greater than zero, turn Program Forty Two off and return to RTMOS. |
| 949 | Set location J to one. |
| 950 | Set location I to zero. |
| 951 | On entry at B, set location J to one. |
| 952 | Increment the value in location I by one. |
| 953 | Load value from SGTABL of FILE X (See Table 7) for current values of I and J into SGCF. |

TABLE 18

Figure 18:
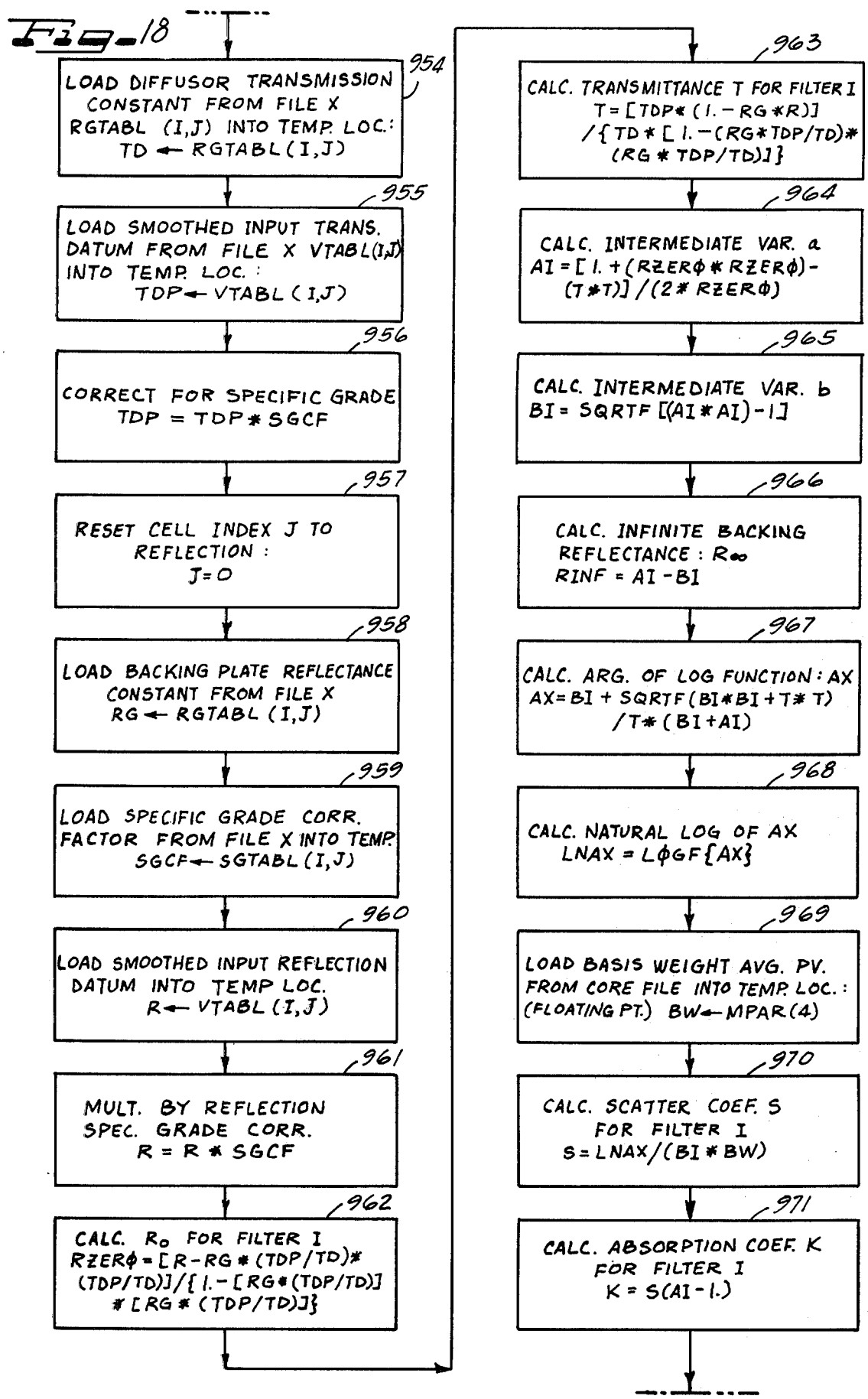

Supplementary Explanation of the Program Steps of FIG. 18

| Program Step | Comment |
|---|---|
| 954 | Load pertinent value from RGTABL into TD. |
| 955 | Load indexed content of VTABL into TDP. |
| 956 | Multiply by SGCF (See block 953, FIG. 17). |
| 957 | Set J to zero. |
| 958 | Load indexed value from RGTABL of FILE X into RG. |
| 959 | Load desired value from SGTABL of FILE X into SGCF. |
| 960 | Load indexed value from VTABL of |

TABLE 18-continued

Supplementary Explanation of the Program Steps of FIG. 18

| Program Step | Comment |
|---|---|
| | FILE X into R. |
| 961 | Multiply R and SGCF and store product in R. |
| 962 | Calculate $R_o$ using the equation given in Table 6 in conventional form. |
| 963 | Calculate transmittance T using the equation of Table 6. |
| 964 | Calculate the value A/2 where A is given in Table 6. |
| 965 | See the equation for $R_{oo}$ in Table 6. |
| 966 | See the equation for $R_{oo}$ in Table 6. |
| 967–970 | The scattering coefficient S is also calculated using Kubelka-Munk Theory on the basis of the equation: $$S = \frac{1}{b \times \text{Basis Weight}} \times [\text{Arc Sinh } (b/T) - \text{Arc Sinh } b]$$ where $b = \sqrt{a^2 - 1}$ and $a = (1 + R_o^2 - T^2)/2 R_o$ |
| 971 | The absorption coefficient K is found from the equation: $K = S(a - 1)$. |

TABLE 19

Figure 19:
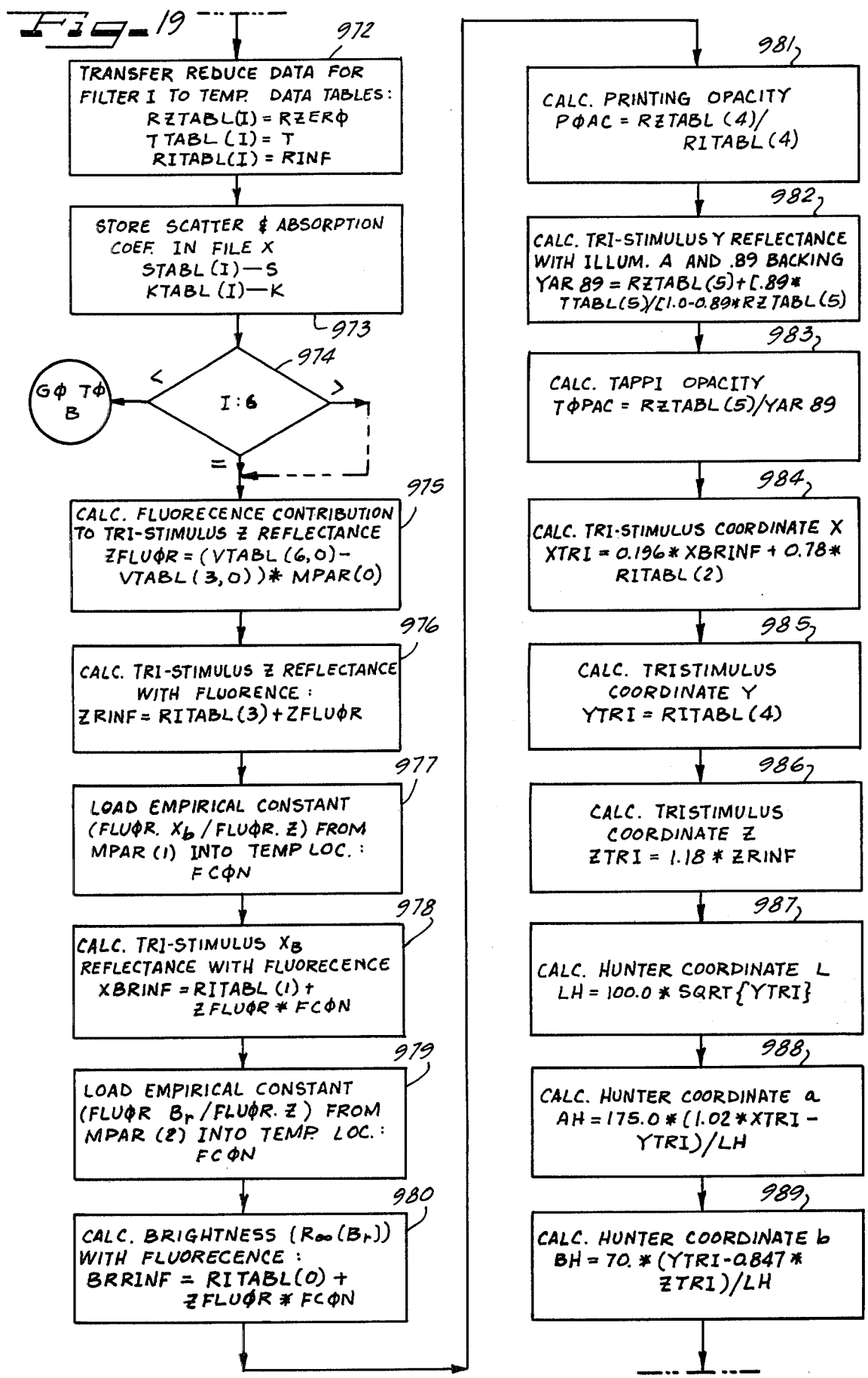

Supplementary Explanation of the Program Steps of FIG. 19

| Program Step | Comment |
|---|---|
| 972 | Transfer the calculated data to the temporary data tables at the locations corresponding to the current value of I. |
| 973 | Store calculated scattering coefficient S and absorption coefficient K in FILE X. |
| 974 | Go to entry B at block 951, FIG. 17, to repeat the calculations for the other filter wheel positions if I is less than six. |
| 975 | See the calculation of $F_Z$ in the section of this specification entitled "Structure and Operation of a Prototype Optical Monitoring Device". |
| 976 | Calculate $R_{oo}$ including fluorescence contribution and store at ZRINF. |
| 977 | For example $F_{x(Blue)}$ may equal |
| 978 | 1.204 $F_Z$ where $F_Z$ is found at step 975, and $R_{oo}$ ($X_{blue}$) plus $F_{x (Blue)}$ gives the desired value for BRINF. |
| 979 | For example $F_{Brightness}$ may equal |
| 980 | 0.864 $F_Z$. Thus $R_{oo}$ (Brightness with fluorescense) plus $F_{Brightness}$ and this sum is stored at BRRINF. |
| 981 | Printing opacity is calculated by dividing $R_o$ by $R_{oo}$ (both from the Yc filter wheel position. |
| 982 | For TAPPI opacity, obtain the ratio |
| 983 | of $R_o$ to R.89 using the $Y_A$ filter wheel position. |
| 984 | The C.I.E. X tristimulus value is calculated as follows: $X = 0.196 R_{oo} (X_{Blue}) + .78 R_{oo}$ (X Red) |
| 985 | C.I.E. tristimulus value $Y = R_{oo} (Y_c)$ |
| 986 | C.I.E. tristimulus value $Z = 1.18 R_{oo} (Z)$ |
| 987 | Compare block 985. |
| 988 | See blocks 984, 985 and 987. |
| 989 | See blocks 985, 986 and 987. |

TABLE 20

Figure 20:
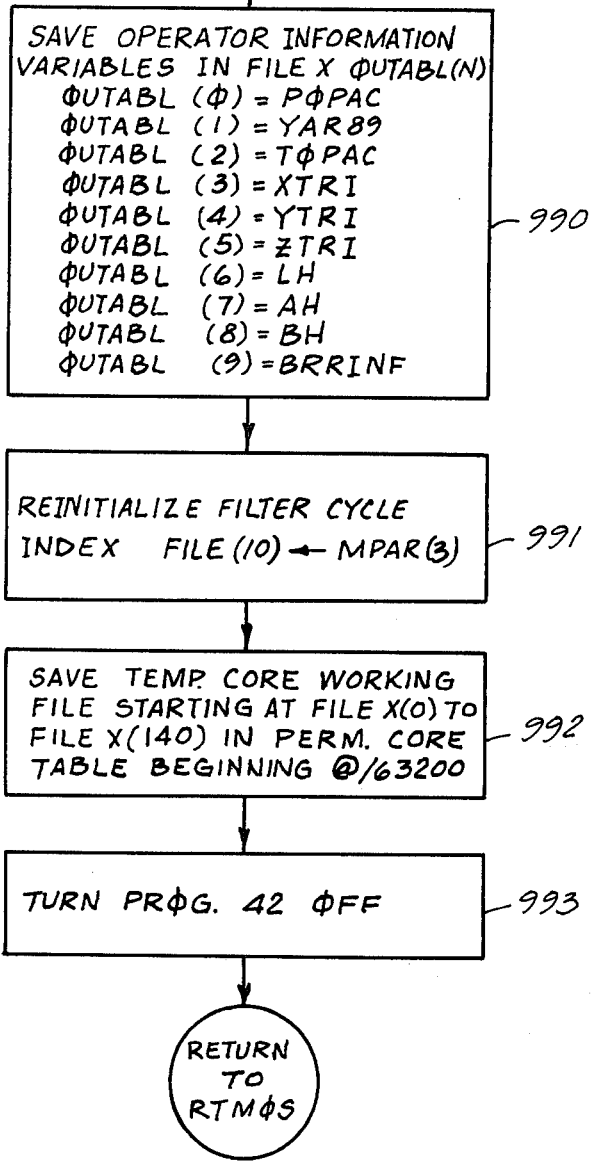

Supplementary Explanation of the Program Steps of FIG. 20

| Program Step | Comment |
|---|---|
| 990 | See Table 7 for a showing of OUTABL. The data in OUTABL is available for print out on demand. |
| 991 | The reset value at FILE X (one hundred thirty seven) is placed at FILE X(ten). See Table 7. |
| 992 | Save FILE X in the permanent core table beginning at location 63200. |
| 993 | Turn Program Forty Two off and return to RTMOS. |

Comments Regarding Program Forty-Two

1. Although not indicated as yet, the output of the fluorescent contribution to TAPPI brightness will be part of the computer output when the programs are finalized.

2. Program Forty-Two has been checked out against a currently operating program used on a research Hewlett-Packard computer and both give the same results.

3. It is planned to study means of determining and using the Specific Grade Correction Factor other than that described in Program Forty-Two. It may be decided to apply such correction directly to $R_{oo}$ rather than to the smoothed values of $T_{pd}$ and $R_g$. The transmittance of the paper, T, may not need any Specific Grade Correction and could then be used along with the corrected $R_{oo}$ to compute the scattering and absorption coefficients s and k. The latter will be very useful and may represent preferred parameters for closed loop control.

Summary of Operation of Program Forty-Two

The purpose of this program is to reduce the corrected reflectance and transmittance data into terms with which papermakers are familiar and upon which paper optical specifications are based; e.g., brightness, opacity, color and fluorescence. A description of this program follows.

1. The data reduction steps of this program are performed only if the term "CYCLE" which is decremented in Program Fourteen, is zero or negative. Otherwise, this data reduction routine is by-passed completely.

2. The exponentially smoothed reflectance and transmittance data acquired by Program Fourteen are first corrected by multiplying each of the fourteen values by an appropriate Specific Grade Correction Factor (SGCF). With a few exceptions the SGCF'S provide only small corrections, if any at all. The SGCF'S serve two purposes.
   a. They compensate for the small errors resulting from the use of the Kubelka-Munk or energy balance equations when the latter do not apply exactly.
   b. They allow the reduced data values to precisely correspond to any one of several possible off-line instruments. Existing off-line instruments do not agree among themselves. Thus, the choice of the off-line instrument for performing the audit testing will affect the values of the SGCF'S.

3. The next part of Program Forty-Two computes and stores the values of $R_o$, T, Roo, S and K of the paper being measured for each of the first six of the seven OMOD filter positions. Kubelka-Munk and IPC derived energy balance equations are used for this purpose. Note that prior to these calculations, the reflectance values were those of the single ply of paper when backed by the Lucalux and were symbolized by $R_g$. Similarly, the former transmittance values were those of the single ply of paper in series with the Lucalux, now serving as a diffusing window. This was symbolized by $T_{pd}$.

The phenomenon of fluorescence is not accounted for by Kubelka-Munk theory. For this reason the OMOD optical geometry was chosen to exclude fluorescence by eliminating ultra violet (U.V.) light from the incident light beam of the first six filter positions. For reasons explained later, the seventh filter position permits the reflectance of the Z function with ultra violet energy present in the incident beam.

4. The degree of fluorescence as measured by the "Fluroescent Contribution" is determined next. Fluorescence occurs as a result of excitation of special dyes (optical brightness or fluorescent dyes) by ultra violet energy contained within the incident light beam(s). The "Fluorescent Contribution" is defined here to be the increase of the reflected light flux that occurs as a result of the existence of some standard quantity of ultra violet energy in the incident light beam.

Such U.V. energy is rapidly absorbed by the outer layers of most conventional papers. Consequently, fluorescence is primarily a characteristic of the surface of the paper being viewed. Thus, for practical purposes, the value of $[R_g$ (with fluor.)$-R_g$ (without fluor)$]=[R_{oo}$ (with fluor.)$-R_{oo}$ (without fluor.)$]$ when the same incident light beam containing the same U.V. energy is used in both cases. The right side of this equation is by the definition above, the Fluorescent Contribution provided the standard quantity of U.V. light is employed in the incident beam. The left side of this equation is a quantity measureable on a single ply of the moving paper web. In the case of the OMOD a measure of the fluorescent contribution to the Z function reflectance is obtained from the term, $[R_g$ (Filter No. 7)$R_g$ (Filter No. 4)$]$. The filter arrangement existing in the No. 7 OMOD filter position permits about twice the standard quantity of U.V. energy to strike the paper. (The U.V. energy in the incident beam of the Standard TAPPI Brightness Tester is considered to be the standard quantity here). This increases the sensitivity of this measurement by two-fold. It also necessitates the use of a proportionality constant of approximately one-half to compute the value of the standard Fluorescent Contribution to the Z function reflectance.

The Fluorescent Contribution to the reflectance of the $X_R$ and Brightness functions can be computed directly from the Z function Fluorescent Contribution. The multiplication factors involved are constant for a given optical brightner and need to be changed only if the type of optical brightner is changed. The Fluorescent Contributor to the $Y_C$, $Y_A$ and $X_R$ functions can be ignored as being inconsequential to the typical optical brightner used in the paper industry today.

5. Defining equations are used to compute and store for accessible putout values of the following:
 a. Standard TAPPI Brightness
 b. Printing opacity based on illuminant C
 c. $R_{89}$ based on illuminant A
 d. TAPPI opacity based on illuminant A
 e. X Tristimulus value
 f. Y Tristimulus value
 g. Z Tristimulus value
 h. Hunter Coordinate, L
 i. Hunter Coordinate, a
 j. Hunter Coordinate, b
 k. Fluorescent Contribution to TAPPI Brightness

DISCUSSION RELATING TO THE PRESENT INVENTION BASED ON A PAPER PUBLISHED IN 1974

The following pages are excerpts based on a paper prepared for the American Paper Institute, which paper is dated Jan. 10, 1974 (and is understood to have been actually published some time after Jan. 23, 1974.) The paper was prepared by an author who is a joint contributor to certain improvements described but not claimed herein. The paper exists in printed form and is incorporated herein by reference. The incorporated paper is identified as "REPORT NO. 58, TO: American Paper Institute Instrumentation Program", "SUBJECT: An Analysis of On-Machine Optical Instrumentation", "DATE: Jan. 10, 1974" and is submitted by the Institute of Paper Chemistry, Appleton, Wis.

The Institute of Paper Chemistry was retained to evaluate an early conception of an on-the-paper-machine optical monitoring device for simultaneous measurement of reflected and transmitted light, and to assist in the optimum implementation of such conception. Accordingly, a substantial portion of the work reported in the following excerpts appears to inure as part of the original conception.

The following discussion is presented with respect to each of the illustrated embodiments as constituting a description bearing on the background of the invention and as clarifying and amplifying on the nature of such invention, even through the paper may also include subject matter which is based on work entirely independent of the project sponsored by the assignee of the present invention. Further, the paper will indicate the range of equivalents to each of the illustrated embodiments with respect to matters such as spectrum and geometry of illumination.

Summary

Various aspects of the on-machine measurement of the optical properties of paper for the control of opacity, standard brightness, and color have been examined. Whereas many optical property specifications are based on reflectances determined on opaque pads of paper, on-machine measurements are limited to the various optical values which can be determined on single thicknesses of a moving web. Thus, one must either control to the optical property which can be measured on-machine or strive to develop reliable correlations between the on-machine and off-machine measurements. The latter approach is more desirable. For this purpose, it is advantageous to adopt the design features of the off-machine testing apparatus to the fullest extent possible for on-machine use. Fortunately, the important factors in optical instrument design related to spectral characteristics, geometry, and photometric linearity can be translated to on-machine use with considerable exactness.

A large number of different approaches are possible in the measurement of optical properties of single sheets for purposes of control. Of these, however, distinctions can be made between single measurements, of reflectance, for example, and the measurement of two optical parameters for the same sampled area. The latter approach permits calculation of thick pad reflectivity values using appropriate theory with an essential independence of basis weight, whereas single reflectance data are functions of basis weight requiring empirical compensation. Although various possible pairs of optical measurements can be made on the same specimen area, among the most satisfactory for the use of theory are reflectance with black body backing and transmittance. The Kubelka-Munk theory, though not rigorously applicable in practice, has been shown to be rather successful in predicting thick pad reflectivity from such data in laboratory tests for white papers of reasonable homogeneity. It is less successful for deeply colored papers and for sheets of very low basis weight.

The sensitivity of spacing of white backings from paper specimens was measured with respect to the color of various commercial papers. At a central spacing of 0.32 cm, it was determined that a variation in spacing of about 0.020 inches (0.05 cm) is possible for most papers without noticeable color difference.

Optical measurements would be made on-machine on webs of varying moisture content and at elevated temperatures compared to a controlled laboratory testing environment. An experiment study of the effect of changing moisture content (R.H. range of 5 to 84%) on color showed small effects for most white papers, which were attributed to differences in surface structure. Somewhat larger effects were noted using directional illumination compared to diffuse illumination. The largest effects, for some colored papers, were attributed to changing spectral absorption characteristics of the dyestuff. Sheet moisture content effects on optical properties were judged to be within tolerable limits over a range corresponding to relative humidities between 5 and 50%.

The effect of temperature on the color of various commercial papers was studied over a range of 23° to 62° C. Important effects were found only for two colored papers. It was noted that significant elevations of specimen surface temperature can occur in optical apparatus employing high-intensity illumination.

Most other variables involving paper properties, machine operation, and mill environmental conditions are unlikely to be eliminated through instrument design or through the development of appropriate compensating factors. For these remaining factors, empirical correlations would be required to establish agreement between optical data or obtained on and off machine.

Introduction

Specifications for the various optical properties of paper are presently based on measurements made with laboratory instruments. Considerable standardization of optical instrumentation and testing methods have been developed, but new instruments and analytical methods are often introduced to the industry as well. Changes are welcome when they provide advantages in such areas as the utility of the measurement, improved accuracy, better agreement between laboratories, and in overall testing costs. The well-established advantages of industry-wide standardization in the measurement of the optical properties, however, must always receive serious consideration.

In recent years, the control of paper quality on the paper machine has grown in importance and, for optical properties, on-line control is a very practical objective. Good control strategy requires that the properties of the sheet be determined rapidly on the moving web, but it is usually not possible to duplicate laboratory instrumentation for on-machine use. Whereas on-machine measurements are limited to such data as can be acquired on a single thickness of paper, optical properties such as brightness and color are determined on multiple thicknesses. Too often, optical instrumentation is developed for on-machine use with emphasis on the control function, but without serious consideration given to the further problem of conforming to off-machine optical property standards. The implied assumption is that a good reliable correlation will exist between the on-machine and off-machine optical measurements. Perhaps the most logical approach to the development of on-machine optical instrumentation is to design for maximum conformance with laboratory instrumentation is such factors as instrument geometry and spectral characteristics, to employ existing theory as far as possible to inter-relate single-sheet versus multiple-sheet optical measurements and to employ empirical correlations to the minimum extent required.

As on-machine optical instrumentation becomes more widely adopted, the advantages of continuously monitoring the optical properties of paper in real-time compared to the intermittent and few data which can be acquired by off-machine testing could lead to the use of specifications in the buying and selling of paper which are based on the on-machine instrumentation. Should this ever occur, it is particularly desirable that such on-machine specifications bear the highest possible degree of correlation with the off-machine specifications in current use.

In this report, many of the factors involved in the optical characterization of a moving web in a paper machine environment are discussed relative to the off-machine properties of brightness, color and opacity.

Optical Property Measurement and Specification

Brightness

Papermaker's brightness, sometimes called G.E. brightness and now "standard brightness" was first established in the early 1930's as the particular reflectivity ($R_{oo}$) of paper determined with an instrument having a specified spectral response, specified geometry, and good photometric accuracy (1). At the same time, a system of calibration was developed whereby opal glass and paper standards are furnished periodically for each instrument.

In the early days, the scale was based on "smoked" magnesium oxide but, because of difficulty in arriving at a reproducible reflecting surface, a technique for measuring the absolute reflectance of magnesium oxide was developed (2). Thus, a total system (3) was made available so that this particular refectivity could be measured industrywide with an accuracy of about ±0.3 reflectivity units. TAPPI standards T217 and T452 give the detailed specifications for the measurement of standard brightness for pulp and for paper and paperboard respectively. The following specifications are involved.

Spectral Response

The effective wavelength of an instrument for the measurement of standard brightness is 457 nm. Although the effective wavelength is the most important parameter describing the spectral response, wavelength bandwidth and shape of the function also influence the result and are specified. The standardized overall spectral response of the brightness instrument which includes the spectral power distribution of the light source, the spectral transmittance of the glass lenses and filters, and the spectral response of the phototube is given in Table I.

TABLE I

Spectral Response of an Instrument for the Measurement of Standard Brightness

| Wavelength, nm | Spectral Response Arbitrary Units |
| --- | --- |
| 400 | 1.0 |
| 405 | 2.9 |
| 410 | 6.7 |
| 415 | 12.1 |
| 420 | 18.2 |
| 425 | 25.8 |
| 430 | 34.5 |
| 435 | 44.9 |
| 440 | 57.6 |
| 445 | 70.0 |
| 450 | 82.5 |
| 455 | 94.1 |
| 460 | 100.0 |
| 465 | 99.3 |
| 470 | 88.7 |
| 475 | 72.5 |
| 480 | 53.1 |
| 485 | 34.0 |
| 490 | 20.3 |
| 495 | 11.1 |
| 500 | 5.6 |
| 505 | 2.2 |
| 510 | 0.3 |

The prescribed spectral response precludes use of a spectrophotometer employing a narrow bandwidth at 457 nm for the accurate measurement of standard brightness.

The spectral response function was chosen in the blue region of the spectrum for maximum sensitivity to changes in bleaching and the fading of paper with time. Once specified, however, the spectral response of different instruments must be maintained to close tolerances for reproducibility in measurement on an industry-wide basis.

When papers exhibit fluorescence, whether naturally or because of the addition of fluorescent dyes, the spectral power distribution of the light incident on the specimen must be specified. For standard brightness, the specified spectral power distribution of the light incident on the specimen is given in Table II. Thus, adherence to the spectral specifications of Tables I and II permits the accurate determination of standard brightness of fluorescent as well as nonfluorescent papers.

TABLE II

| Wavelengths, nm | Spectral Power Distribution of the Light Incident on the Specimen Arbitrary Units |
| --- | --- |
| 320 | 0.0 |
| 330 | 0.7 |
| 340 | 9.7 |
| 360 | 9.7 |
| 380 | 17.1 |
| 400 | 26.0 |
| 420 | 37.2 |
| 440 | 50.3 |
| 460 | 64.1 |
| 480 | 80.0 |
| 500 | 100.0 |

In addition, the spectral transmittance of the filters and the phototube response are selected such that the instrument has negligible response to near-infrared radiant energy whether reflected from the specimen or as a result of speciment infrared fluorescence (4). It is important to note that some colored glass filters with essentially no transmittance in the red region of the spectrum will transmit substantially in the near infrared. Geometry The geometry employed for the measurement of brightness is illumination at 45° and normal viewing with the incident and reflected beam cone half-angles specified at 11.5° and 22.5° respectively. The angles of illumination and viewing are critical as paper surfaces are not ideal diffusers, and the numerical values obtained are a function of the particular geometry employed. Paper surfaces also exhibit directional effects. The light reflected when the specimen is illuminated in the "machine direction" is generally less than if the specimen is illuminated in the "across-machine direction". The brightness measurement is usually performed with the specimen illuminated in the "machine direction" and on the felt or top side. A sufficient number of sheets are required to form an opaque pad.

In the more translucent papers, an appreciable penetration of light into the sample occurs. As a result of internal light scattering, the illuminated area may differ significantly from the area of reflectance or light emergence. When this condition exists, the relative dimensions of the areas illuminated and viewed, the distribution of light on the illuminated spot, the alignment of the illuminated and viewed areas and their shapes can influence the result. In the instrument employed for the brightness measurement, the viewed area and the size and position of the illuminated spot are adjusted to prescribed standards. Conformance with the standard is ensured through use of the calibration standards. Properly adjusted, the instrument can be used to measure standard brightness of strongly translucent as well as opaque material. Photometry.

The photometric accuracy of an instrument for the measurement of brightness should be better than 0.1 point on a 0-100 scale (5). The overall error introduced through discrepancies in spectral response, geometry and the basis of standardization must total less than 0.3 point.

TAPPI OPACITY

Opacity has long been defined in the paper industry as 100 times the ratio of the diffuse reflectance of a single sheet backed with a black body to its diffuse reflectance backed by a white body having an effective absolute reflectance of 0.89. An instrument designed and built in the early 1930's and has formed the basis of a system for determining TAPPI Opacity (6).

Spectral Response

The overall spectral response of the instrument including the spectral power distribution of the light source, spectral transmittance of the glass lenses and filter, spectral reflectivity of the integrating cavity lining and spectral response of the photocell is that the $E_a\bar{y}$ function (visibility function, Illuminant A) of the CIE system (7). The effective wavelength is 572 nm and the function extends over the entire visible spectrum. The specified broad-band spectral function makes the use of narrow-band instruments inappropriate for the measurement of opacity even though the effective wavelength is proper.

Fluorescent dyes, known in industry as optical brighteners, have a rather small, if not negligible, influence on opacity as the spectral response of the instrument in the usual fluorescent region (blue) of the spectrum is quite low. Also, the fluorescent radiation from a single sheet probably would not be too different when backed by a black or white body.

The spectral reflectivity of the integrating cavity lining does influence the overall spectral response of the instrument (3) and, because it is difficult to maintain a constant lining reflectance, a system for checking and maintaining the lining reflectance is essential to good accuracy. Geometry The geometry employed for the measurement of opacity is illumination at 20° and diffuse viewing. The photodetector receives light that is both diffusely and specularly reflected from the specimen and, because there is no baffle, the photodetector also views the light directly reflected from the specimen. The ratio of diffusely to directly reflected light depends upon the level of reflectance of the integrating cavity lining (physical dimensions also are influencing factors but remain constant) and, as this ratio changes, significant changes in measured opacity can occur (8).

The illuminated area is about 10 mm in diameter with a specimen aperture of about 14.3 mm in diameter. If translucent papers or standards are to be evaluated or used, the ratio of the viewed to the illuminated area is important (8). The state of focus and alignment of the optical system particularly influences the values obtained for translucent materials.

Stray light caused by a dirty or misaligned optical system can be a source of error. The otpical system should be cleaned and aligned such that the difference in scale reading with the black body over the specimen opening when the light is blocked off before entering the cavity and with the light passing through the cavity into the black body should not be over 0.5 (0–100 scale). The reflectance of the black body should not be more than about 0.1%. The instrument scale is adjusted to read zero when the stray light is included.

Photometry

The photometric accuracy of different original instruments, employing a photocell-galvanometer system, varied from near perfect linearity to deviations as much as several points, depending upon the components. More recently, with the addition of solid state amplifiers and digital readouts, the photometric accuracy can be better than 0.1 (0–100 scale).

Calibration Standardization

In the measurement of the ratio $R_o/R_{0.89}$, it is necessary that the white body have an effective reflectance of 0.89. The instrument is equipped with a rotatable tube, one end of which contains a black cavity and the other the white body. A sheet of paper is placed over the specimen opening and, alternately, the black and white bodies are brought into position. The usual white body consists of a plug of appropriately surfaced magnesium carbonate within a protective glass cover. Changing the spacing between the surface of the magnesium carbonate and the specimen permits adjustment of the effective reflectance of the white body. There are two generally accepted means for arriving at the proper white body effective reflectance. One is to employ properly calibrated opal glass standards. While convenient, unless the instrument is properly adjusted with respect to translucency effects, substantial error can result. As constructed originally, the specimen supporting surface often departed from the intended plane. Thus, while the paper could follow a particular contour, the rigid glass standards will not, resulting in further error. After correcting these potential defects, it is possible to use opal glass standards and take advantage of their great convenience.

A second more basic method consists of determining $R_0$ and $R_{oo}$ for a particular paper specimen on the absolute scale and, through use of the relationship sometimes known as the "balance of energy" equation (9) or the Kubekla-Munk theory (10, 11, 12), to calcuate $R_{0.89}$ for that specimen. The white body can then be adjusted so that this value is obtained instrumentally. Care should be exercised so that all reflectances are obtained on an identical area of the specimen. Charts are available (13) relating the reflectances $R_o$, $R_{oo}$ and $R_{0.89}$ or an appropriately programmed computer can be used to calculate the $R_{0.89}$ value.

Paper opacity standards calibrated for use with the opacimeter are now also available. These are convenient to use and will eliminate some of the difficulties associated with the opal glass calibration standards.

Magnesium oxide powder with an assigned absolute reflectance value is also available for use in calibrating the opacimeter for the measurement of relfectance on the absolute scale.

PRINTING OPACITY

While the choice of spectral response for the measurement of opacity was excellent, the choice of the ratio $R_o/R_{0.89}$ as opposed to $R_o/R_{oo}$ was not. Printing opacity ($R_o/R_{oo}$) more nearly relates to the end use of the product and would eliminate the problem of adjusting the white body (14). The fact that a single sheet is required for the measurement of TAPPI Opacity whereas an opaque pad is required for printing opacity appears to be a factor in the reluctance of the industry to change. It is more convenient to determine the opacity of the single sheet using the white body.

COLOR

Spectrophotometers and filter colorimeters are the two main classes of instruments employed in the measurement of color. The spectrophotometer provides basic reflectivity information as a function of wavelength over the entire visible spectrum. The reflectivity ($R_{oo}$), obtained on the thick pads of paper, with the values based on the absolute scale is basic to color measurement. The reflectivity curve contains the essential information regarding the color of the object, but considerable computation is required to derive the desired colorimetric specifications. Spectral In the numerical specification of color, it is necessary to specify the spectral characterisitics of the illuminant and the spectral response of the observer. The CIE system (7) gives the spectral power distribution for various illuminants and the spectral response of the standard observer. Illuminant C has been used almost exclusively in the past in the specification of color, however, the use of illuminant $D_{6500}$ (15) is now being considered. The specifications for Illuminant $D_{6500}$ include the ultraviolet region of the spectrum. The ultraviolet region for Illuminant C was not specified.

For color definition in the CIE system, the psychophysical response of the "standard observer" to the spectral distribution of light reflected from a specimen (as provided by the spectral power distribution of the illuminant and the spectral reflectivity curve) is matched by a combination of three standard stimuli, each of appropriate power. The relative levels for the three separate stimuli are the tristimulus values which together constitute the chromaticity of a color. It is more useful to compute the fraction each stimulus has to their sum since only two of the three fractions need by specified for chromaticity definition. It then becomes possible to restate the chromaticity of the measured color, for a given illuminant, in terms of "dominant wavelength" and "purity". To complete this specification of color, the luminous reflectance of the specimen is provided directly in the CIE system by the tristimulus value "Y".

Geometry

Four illumination and viewing conditions are recommended for use in the CIE system. These include illumination at 45° and viewing normal to the surface (0°), normal illumination with 45° viewing, diffuse illumination with normal viewing and normal illumination with diffuse viewing. Various advantages and disadvantages relate to each of these geometries from the viewpoint of best representing visual estimates of color. Generally, the geometry employed for visual inspection is more nearly 45°-0° or 0°-45°. Thus, an instrument equipped with this geometry would be expected to agree more closely with visual estimates than an instrument equipped with diffuse--normal geometry. It can be clearly demonstrated that a colorimetric evaluation using an instrument equipped with diffuse-normal geometry does not correlate closely with visual estimates for certain surfaces. Also, it is difficult to maintain a constant integrating cavity lining reflectance for long periods. The diffuse-normal geometry, however, is less sensitive to surface roughness and will give more reproducible results when specimens having an irregular surface are evaluated.

Control of the sizes, shapes and relative positions of the illuminated and viewed areas is also required for proper accounting of specimen translucency effects.

Photometry

Photometric accuracy of better than 0.1 point (0-100 scale) is desired.

Filter Colorimeters

Though the spectrophotometric approach to color measurement is the most basic and rigorous, its greater cost and computational demands have led to the development of filter colorimetry. One approach involves the use of suitable lamp, filters and photodetector combinations chosen to match the spectral functions of the CIE system ($\bar{x}$, $\bar{y}$, $\bar{z}$). Thus, the instrument output may be in the form of the tristimulus values of the CIE system. Although the $\bar{y}$ and $\bar{z}$ functions can be matched quite well, the double peak of the $\bar{x}$ function precludes the use of a single filter-photocell combination. Recourse is made either to the computation of the blue contribution to the $\bar{x}$ function from the $\bar{z}$ function (three-filter colorimeter) (16) or to the use of two filters with properly weighted combined output (four-filter colorimeter) for the $\bar{x}$ function. The latter gives a more accurate measure of the X tristimulus value particularly for specimens having spectral reflectivity curves with a steep slope through the blue region of the Spectrum. For color matching, particularly in control applications, the three or four-filter colorimeter may prove useful for many colors of commercial interest. However, it is subject to many limitations such as basic accuracy and the fact that colorimetric data are obtained for a single illuminant. For instance, the match may be metameric and under another illuminant there could be a serious mismatch.

Another form of colorimeter involves the use of a larger number of narrow-band filters with transmittance peaks distributed across the visible spectrum. If the filter transmittances are confined to sufficiently narrow ranges of wavelength and an adequate number are used, one may approach the utility of an abridged spectrophotometer. For many purposes of control, the abridged spectrophotometer can have important advantages over the three or four-filter colorimeter.

If a specimen exhibits fluorescence, the best spectrophotometer or filter colorimeter design utilizes illuminants with broad spectral power distribution, including appropriate intensities in the ultraviolet, with viewing through a monochromator for the spectrophotometer and through appropriate filters for the colorimeter. Thus, the fluorescent radiation will be excited in accordance with the spectral power distribution of the illuminant and the photodetector will view the reflected light and fluorescent radiation properly.

ON-MACHINE MEASUREMENT OF OPTICAL PROPERTIES

The optical information which can be acquired on the moving web of a paper machine is limited essentially to that which can be obtained using a single sheet. Reflectances can be obtained for various conditions of illumination of the single sheet and for different backings. The backing can be black body or established at various reflectance levels. Ordinarily the backing would consist of ceramic or glass placed either at a specific distance from the sheet surface or in contact with the sheet. In addition to such reflectivity measurements as can be obtained, it is often possible to obtain useful transmittance information (except for very opaque sheets). Of course, where the transmittance is very low, the reflectance of a single sheet will approach the true $R_{oo}$ value.

Optical specifications which properly apply to thick pad reflectances, $R_{oo}$, are not readily abandoned in favor of specifications based on single sheet reflectances. Hence, the question of correlation of such on-machine data as can be obtained with actual experimentally determined $R_{oo}$ data is of interest. The most useful approach is to utilize to the fullest possible extent the existing theory which permits calculation of $R_{oo}$ from on-machine optical data. To the extent that such calculated values are not in agreement with the experimental data, empirical correlations could then be applied to bridge the remaining gap. Such an approach is more desirable than is dependence on empirical correlations alone especially if the calculated result is in close agreement with off-machine determinations.

the equations, based on the Kubelka-Munk theory, which interrelate various reflection and transmittance measurements are of principal interest in obtaining estimates of the reflectivity, $R_{oo}$, from on-machine measurements. It is always necessary to obtain two different optical parameters preferably on the same areas of single sheets for the calculation of $R_{oo}$ using these equations. The two measurements can take many forms. For example, the reflectance of paper with black body backing ($R_o$) along with transmittance (T) is both appropriate and experimentally desirable. It is also possible to employ any two reflectances, obtained with different backings, but this introduces problems, particularly with the backing reflectance color. Through the appropriate measurement of two optical parameters, it is also possible to characterize papers in terms of their scattering and absorption powers--not possible with single reflectance measurements The theoretical relationship between $R_{oo}$, $R_o$ and $T$ is given in equations 1 and 2. This relationship would be applied as far as possible various desired spectral power distributions, such as are employed in standard brightness, TAPPI Opacity, and the various spectral functions associated with color measurement.

$$a = (1 + R_o^2 - T^2)/R_o \quad (1)$$

$$R_{oo} = (a/2) - \sqrt{(a/2)^2 - 1} \quad (2)$$

Where the $R_{oo}$ values are determined with the appropriate filters, the tristimulus values (Illuminant C) can be calculated as shown.

$$X(\text{blue}) = 0.1973\ R_{oo} \quad (3)$$
$$X(\text{red}) = 0.7831\ R_{oo} \quad (4)$$
$$X = X(\text{red}) + X(\text{blue}) \quad (5)$$
$$Y = R_{oo} \quad (6)$$
$$Z = 1.1812\ R_{oo} \quad (7)$$

TAPPI Opacity can be calculated using equations 8 and 9 where $R'$ is equal to 0.89.

$$R_R' = R_o + R'T^2/1 - R_o R' \quad (8)$$

$$C_{0.89} = 100 R_o/R_R' \quad (9)$$

Although it has often been demonstrated that the "balance of energy" equations and the Kubelka-Munk theory are very useful in interrelating the optical properties of paper determined under many different conditions of geometry and spectral power distributions, it is important to recall that some of the conditions required by theory are not met in practice. Among these, the specimen should be illuminated and viewed with diffuse light, monochromatic light should be employed and the optical properties of the material should conform to the requirement that the absorption and scattering of light be independent of each other and occur at numerous discrete sites spaced randomly throughout the substance. All reflectance and transmittance values should be determined on the absolute basis. The fact that these conditions are seldom met requires experimental testing of the theory for each intended use.

Experimental data were acquired to test the validity of this use of the theory for a number of "white" as well as more strongly colored papers. The extent of agreement which might be expected between the calculated reflectivity, $R_{oo}$, using equations 1 and 2 and experimentally determined $R_o$ and $T$ values, and actually measured $R_{oo}$ values was examined for two different optical systems. Neither system would likely be used in making optical measurements on moving webs, but both serve the purpose of testing the relationships in actual use situations.

In the first set of experiments, handsheets were prepared from bleached hardwood pulp, refined to 450 ml C.S.F., at basis weights of 32, 64, 96 and 127 g/m². The optical properties of these samples were determined using the General Electric Recording Spectrophotometer with "reversed" optics (GERS-RF). The specimen was illuminated diffusely with the spectral power distribution of a tungsten filament source modified by the integrating cavity lining. Viewing of the specimen was at 6° to the normal. Four filters were interposed separately in the reflected beam to give the spectral response for the overall system of the $E_c\bar{x}$, $E_c\bar{y}$ and the $E_c\bar{z}$ functions of the CIE system. Two filters were utilized to obtain the $E_c\bar{x}$ function. The $R_{oo}$ values, calculated from the measured $R_o$ and $T$ values using equations 1 and 2, are compared with the $R_{oo}$ values measured directly with the GERS-RF. The data given in Table I are averages for five different specimens at each basis weight ...

The calculated and measured tristimulus values are in good agreement for the white and blue bond paper with rather poor ageement for the pink bond paper. The color differences based on the differences in the calculated and measured tristimulus values are given in Table IV.

TABLE IV

Color Differences ($\Delta E$) Related to the Differences Between the Calculated and Measured Tristimulus Values for Five Commercial Papers

| Commercial Papers | $\Delta E$ |
| --- | --- |
| White Bond | 0.6 |
| Tracing Paper | 1.6 |
| Pink Bond | 8.9 |
| Coated Paper | 2.1 |
| Blue Bond | 0.9 |

Where the color differences are very large, it is probably attributable to the broad bandwidth of the spectral functions used to determine the tristimulus values and the substantial changes in reflectance with wavelength for the more highly colored papers. This can lead to error in the calculation of $R_{oo}$ from $R_o$ and $T$. Such error would likely be eliminated if a reflectivity ($R_{oo}$) curve were first calculated from the curves for $R_o$ and $T$ (appropriate number of points should be used to give an accurate $R_{oo}$ curve) before the integration leading to the tristimulus values is performed. But, of course, this is not the means by which data are likely to be obtained and treated in an on-machine color measurement system, at least at present. The results indicate that, for many papers, the theoretical relationships will give excellent estimates of $R_{oo}$ from $R_o$ $T$ acquired for single sheets. Where the discrepancies are greater than desirable, it is probable that useful empirical relationships may be established.

The estimation of $R_{oo}$ from measurements of black body backed reflectance and transmittance of single sheets using theoretical relationships is subject to less error than are estimates obtained using two reflectances obtained with different backing reflectances, for example. A further approach to the design of on-machine color measuring instrumentation involves reflectances determined on single sheets backed by a body having a selected reflectance. Obviously, such reflectances will be equal to $R_{oo}$ for any paper only if the effective reflectance of the backing is also equal to $R_{oo}$ for that paper. Also, the backing will not ordinarily have the color of the paper. Hence, recourse must be made to empirical relationships between the measured reflectance values and the color of the samples as would be determined directly using opaque pads. Further, since it is often desirable to employ a spacing of some magnitude between the moving web and the backing surface, variations in the spacing which would likely occur in practice would be another source of discrepancy.

The following experiments were conducted to explore the differences in the color of paper when backed by a translucent opal glass and an opaque, enameled plaque. The spectral reflectivity curves for both backings was determined with the GERS and are given in FIG. 1. It should be noted that these reflectivity curves cannot be use to determine the effective reflectances of the backings when employed against paper and, particularly for the translucent opal glass would be at different levels if determined with different geometry. Reflectance data on the paper specimens were obtained with both GERS-RF and with the Automatic Color-Brightness Tester (ACBT). The latter employs 45° illumination and normal viewing. Both instruments were equipped with appropriate filters so that the tristimulus values could be determined from four reflectance measurements (Illuminant C). Six commercial papers were evaluated with the white body backings at different spacings from the sheet . . .

WEB FACTORS WHICH INFLUENCE THE MEASUREMENT OF OPTICAL PROPERTIES

Basis Weight and Sheet Formation Variability

Basis weight variability, of which sheet formation represents a rapidly varying form, is a matter of interest in the on-machine measurement of optical properties. All optical properties are basis weight dependent in some degree. The dependence may arise because of changes in sheet structure with basis weight or may be a consequence of the simple change in mass per unit area for constant sheet structure. Thus, whereas the reflectance of a thick pad of paper may prove to be relatively independent of basis weight, the reflectance of a single sheet with black body or other designated backing and transmittance are expected to show basis weight effects. If the basis weight is known, it is possible to apply first-approximation corrections for departures in basis weight from a target value. However, such corrections would be different for different papers, would need to be developed experimentally and would best be applied to the longer-range basis weight variations.

Rapid changes in basis weight on the scale involved in sheet formation effects will result in rapidly changing optical properties as the moving sheet is scanned by an instrument in fixed position. The true time-varying signal might well be averaged by the on-machine instrument unlike the arithmetic averaging of the same optical property values determined statically off-machine. Whether the two averages are significantly different would depend both on the nature of the time-varying signal and the time-response characteristics of the on-machine instrument.

Where two optical measurements are made simultaneously at one position on a moving web, each would be averaged instrumentally. Values of $R_{oo}$ calculated from such averages may differ from an average of $R_{oo}$ values calculated from various pairs of optical values (for example, $R_o$ and T). Though such an error would be small for small basis weight variations, it could be of importance for some papers.

If sets of data are acquired on moving webs by interposing different filters in time sequence, for example, the particular values within a set would be obtained on different areas of the web and each could relate to a slightly different basis weight. Obviously if such values are affected by basis weight, the optical property described by the set (color, for example) would be in error if the basis weight were not constant. One could in such an instance, resort to the repetitive collection of sets of values with an averaging of the art results over a longer time period. It would be desirable to avoid the collection of data such that any particular value within a set is always obtained at the same unique web position or time cycle.

Fiber Orientation

Machine-made papers usually have some degree of fiber orientation which causes a difference in reflectance if the sheet is illuminated in the "in-machine" or "across-machine" direction. Generally, the reflectance is lower when the specimen is illuminated in the "in-machine" direction. Fiber orientation is usually less pronounced on the felt side; hence, optical data are usually obtained on that side. Standard brightness is measured on the felt side and the "in-machine" direction. On-machine measurements can of course, be performed in the same way.

Polarization of light occurs to some extent when a paper surface is illuminated at an angle such as 45° and the extent of polarization depends upon the kind of surface and to some degree upon fiber orientation. For this reason, the on-machine instrumentation should have the same response to polarized light as the off-machine instrument.

Two-Sidedness

Most papers have different spectral reflectivities for the felt and wire sides with the effect being more pronounced for very light basis weights and for coated papers. This affects the relationship between $R_o$, T and $R_{oo}$ causing an error in the calculation of $R_{oo}$. This effect is not large if the measurements of $R_o$, T, and $R_{oo}$ are all made with the same side of the sheet facing the light beam on the on-machine as well as the off-machine instrument.

Moisture Content

In on-machine testing of paper, the moisture content may be at a level different from that employed in off-machine testing. Also, the intensity of the light incident on the specimen in some off-machine colorimeters is of a sufficiently high level to cause an appreciable change in temperature moisture content of the specimen during the course of performing a reflectance measurement.

Reflectance data have been obtained for "white" and dyed paper samples using the GERS and the ACBT, as these instruments employ a very low level of illumination thus minimizing departure from established laboratory environmental conditions. The GERS employs 6°-diffuse geometry with the specular component partially included and the ACBT employs 45°-0° geometry with the specular component excluded. Using both systems, one should be able to deduce if the change in reflectance of the specimen is due to changes in absorption, scattering, or surface structure. Changes in absorption and scattering would influence the data from both instruments in about the same way whereas changes in the specimen surface would influence the data differently. Changes in absorption could be more pronounced in selected portions of the spectrum whereas changes in scattering or surface should have a minor dependence on wavelength.

In the case of the GERS, air at different levels of relative humidity was passed throught the integrating cavity. Thus, the area of the specimen measured by the instrument was exposed to the conditions air while the measurement was being performed. The same was true for the ACBT except that the air was passed through the cylindrical opening in the instrument directly beneath the specimen opening. . . .

The data show small changes for the "white" papers while the dyed papers and the newsprint show more significant changes. The effects were generally greater with the ACBT than with the GERS suggesting that changes in surface characteristics with changing relative humidity is principally involved. It is interesting to note that the reflectance of the red paper increased at 450 nm with increasing moisture content and decreased at 550 and 500 nm. This effect was noted with both instrument and is probably attributable to changes in light absorption.

Colorimetric data obtained with the ACBT at the several levels of relative humidity are given in Table XIII. The E value represents the color difference between the first determination at 5% relative humidity and the subsequent results. Several samples show a E value greater than one with sample "H" over two.

Sample A (fluorescent) has a reflectance of 85.0% for the GERS at 400 nm and 55.8 for the ACBT. This large difference is related to the erroneous evaluation of the fluorescent component by the GERS.

It appears that reflectance of paper, especially dyed papers, is significantly affected by changes in moisture content. Indications for the samples tested are that changes in moisture content resulting from exposure to levels of relative humidity from 5 to 50% represent a reasonable limiting range for good accuracy.

Temperature

The web temperature would be higher for on-machine than off-machine testing. A study was performed to determine the effects of changing temperature on the reflectance of paper. The same paper samples (different specimens) evaluated in the moisture study were evaluated at four different temperatures. The GERS and the ACBT were employed because of their low level of illumination. Temperature at the surface of the specimen in the area exposed to the incident beam was determined with a 0.004-inch diameter wire chromel-alumel thermocouple. The junction was placed in contact with the paper surface. It is understood that differences in the absorption characteristics of the thermocouple and paper preclude the assumption that the paper surface and the junction temperature are the same when exposed to the incident radiation. However, when the temperature measurements were made, paper sample B was placed over the specimen opening in every case so that the relationship between junction and paper temperature should be fairly consistent for the different instruments. . . .

A reasonable upper limit on temperature, as indicated by these data would be about 40° C. If on-machine measurements are made at higher temperatures, the potential effects of temperature may need to be considered for comparison with off-machine optical data.

Fluorescence

Widespread use of fluorescent dyes has made the matter of fluorescence an important factor in the measurement of optical properties of paper. The fluorescent "whitening" agents used in the paper industry generally absorb strongly in the violet and ultraviolet regions of the spectrum and emit light at somewhat longer wavelengths in the violet and in the blue regions of the spectrum. For fluorescent dyes, in general, the region of absorption may extend from the short wavelengths (ultraviolet) to the region where light is emitted by the dye. Actually, there may be some overlapping of the absorption and emittance regions.

In the case of the fluorescent "whitening" agents, the ultraviolet light needed to excite dye is largely absorbed in the surface layers of the sheet. Thus, with fluorescence present, reflectance would be most influenced whereas transmittance would be only minimally affected. This has a pronounced effect on the calculation of $R_{oo}$ from $R_o$ and T.

Properly designed instrumentation should be employed where fluorescence is a factor (19).

Web Position

In all optical instruments, the position of the web must be fixed at the appropriate design point. In the calibration of an instrument with paper or other material, a web position will be indicated. The moving web should, of course, be at the calibration position. This is best accomplished by ensuring that the web is in contact with a reference surface. Through establishing such contact, it is possible to have the optical instrumentation on one side of the web properly placed with respect to web position. The other side, however, must be maintained at the proper spacing. Changes in instrument to web distance can introduce errors of significant magnitude. Two options are available; the apparatus to web spacing may be fixed, or the spacing may be measured and corrections of the results made for changes from the desired spacing. The former method is preferred whenever possible.

Web flutter is obviously undesirable. If web flutter, exists web position is not known. Similarly, vibration of the optical apparatus may influence the results.

Web Speed

Potential effects due to web speed depend on the nature of the time constants of the optical instruments. For a time varying signal, with linear photometric response of the instrument, and with slow response, an appropriate arithmetic average value might be expected. However, if the time varying signal is not symmetrical about the mean value, the instrument may not indicate the mean correctly whereas the off-machine instrument could. Thus, the reading could be speed dependent under some conditions of sheet variability and instrument design.

Calendering

All optical properties of paper are affected by calendering of the sheet. Hence, on-line measurements of final paper properties must be made after calendering. In the usual application of optical apparatus between the calender and the reel, the measurements would be obtained only a fraction of a second after the sheet leaves the calender. It seems likely that the sheet would be undergoing compression recovery during this period and for some time after calendering with the result that changes in the sheet thickness and surface smoothness would occur between the time the on-line optical measurements are made and some later time when off-machine optical measurements are made. The possible importance of such effects is not known. The fact that they may occur is recognized as one of the possible factors leading to lack of agreement between on-line and off-machine measured optical properties.

Stray Light

It is usually possible to design optical instrumentation with proper shielding from stray light. Obviously, such shielding is required, since appreciable error may occur if stray light is permitted to enter the measurement zone.

Dust and Dirt

All on-machine optical instrumentation should be designed to eliminate or minimize dust or dirt accumulations. Some contamination cannot be avoided and compensation for its effect must be developed through frequent calibration of the on-machine apparatus.

Instrument Temperature

The optical as well as electronic components of optical devices are temperature sensitive. Best design involves control of instrument temperature to values above the ambient temperature of the machine room with the web in running position. Compensation for temperature is also possible, but less desirable.

LITERATURE CITED

1. Van den Akker, J. A., Nolan, Phillip, and Wink, W. A., The Physical Basis of Standardization of Brightness Measurement, Paper Trade Journal, 114, No. 5: 34–40 (Jan. 29, 1942).
2. Van den Akker, J. A., Dearth, L. R. and Shillcox, W. M., Evaluation of Absolute Reflectance for Standardization Purposes, J. Opt. Soc. Am., Vol. 56, No. 2, 250–252, Feb. 1966. D. G. Goebel, B. P. Caldwell and H. K. Hammond, III, Use of an Auxiliary Sphere with a Spectrophotometer to Obtain Absolute Reflectance, J. Opt. Soc. Am., 56, 783 (1966).
3. Van der Akker, J. A., Standard Brightness, Color and Spectrophotometry with Emphasis on Recent Information, Tappi Vol. 48, No. 12 (Dec., 1965).
4. Report No. 8 of the American Paper and Pulp Association. Parts I and II. Adaptability of the G.E. Reflection Meter as a Color Analyzer. Part III. The Effect of Infrared Fluorescence Radiation upon "Brightness" Measurements obtained with the G.E. Reflection Meter. Instrumentation Studies XIII. Paper Trade Journal 104, No. 18:47–53; No. 19:51–63; No. 20:45–49 (May 6, 13, 20, 1937).
5. Höfert, H. J., and Loof, H., Calibration of the Photometric Scale of a Reflectance Photometer, Zeitschrift fur Instrumentenkunde, Bol. 72 (1964) No. 5.
6. Davis, M. N., A simple and Reliable Photo-Opacity Tester, Tech. Assoc. (TAPPI) Papers, Ser. 16. 16,277 (1933).
7. Hardy, A. C., Handbook of Colorimetry, The Technology Press, Massachusetts Institute of Technology, Cambridge, Mass. (1936).
8. Report No. 22TO: American Paper Institute Instrumentation Program, Part VI. Comparison of TAPPI and Printing Opacity Determined with Five Instruments, May 8, 1971.
9. Stokes, G. G. On the Intensity of the Light Reflected from or Transmitted through a Pile of Plates. Proc. Roy. Soc. London, 11, 545 (1860–1862).
10. Kubelka, P., and Munk, F., A. Tech. Physik 12:593–601 (1931).
11. Kubelka, P., New Contributions to the Optics of Intensely Light-Scattering Materials, JOSA, Vol. 38, No. 5 (May, 1948); errata, ibid, 38, 1067 (1948); ibid, 44, 330 (1954).
12. Van der Akker, J. A., Tappi 32, No. 11:498–501 (Nov. 1949).
13. Reflectance-Opacity Chart for White Backing of 0.89. (Judd, 1937).
14. Van der Akker, J. A., Tappi 50, No. 5:41A (May, 1967).
15. Official Recommendations of the International Commission on Illumination Publication CIE No. 15 (E-1.3.1) 1971.
16. Van der Akker, J. A., Chromaticity Limitations of the Best Physically Realizable Three-Filter Photoelectric Colorimeter. J. Opt. Soc. Am. 27, No. 12:401–407 (Dec. 1937).
17. McAdam, David L. "Color Measurement and Tolerances." Official Digest (Federation of Societies for Paint Technology). 37, 1487–1531 (1965). Chickering, JOSA, 57, 537 (1967).
18. Van der Akker, J. A. A Mechanical Integrator for Evaluating the Integral of the Product of Two Functions and its Application to the Computation of I.C.I. Color Specifications from Spectrophotometric Curves. J. Opt. Soc. Am. 29, No. 9:364–369 (Sep., 1939).
19. Grum, F. Instrumentation in Fluorescence Measurement, Journal of Color and Appearance, Vol. 1, No. 5:18–27 (Apr./May, 1972).

[The section entitled "Captions for the Figures" and FIGS. 1–7 of drawings are omitted]

Discussion of the Claimed Subject Matter

A basic conception of the present disclosure is crucially concerned with the art of paper manufacture wherein numerous grades and weights of paper are to be manufactured, and wherein access to the paper web for measurement of paper optical properties during the manufacturing process is restricted to a section between the calendering stack and the reel. The environment at this location has been detailed in the preceding section. By measuring two essentially independent optical parameters, for example measuring both the reflectance and transmittance with respect to incident light of the necessary spectral distribution, it is possible to calculate paper optical properties on the basis of existing theory with an essential independence of basis weight. The feasibility and effectiveness of this approach is confirmed in the preceding section.

Closely related to the foregoing is the conception of utilizing as nearly as practicable the optical response characteristics and geometry of existing instruments used in the paper industry, so as to achieve as close a correlation as possible with present off-line measurements of color and brightness, for example. Also of substantial significance is the conception of providing a rugged and compact temperature-stabilized instrument capable of reliable and accurate on-machine measurement of color, brightness and opacity.

The reduction to practice of these basic conceptions has included several sponsored projects at the Institute of Paper Chemistry as reflected by the preceding section and has included laboratory testing of a prototype device for accuracy and reliability on a wide range of paper samples, with careful comparison being made with corresponding measurements using standard laboratory instruments. Details of the life testing of the prototype unit over a ten-month period and the adaption of the device to reliable and stable operation on the paper machine have been included herein to document the practical implementation of the present invention. Because of the critical need for rapid calculation of paper optical properties in an on-machine device, the necessary computer programming has been developed and is fully disclosed herein. In spite of the substantial investments which have been made to secure expert assistance in implementing the conceptions, a period of time of over two years has been required to reach the stage of reduction to practice disclosed herein.

An important aspect of the disclosure relates to the measurement of the basis weight of the moving paper web concurrently with the simultaneous measurement of reflectance and transmittance values for essentially a common region of the web. Using the calculated value of infinite reflectance $R_{oo}$ (including the grade correction factor) and the value of transmittance T, for example, for the same sample region, along with a concurrently obtained, average value for basis weight, essentially accurate values of scattering coefficient s and the absorption coefficient k are obtained. Such coefficients will exhibit essential independence of any variations in the basis weight of the paper sheet material under these circumstances.

The measurement of both a reflectance and a transmittance value for a common sample region has an advantage over the measurement of two reflectance parameters under conditions such as found in the paper manufacturing process since the transmittance measurement is relatively insensitive to misalignment or tilting of the optical axis 515 of the backing assembly or lower sensing head 12, FIG. 3, relative to the optical axis 15 of the sensing head 11. This advantage is especially important for sheet material of relatively high opacity where two reflectance parameters would tend to be relatively close in value.

Generally the results of laboratory tests discussed herein are expected to be applicable to the on-line system. Thus the spread between values of $R_{oo}FC$ (See Table 3) obtained by the illustrated on-line system and the corresponding values of $AR_{oo}FC$ taken as standard should not differ by more than about plus or minus two points on a scale of zero to one hundred, prior to any grade correction, for a wide range of paper sheet materials of different color and basis weight.

The samples for which such accuracy was obtained in the laboratory included a range of basis weights of from 60 grams per square meter to 178 grams per square meter for white paper. Without the use of a correction factor, calculated $R_{oo}$ values which fell within two points of the measured value included samples of paper colored white (several tints), green, blue, canary, russett, ivory, gray and buff. Colors including pink, gold, salmon, and cherry required a significant correction factor for the $X_R$, $Y_C$, and $Y_A$ functions. All of the calculated $R_{oo}$ values involving the $X_B$ and Z functions fell within 0.77 units of the measured value on a scale of zero to 100, again without the use of any correction factor and regardless of color or basis weight.

DISCUSSION OF THE CLAIMED SUBJECT MATTER

The term quantitative measure of paper optical properties as used in the claims refers to output quantities of a numerical nature such as supplied by the on-line digital computer system 996, FIG. 6, programmed as explained herein with reference to FIGS. 7-20. Examples of such quantities are those indicated in block 990, FIG. 20; these quantities are identified with the corresponding conventional paper optical properties in Table 21.

The term on-machine optical monitoring device is intended generically and refers to the device 10, FIGS. 1 and 2, and other comparable devices for sensing two essentially independent optical response parameters such that a paper optical property is characterized prior to use of any correction factors with substantially improved accuracy in comparison to any characterization (prior to correction factors) of such paper optical property from either of such optical response parameters taken by itself. Such a monitoring device may be used as an aid to manual control of the paper making process or may be used as part of a closed loop automatic control system. Thus "monitoring" does not exclude active control in response to the output signals from the monitoring device.

Within the scope of the present subject matter, one or more of the following paper optical properties may be sensed; brightness, color, fluorescence, and/or opacity. Control of brightness and fluorescence offers a very substantial potential for cost reduction in the production of a significant range of paper types. Color control, on the other hand, may have important consequences regarding flexibility of manufacture, product uniformity, and grade change flexibility.

The value of on-line opacity control has already been demonstrated to a large degree in a prior closed loop analog opacity controller. In this installation, the average opacity across the web is controlled almost exactly at any given desired value. In previous manually controlled operations, the PKT (Pigmentary Potassium Titamate, $K_2O—6T_iO_2$ by du Pont) flow was set to some value chosen by the beater engineer and usually held to such value for the duration of the run of a given grade and weight. In the meantime, the paper opacity varied up and down, depending on process conditions at the time. Since the installation of the analog opacity controller, the opacity set point is adjusted rather than the PKT flow, thus holding opacity constant at the desired level. Instead of opacity, the PKT flow now varies up and down to compensate for other presently unavoidable process upsets resulting from variations in broke richness, PKT solids, dye usage, save-all efficiency, and other machine retention conditions. For a complete discussion of the installation of the analog opacity controller, reference is made to F. P. Lodzinski article "Experience With a Transmittance-Type On-Line Opacimeter for Monitoring and Controlling Opacity", *Tappi*, The Journal of The Technical Association of The Pulp and Paper Industry, Vol. 56, No. 2, February, 1973. This article of February, 1973 is incorporated herein by reference.

Existing on-line color meters have two serious disadvantages as follows:

1. Each measures a reflectance value ($R_g$) which is decidely different from that necessary for actual color and brightness characterizations. Off-line instruments, which adequately measure these properties, require that a pad of several thicknesses ($R_{oo}$) of the same paper be exposed to the light source aperture. Obviously, this is impossible with an on-line instrument, unless the far more inaccessible reel itself is tested. The use of $R_g$ instead of $R_{oo}$ requires very frequent off-line testing, and constant updating of an empirical calibration procedure to maintain adequate accuracy. A separate set of calibration parameters for each grade and weight is also required. Only in instances of extremely high opacity such as heavily coated, or heavily dyed colors where $R_g$ approaches $R_{oo}$, can the above problems be minimized to the point where accuracy becomes sufficient for control purposes.

2. Existing color instruments are not equipped to measure transmitted light which is much more sensitive to differences and, so far, the only commercially proven method for the continuous monitoring of opacity.

To assist in indicating the scope of the present disclosure, the substance of excerpts from an early conception record with respect to the present subject matter are set forth in the following paragraphs, headed "Proposal" and "Proposed Instrument Design" having reference to the defects of existing on-line color meters just discussed:

Proposal:

An instrument built to the general specifications disclosed in the following section headed "Proposed Instrument Design" avoids the above described defects and, at the same time, provides for a concise, but extremely versatile, nearly total optical property monitor and controller. Highly trained specialists in all fields required here, including paper optics, color theory, photometry, computers, and others, if needed are available. As an example, exact specifications for the filters, photocells, and light sources are essentially ready for manufacture now. Such specialists are also aware of factors important to optical characterization frequently ignored by commercial producers of optical instruments.

Proposed Instruments Design:

An instrument made up of two scanning sensing heads, one above and one below the moving paper web, and a dedicated computer with appropriate couplers for input and output, is envisioned. The bottom head would receive light transmitted through the sheet and subsequently analyzed for its X, Y, and Z tristimulus components. It would also contain a backing of some specified effective reflectance (possibly a black body of zero, or near zero, reflectance) located just ahead or behind (machine direction) of the transmitted light receptor compartment(s).

The upper head could contain the light source, as well as a reflected light receptor. The latter occurs after reflection from the moving web at a point just above the backing, on the bottom head and would also be analyzed for its X, Y, and Z tristimulus components. Both light receivers and, for that matter, the light source itself could be integrating cavities of a type. This would be one way to insure the uniform distribution of emitted, transmitted, and reflected light in the X-direction in addition to providing identical samples of light going to each photoelectric cell installed with filters within the cavities themselves. Thermostatically controlled heaters or coolers would likely be desirable for temperature control. The flux of the light source could be monitored or controlled by a third partial, or full, set of filter-photocell combinations. The availability of both the transmitted (T) and reflected ($R_g$) light signals described above allows for precise computation of the reflectance with an infinite backing ($R_{oo}$). It is the latter, $R_{oo}$ value, which is required to characterize color, brightness, and an index of fluorescence. In addition, it would eliminate the need for any grade corrections in measuring either printing or TAPPI opacity, both of which could be made available if desired.

A small, rather low cost, dedicated computer with appropriate interface equipment, could be used to receive all signals, compute all pertinent optical properties, and determine the signal for direct, closed loop control of:

a. 2–5 separate conventional dye additions;
b. fluroescent dye feed to the size press; and
c. PKT, $TiO_2$, or other slurry flow;

so that brightness, opacity, color (L, a,b) and fluorescence could be maintained almost exactly as chosen by, perhaps even a master computer, if desired.

Kubelka-Munk equations, quantitative color descriptions, and their inter-relationships, recently acquired wet end mathematical models, along with existing control theory, are all presently available in some form or other to convert the input signals from the scanning heads to optical measurements and flow feeds with which paper manufacturers are familiar. The combined mathematical technology above is also sufficient for adequate decoupling of this otherwise complicated information so that overlapped control is avoided.

Use of a dedicated computer would eliminate most of the electronics now associatd with optical measuring equipment. It could also be used to integrate results across the web and simplify and/or maintain calibration. The package would lend itself to rather universal application and minimize the time and effort on the part of the purchaser.

The key feature of this proposed instrument, which distinguishes it from existing on-line optical testers, is that it calls for the measurement of both transmitted and reflected light without undue complications. This, in turn, can cause a great deal of improvements regarding sensitivity, accuracy, flexibility, and thoroughness of a continuous optical property measuring device.

The following Table will serve to identify the computer symbols used in FIGS. 17–20 with the corresponding conventional symbols and terminology used in the text.

TABLE 2

| Identification of Computer Symbols Used in FIGS. 17-20 | | |
|---|---|---|
| Computer Symbol | Conventional Symbol | Conventional Term for Symbol |
| SGCF | GC(Table 3) | specific grade correction factor |
| RG | RD(Table 3) | Nominal reflectance of the diffuser window 135 |
| TD | $T_d$ | Nominal transmittance of the diffuser window 135 |
| RZERO (RZTABL) | $R_0$(Table 3) | reflectance with black body backing for each filter wheel position I equals zero through five. |
| T (TTABL) | T(Table 3) | Transmittance with black body backing for each filter wheel position I equals zero through five. |
| RINF (RITABL) | $R_\infty$(Table 3) | infinite backing reflectance for filter wheel positions I equals zero to five. |
| S (STABL) | S | scatter coefficient for each filter wheel position I equals zero through five. |
| K (KTABL) | K | absorption coefficient for each filter wheel position I equals zero through five. |
| ZFLUOR | — | fluorescent contribution to tristimulus Z reflectance |
| ZRINF | — | tristimulus Z infinite backing reflectance with fluorescence |
| XBRINF | — | tristimulus $X_B$ infinite backing reflectance with fluorescence |
| BRRINF | — | TAPPI brightness (see Table I in the first section of this Topic for spectral distribution of the first filter wheel position) |
| POPAC | $R_o/R_{oo}$ | printing opacity |
| YAR89 | $R_{.89}$ | tristimulus Y reflectance with .89 backing |
| TOPAC | $R_o/R_o.89$ | TAPPI opacity |
| XTRI | X | C.I.E. tristimulus coordinate X |
| YTRI | Y | C.I.E. tristimulus coordinate Y |
| ZTRI | Z | C.I.E. tristimulus coordinate Z |
| LH | L | Hunter coordinate L |
| AH, BH | a,b | Hunter coordinates a,b. |

Scope of the Early Conception of This Invention

Given the foregoing conception, it is considered that many modifications and variations will be apparent to those skilled in the art. The basic conception claimed herein is the sensing of two essentially independent optical response parameters of a single thickness relatively homogeneous sheet material such that any other desired parameter or paper optical property can be accurately calculated.

For the case of opacity measurement, for example, the present invention is particularly applicable to an optical system wherein system spectral response essentially simulates the C.I.E. tristimulus Y filter with either illuminant A or C and to near-white papers as explained in the Lodzinski Article of February, 1973 incorporated herein by reference.

DISCUSSION OF FURTHER OR ANTICIPATED MODIFICATIONS AND FURTHER INFORMATION RELATIVE TO THE PREFERRED EMBODIMENT

Changes Made to the On-machine System of FIGS. 1–6

1. Light source lamp terminals were connected to test tip jacks so that lamp voltage (at the lamp) can now be quickly measured without opening the case.

2. An easily removable doorway was cut from the top of the upper head case so that the photocell and amplifier gain circuits are much more accessible now. The photocell can now be easily removed and its 3/16" diameter aperture viewed directly from above without removing the case. This permits a quick check to see whether the two heads are properly aligned. The diffuser 276, FIG. 3, in the photocell aperture will be uniformly lighted when alignment is correct. Non-uniform illumination of this diffuser is quite apparent when the heads are improperly aligned.

3. A temperature sensitive resistor is located in the upper head adjacent to the photocell. Conductors are connected to lugs on the power supply panel so that such resistance measurements are easy to acquire. An empirically prepared chart is used to convert the resistance to temperature. Thus, an upper head temperature can be monitored from the remote power supply panel. (This temperature measuring device has been on the OMOD since it was first constructed.)

4. The upper head weighs 20 lbs. and the lower head $9\frac{3}{4}$ lbs. The weight of the mounting brackets are 7 and 5 lbs., respectively. (The compact size and light weight of these heads is an important advantage when it comes to providing means of installing and traversing across the web).

5. The reason we choose the 45°-0° geometry is because this geometry is used in the standard TAPPI brightness measurement. There is no standard TAPPI color test geometry at this time. It is considered that the 45°-0° geometry with the light plane in the machine direction is the proper geometry for color measurement as well. The reason for this is that most of our paper products where brightness and color are important are eventually used for written communications purposes. Consequently, they are viewed on a table top or desk with the human eye and light source approximating the 45°-0° geometry as employed in the OMOD. Moreover, the grain direction of the paper (grain long $8\frac{1}{2}\times 11$ letterhead for example) is such that this directional effect is also simulated by the OMOD. Diffuse viewing is impossible by the human eye and diffuse illumination is quite unlikely in most offices or places of paper use.

Anticipated Computer Program Changes

1. We plan to test each individual reading of transmittance and reflectance (T and R) and compare it to the previously smoothed values. The latest individual readings will not be used to update the smoothed average whenever a difference between the two is greater than X%. The value of X will remain flexible, but likely in the neighborhood of 5–10%. This subprogram will reject and flag bad data since the paper optical properties could hardly change faster than this between readings. An exception is the very beginning of a run; however, the heads are not put on sheet until the operation has settled down somewhat anyway. Only the startup of a run will need to be manual or feed forward as far as color, brightness, and opacity control is concerned.

2. Initialization of the smoothing algorithm of R and T will be made to occur only when a grade change occurs; i.e., whenever a new set of specific grade correction factors are entered into the computer memory. There should not be any need for re-initialization for any other reason. Even basis weight changes occur gradually enough to permit the use of the previously stored smoothed averages without serious difficulty. We may, however, consider the use of an operator command to re-initialize such algorithms if found desirable.

3. For the No. 6 paper machine (shown in FIGS. 1 and 2), the OMOD heads will be pushed completely off the web on the front side to allow the basis weight gauge (mounted side of the OMOD) to measure right up to the front edge. The program will, therefore, need to be modified to reject data acquired whenever this occurs. Since the head position will be known, from the basic weight profile monitoring system, such data can be left unused whenever the position "Y" or greater is reached.

It turns out that this particular situation provides a convenient means of servicing the OMOD. The traversing mechanism can be stopped when the OMOD heads are pushed beyond the web edge where they are quite accessible for examination, checking of standardization, etc.

CURRENT PROGRAM LISTING

GE-PAC 4020 Program Listing Characteristics

The following program listings are considered to be in conformity with the flow charts of FIGS. 8–20. The listing is provided by the General Electric PAC 4020 process control computer, and the following general discussion explains the GE-PAC 4020 program listing characteristics.

I. The first page contains the following unique information:
   A. Line 1—control statement, with time of day and activity.
   B. Lines 2 and 3 contain program identification numbers.
II. The remaining information is broken into three parts as follows:
   A. The three left-most columns of numbers consist of assembler-generated machine coding:
      1. The first column of numbers consists of the octal location, relative to the beginning of the program.
      2. The second column of numbers consists of the contents of the octal location in absolute form—the first two numbers signify the operation code; the third number signifies the index register, if any; and the remaining five numbers signify the absolute operand of the instruction.
      3. The third column of numbers consists of the contents of the octal location in relative form—it is identical to (2), except the five right-most numbers signify the relative operand from the location of the instruction.

B. The next eighty columns correspond to the symbolic instructions from which the assembler generated the machine coding.
1. Statements beginning with an asterick or "C" are comments only, with respectively a 6 or 7 in column seventy.
2. Other statements are divided as follows: label, if any; symbolic operation code; symbolic operand, if any; index register preceded by a comma, if any; comment, if any; and 6, 7 or 1 in column seventy.
3. The 6 in column seventy indicates a programmer-defined assembly language statement. The 7 in column seventy indicates a programmer-defined Fortran language statement. The 1 in column seventy indicates an assembler-defined assembly language statement, such as symbolic coding generated from a programmer-defined Fortran statement.
C. The right-most column contains the line sequence number of the printout.

Program Listing For Program Fourteen (FIGS. 8–16)

The following listing is presented to illustrate the extent of the programming effort to implement the flow charts of FIGS. 8–16. It will be observed that the implementation of these flow charts together with the changes previously indicated herein and any necessary debugging is within the routine skill of the art.

```
101014 COMPILE
         814030060    814030060                          IDN  000000                                                                    1
         814030060    814030060                                                                                                         1
                                                   CTABL   EQL  12                                                                      6
                                                   STTABL  EQL  28                                                                      6
                                                   RGTABL  EQL  44                                                                      6
                                                   VTABL   EQL  60                                                                      6
                                                   SGTABL  EQL  76                                                                      6
                                                   OUTABL  EQL  92                                                                      6
                                                   STABL   EQL  102                                                                     6
                                                   KTABL   EQL  110                                                                     6
                                                   RSTABL  EQL  118                                                                     6
                                                   MPAR    EQL  134                                                                     6

*PROG 14                                                                              6

*TURNED ON INITALLY BY TYPER-THEREAFTER ON 1 SEC. BY AUXTIMER =5                      6
 000000  00002100     00002100             E014    LDA  TIME                                                                            6
 000001  32002707     32002707                     STA  AUXTM+3                                                                         6

*LOAD FILEX STARTING ADDR. INTO INDEX REGISTER                                        6
 000002  16300414     16340412             EVERYL  LDX  FILEX,3                                                                         6

*LOAD PCW ADD OF LOOPS P+Q  FROM P.F. X4>P.REFLECT.CELL X5>Q TRANS.                   6
 000003  00300001     00300001                     LDA  1,3                                                                             6
 000004  32000004     32000004                     STA  4           P                                                                   6
 000005  00300002     00300002                     LDA  2,3                                                                             6
 000006  32000005     32000005                     STA  5           Q                                                                   6

*LOAD PCW:S OF LOOPS P+Q  + CHECK IF OFF SCAN                                         6
 000007  00400000     00400000                     LDA  0,4         P                                                                   6
 000010  05004727     05004727                     TOD  23                                                                              6
 000011  30000647     30040636                     BTR  TRNOFF                                                                          6
 000012  00500000     00500000                     LDA  0,5                                                                             6
 000013  05004727     05004727                     TOD  23                                                                              6
 000014  30000647     30040633                     BTR  TRNOFF                                                                          6

*SET UP AUXTIMER TO RE-RUN IN 1 SECOND                                                6
 000015  25030000     25030000                     IAI                                                                                  6
 000016  00002707     00002707                     LDA  AUXTM+3                                                                         6
 000017  11000406     11040367                     ADD  DLYTIM                                                                          6
 000020  32002707     32002707                     STA  AUXTM+3                                                                         6
 000021  25020000     25020000                     PAI                                                                                  6

*LOAD SLOWDOWN CTR. FROM X3 DECRLMENT IT BY ONE                                       6
 000022  00300004     00300004                     LDA  4,3                                                                             6
 000023  31002025     31002025                     SUB  ONE                                                                             6
 000024  66000027     66040003                     BZE  RESTOR                                                                          6

*STORE NEW COUNT BACK IN FILE X + RTN.TO RTMOS                                        6

000025  32300004     32300004                     STA  4,3                                                                             6
 000026  14000375     14040347                     BRU  RTNRTM                                                                          6

*RESTORE                                                                              6

*RESTOR SLOWDOWN COUNT TO INITAL VALUE                                                6
 000027  00300005     00300005             RESTOR  LDA  5,3                                                                             6
 000030  32300004     32300004                     STA  4,3                                                                             6
```

```
                                    *READ FILTER POSITION INDEX FROM FILE + INDEX BY 1        6
000031    00300006    00300006              LDA 6,3                                           6
000032    60000001    60000001              AKA 1                                             6
000033    32300006    32300006              STA 6,3                                           6

*IS INC >OR LESS THAN 6                                  6
000034    50000007    50000007              SKA 7                                             6
000035    05004727    05004727              TOD 23                                            6
000036    34000066    34040030              BTS LDDIDG          YES                           6

*SET LOST INDEX REFERENCE TEMP FLAG                       6
000037    40000001    40000001              LDK 1                                             6
000040    32000413    32040353              STA LIRFLG                                        6

*OUTPUT AN ALARM FOR STUCK FILTER                         6

*TEST IF DISK IS DOWN                                     6
000041    00002777    00002777              LDA DISCOF                                        6
000042    05004700    05004700              TOD 0                                             6
000043    34000061    34040016              BTS NOALRM                                        6

*PRINT MSG.                                               6
                                              PRINT 10                                        7
000044    40000051    40040005              LDK $10                                           1
000045    45004330    45004330              MAQ                                               1
000046    33000561    33000561              SPB $PRINT                                        1
000047    33000564    33000564              SPB $HLOUT                                        1

10      FORMAT ($ OMOD FILTER STUCK$)                    7
000050    14000061    14040011              BRU $M0                                           1
000051    40220000    40220000      $10     CON 0,40220000                                    1
000052    10047515    10047515              CON A,3, OM                                       1
000053    23642040    23642040              CON A,3,OD                                        1
000054    21444514    21444514              CON A,3,FIL                                       1
000055    25042522    25042522              CON A,3,TER                                       1
000056    10051524    10051524              CON A,3, ST                                       1
000057    25241513    25241513              CON A,3,UCK                                       1
000060    60077770    60077770              CON 0,60077770                                    1
000061    300000000   300000000     $M0     BSS 0                                             1
000061    16300414    16340333      NOALRM  LDX FILEX,3                                       6

*REINITILIZE SMOOTHED DATA K>7                            6
000062    40000007    40000007              LDK 7                                             6
000063    32300011    32300011              STA 9,3                                           6

*SET UP CYCLE COUNTER FOR 1 DUMMY DATA SET                6
000064    40000001    40000001              LDK 1                                             6
000065    32300012    32300012              STA 10,3                                          6

*LOAD DIGITAL INPUT STATUS WORK FOR GROUP /1400           6
000066    25051400    25051400      LDDIDG  IN /1400                                          6

*IS FILTER IN POSITION ZERO!                              6
000067    05004726    05004726              TOD 22                                            6
000070    30000123    30040033              BTR LOSTIX                                        6

*I>7 !                                                    6
000071    00300006    00300006              LDA 6,3                                           6
000072    50000007    50000007              SKA 7                                             6
000073    05004727    05004727              TOD 23                                            6
000074    30000120    30040024              BTR REFILT                                        6

*REINITILIZE SMOOTHED DATA K>7                            6
000075    40000007    40000007              LDK 7                                             6
000076    32300011    32300011              STA 9,3                                           6

*SET UP DUMMY CYCLE >1                                    6
000077    40000001    40000001              LDK 1                                             6
000100    32300012    32300012              STA 10,3                                          6

*OUTPUT SKIPPED FILTER MSG                                6
                                              PRINT 20                                        7
000101    40000106    40040005              LDK $20                                           1
000102    45004330    45004330              MAQ                                               1
000103    33000561    33000561              SPB $PRINT                                        1
000104    33000564    33000564              SPB $HLOUT                                        1
                                    20      FORMAT ($ OMOD SKIPPED FILTER $)                 7
000105    14000117    14040012              BRU $M1                                           1
000106    40250000    40250000      $20     CON 0,40250000                                    1
000107    10047515    10047515              CON A,3, OM                                       1
000110    23642040    23642040              CON A,3,OD                                        1
000111    24645511    24645511              CON A,3,SKI                                       1
000112    24050105    24050105              CON A,3,PPE                                       1
000113    21020106    21020106              CON A,3,D F                                       1
000114    22246124    22246124              CON A,3,ILT                                       1
000115    21251040    21251040              CON A,3,ER                                        1

000116    60077767    60077767              CON 0,60077767                                    1

CONTINUE                                        7
000117    300000000   300000000     $M1     BSS 0                                             1
000117    16300414    16340275              LDX FILEX,3                                       6

*REINITILIZE FILTER INDEX >0                              6
000120    77300006    77300006      REFILT  STZ 6,3                                           6

*RESET LOST INDEX FLAG                                    6
000121    77000413    77040272              STZ LIRFLG                                        6
000122    14000125    14040003              BRU SAVEIB                                        6
```

```
                                *IS LOST INDEX FLAG SET                                                6
000123   00000413   00040270    LOSTIX LDA LIRFLG                                                      6
000124   67000372   67040246          BNZ BENTER           YES                                         6

*NO-LOAD HEAD POSITION SCAN ONLY FILE ADD (129) FROM FILE INTO X7      6
000125   00300003   00300003    SAVEIB LDA 3,3                                                         6
000126   32000007   32000007          STA 7                                                            6

*IS HEAD STZ BIT 4 GROUP 1400 CLOSED!                                  6
000127   25051400   25051400          IN /1400                                                         6
000130   05004704   05004704          TOD 4                                                            6
000131   30000246   30040115          BTR CHKSTZ                                                       6

*IS HPOS LESS THAN MIN.POS,                                            6
000132   00700001   00700001          LDA 1,7                                                          6
000133   31300010   31300010          SUB 8,3                                                          6
000134   05004727   05004727          TOD 23                                                           6
000135   34000154   34040017          BTS STDPRG                                                       6

*IS STANDARDIZE IN PROG SET                                            6
000136   00300000   00300000          LDA 0,3                                                          6
000137   05004727   05004727          TOD 23                                                           6
000140   30000143   30040003          BTR CHKMIN           NO                                          6

*RESET STDZ IN PROGRESS                                                6
000141   05046027   05046027          SBK 23                                                           6
000142   32300000   32300000          STA 0,3                                                          6

*IS HPOS LESS THAN MIN.POS.                                            6
000143   00700001   00700001    CHKMIN LDA 1,7                                                         6
000144   31300010   31300010          SUB 8,3                                                          6
000145   05004727   05004727          TOD 23                                                           6
000146   30000165   30040017          BTR CKIEQ6                                                       6

*INITILIZE FILTERED TABLE INITILIZATION INDEX K>7 IN FILE X            6
000147   40000007   40000007          LDK 7                                                            6
000150   32300011   32300011          STA 9,3                                                          6

*INITILIZE TEMP FILTER CYCLE  CYCLE>1 SAVE IN FILE X                   6
000151   40000001   40000001          LDK 1                                                            6
000152   32300012   32300012          STA 10,3                                                         6
000153   14000372   14040217          BRU BENTER                                                       6

*IS STANDARDIZE IN PROGRESS BIT 23 SET!                                6
000154   00300000   00300000    STDPRG LDA 0,3                                                         6
000155   05004727   05004727          TOD 23                                                           6
000156   34000165   34040007          BTS CKIEQ6           YES                                         6

*NO-SET STDZ IN PROGRESS                                               6
000157   05046027   05046027          SBK 23                                                           6
000160   32300000   32300000          STA 0,3                                                          6

*INITILIZE TEMP. FILTER CYCLE INDEX TO 1 IN FILE X                     6
000161   40000001   40000001          LDK 1                                                            6
000162   32300012   32300012          STA 10,3                                                         6

*INITILIZE FILTERED TABLE INITILIZATION INDEX K>7                      6
000163   40000007   40000007          LDK 7                                                            6
000164   32300011   32300011          STA 9,3                                                          6

*IS THE INITILIZATION INDEX GREATER THAN 6 !                           6
000165   00300011   00300011    CKIEQ6 LDA 9,3                                                         6
000166   50000006   50000006          SKA 6                                                            6
000167   05004727   05004727          TOD 23                                                           6
000170   30000372   30040202          BTR BENTER                                                       6

*NO-IS IT EQUAL TO 6                                                   6
000171   67000200   67040007          BNZ LDALPH                                                       6

*IS THE CYCLE 0!OR MINUS                                               6
000172   00300012   00300012          LDA 10,3                                                         6
000173   66000200   66040005          BZE LDALPH                                                       6
000174   05004727   05004727          TOD 23                                                           6
000175   34000200   34040003          BTS LDALPH                                                       6
                                *NO-DECRIMENT CYCLE INDEX + SAVE BACK IN FILEX                         6
000176   50000001   50000001          SKA 1                                                            6
000177   32300012   32300012          STA 10,3                                                         6

*LOAD SMOOTHING CONSTANT FROM FILE                                     6
000200   00300013   00300013    LDALPH LDA 11,3                                                        6
000201   32000656   32040455          STA ALPHA                                                        6

*LOAD BASIS WT. FILE ADD + PUT FLOATED PV IN FILEX<122                 6
000202   00300007   00300007          LDA 7,3                                                          6
000203   32000006   32000006          STA 6                                                            6
000204   00600002   00600002          LDA 2,6                                                          6

000205   74020010   74020010          FLO 8                                                            6
000206   32300172   32300172          STA 122,3                                                        6

*INITILIZE LOOP INDEX J>0                                              6
000207   77000412   77040203          STZ JINX                                                         6

*IS LOOP J ON SCAN                                                     6
000210   00400000   00400000    LOOPJ LDA 0,4                                                          6
000211   05004727   05004727          TOD 23                                                           6
000212   30000275   30040063          BTR CHK2ND                                                       6
```

```
000213    00000412     00040177              *YES-LOAD STDZ. CORRECTION FACTOR FROM FILEX INTO C        6
000213    00000412     00040177              LDA JINX                                                   6
000214    11000003     11000003              ADD 3                                                      6
000215    32000006     32000006              STA 6                                                      6
000216    00600014     00600014              LDA CTABL,6                                                6
000217    32000654     32040435              STA CTABLE                                                 6

*LOAD PV FROM SCAN ONLY FILE(J)                            6
000220    00400001     00400001              LDA 1,4                                                    6
000221    32000007     32000007              STA 7                                                      6
000222    00700001     00700001              LDA 1,7                                                    6

*CONVERT TO ENGINEERING UNITS B1                           6
000223    31000410     31040165              SUB EIGHTH                                                 6
000224    45004414     45004414              DRA 12                                                     6
000225    65000407     65040162              DVD THRTY2                                                 6
000226    00000010     00000010              LDA /10                                                    6
000227    74020001     74020001              FLO 1                                                      6
000230    32000653     32040423              STA NCELL                                                  6

REAL NCELL,NFCELL                                          7

CCALC    CORRECT INPUT                                               7

NCELL=NCELL*CTABLE                                         7
000231    00000653     00040422              LDA NCELL                                                  1
000232    72000654     72040422              FMP CTABLE                                                 1
000233    32000653     32040420              STA NCELL                                                  1

CONTINUE                                                   7
000234    16300414     16340160              LDX FILEX,3                                                6
000235    00000412     00040155              LDA JINX                                                   6
000236    11000003     11000003              ADD 3                                                      6
000237    32000006     32000006              STA 6                                                      6

*K GREATER THAN ZERO                                       6
000240    00300011     00300011              LDA 9,3                                                    6
000241    66000243     66040002              BZE LDPREV                                                 6
000242    76000246     76040004              BNM CHKSTZ                                                 6

*LD PREV SMOOTHED VALUE FROM FILEX INTO TEMP PFCELL        6
000243    00600074     00600074     LDPREV   LDA VTABL,6                                                6
000244    32000657     32040413              STA PFCELL                                                 6
000245    14000253     14040006              BRU SMOALG                                                 6

*IS STANDARDIZE IN PROGRESS BIT SET                        6
000246    00300000     00300000     CHKSTZ   LDA 0,3                                                    6
000247    05004727     05004727              TOD 23                                                     6
000250    34000272     34040022              BTS LDPVJ                                                  6

*NO-MAKE PREV. SMOOTHED VALUE EQUAL TO NEW UNSMOOTHED INPUT 6
000251    00000653     00040402              LDA NCELL                                                  6
000252    32000657     32040405              STA PFCELL                                                 6

*SMOOTHING ALGORITHM                                       6
000253    300000000    300000000    SMOALG   BSS 0                                                      6

NFCELL=ALPHA*NCELL+(1.-ALPHA)*PFCELL                       7
000253    00000656     00040403              LDA ALPHA                                                  1
000254    72000653     72040377              FMP NCELL                                                  1
000255    32000652     32040375              STA $TEMP                                                  1
000256    00000651     00040373              LDA $FLCON                                                 1
000257    71000656     71040377              FSU ALPHA                                                  1
000260    72000657     72040377              FMP PFCELL                                                 1
000261    70000652     70040371              FAD $TEMP                                                  1
000262    32000655     32040373              STA NFCELL                                                 1

CONTINUE                                                   7
000263    16300414     16340131              LDX FILEX,3                                                6
000264    00000412     00040126              LDA JINX                                                   6
000265    11000003     11000003              ADD 3                                                      6
000266    32000006     32000006              STA 6                                                      6

*SAVE NEW SMOOTHED VALUE BACK IN FILEX                     6
000267    00000655     00040366              LDA NFCELL                                                 6
000270    32600074     32600074              STA VTABL,6                                                6
000271    14000275     14040004              BRU CHK2ND                                                 6

*LOAD PV FROM SCAN ONLY LOOP J FILE STORE IN FILEX STTABL(I,J)  6
000272    00700002     00700002     LDPVJ    LDA 2,7                                                    6
000273    74020001     74020001              FLO 1                                                      6
000274    32600034     32600034              STA STTABL,6                                               6

*HAS SECOND INPUT BEEN PROCESSED                           6
000275    00000412     00040115     CHK2ND   LDA JINX                                                   6
000276    67000304     67040006              BNZ KZERO                                                  6

*LOAD LOOP Q PCW PUT IN X4 + SET J INDEX TO ONE +RELOOP    6
000277    00300002     00300002              LDA 2,3                                                    6
000300    32000004     32000004              STA 4                                                      6

000301    40000001     40000001              LDK 1                                                      6
000302    32000412     32040110              STA JINX                                                   6
000303    14000210     14077705              BRU LOOPJ                                                  6
```

```
                                      *IS K > TO ZERO                                              6
000304   00300011   00300011          KZERO LDA 9,3                                                6
000305   66000313   66040006          BZE ISTAND                                                   6

*NO-IS IT LESS THAN 0                                        6
000306   05004727   05004727          TOD 23                                                       6
000307   34000372   34040063          BTS BENTER                                                   6

*NO-DECRIMENT INITIALIZATION COUNT + SAVE IN FILE X          6
000310   50000001   50000001          SKA 1                                                        6
000311   32300011   32300011          STA 9,3                                                      6
000312   14000372   14040060          BRU BENTER                                                   6

*IS STANDARDIZE IN PROG SET                                  6
000313   00300000   00300000          ISTAND LDA 0,3                                               6
000314   05004727   05004727          TOD 23                                                       6
000315   30000372   30040055          BTR BENTER                                                   6

*RESET STDZ BIT + SAVE IN FILEX                              6
000316   05045027   05045027          RBK 23                                                       6
000317   32300000   32300000          STA 0,3                                                      6

*INITILIZE TEMP JCOUNT 0                                     6
000320   77000411   77040071          STZ JCOUNT                                                   6

*INITILIZE TEMP.COUNT ICOUNT>0                               6
000321   77002660   77002660          INITIO STZ ICOUNT                                            6

*LOAD CORR.CONST.FROM FILEX STTABL(ICOUNT,JCOUNT)INTO TEMP RG 6
000322   00000411   00040067          LOCORR LDA JCOUNT                                            6
000323   11002660   11002660          ADD ICOUNT                                                   6
000324   11000003   11000003          ADD 3                                                        6
000325   32000004   32000004          STA 4                                                        6
000326   00400166   00400166          LDA RSTABL,4                                                 6
000327   32000661   32040332          STA RG                                                       6

*LOAD OFF SHEET VALUES FROM FILEX STTABL(ICOUNT,JCOUNT)INTO TEMP ST 6
000330   00400034   00400034          LDA STTABL,4                                                 6
000331   32000662   32040331          STA ST                                                       6

*CALC CORR. FACTOR                                           6

C=RG/ST                                                      7
000332   00000661   00040327          LDA RG                                                       1
000333   73000662   73040327          FDV ST                                                       1
000334   32000660   32040324          STA C                                                        1
                                      CONTINUE                                                     7

* IF REFL.(JCOUNT>0) MULT CTABL(I,J) BY EMPIRICAL CORR. CONSTANT IN 6
                                      * MPAR<5, IF TRANSMITTANCE (JCOUNT>1), MULT. BY MPAR<6.      6
000335   00000411   00040054          LDA JCOUNT                                                   6
000336   31002026   31002026          SUB TWO                                                      6
000337   05004727   05004727          TOD 23                                                       6
000340   30000375   30040035          BTR RTNRTM                                                   6
000341   00000411   00040050          LDA JCOUNT                                                   6
000342   32000004   32000004          STA 4                                                        6
000343   04400417   04440054          XEC CORCAL,4                                                 6
000344   32000663   32040317          STA CORR                                                     6

C=C*CORR                                                     7
000345   00000660   00040313          LDA C                                                        1
000346   72000663   72040315          FMP CORR                                                     1
000347   32000660   32040311          STA C                                                        1

CONTINUE                                                     7
000350   16300414   16340044          LDX FILEX,3                                                  6
000351   00000411   00040040          LDA JCOUNT                                                   6
000352   11002660   11002660          ADD ICOUNT                                                   6
000353   32000004   32000004          STA 4                                                        6

*SAVE CORR FACTOR IN FILEX CTABL(ICOUNT,JCOUNT)>C            6
000354   00000660   00040304          LDA C                                                        6
000355   32400014   32400014          STA CTABL,4                                                  6

*IS ICOUNT LESS THAN SIX!                                    6
000356   00002660   00002660          LDA ICOUNT                                                   6
000357   50000005   50000005          SKA 5                                                        6
000360   05004727   05004727          TOD 23                                                       6
000361   30000365   30040004          BTR CKJCNT                                                   6

*INX,ICOUNT BY 1                                             6
000362   60000001   60000001          AKA 1                                                        6
000363   32002660   32002660          STA ICOUNT                                                   6
000364   14000322   14077736          BRU LOCORR                                                   6

*IS JCOUNT GREATER THAN ZERO                                 6
000365   00000411   00040024          CKJCNT LDA JCOUNT                                            6
000366   67000372   67040004          BNZ BENTER                                                   6
000367   60000001   60000001          AKA 1                                                        6
000370   32000411   32040021          STA JCOUNT                                                   6
000371   14000321   14077730          BRU INITIO                                                   6

*CLOSE FILTER ADVANCE SOLENOID DRIVE CONTACTS MOMENTARILY    6
```

```
000372   00000416    00040024              *CALL TIMED OUTPUT RTMOS TIMED OUTPUT FOR .5 SEC.      6
000373   42000415    42040022        BENTER LDA  AREG                                             6
000374   33000445    33000445               LDQ  TIMEQ                                            6
                                            SPB  MORC04                                           6

*SET UP FOR AUXTIME TURNON IN ONE SEC.                      6
000375   00002707    00002707        RTNRTM LDA  AUXTM+3                                          6
000376   31002100    31002100               SUB  TIME                                             6
000377   05004527    05004527               SOD  23                                               6
000400   34000002    34077402               BTS  EVERYL                                           6
000401   05046027    05046027               SBK  23                                               6
000402   32000404    32040002               STA  *+2                                              6
000403   33000401    33000401               SPB  DELC01                                           6
000404   300000001   300000001              BSS  1                                                6
000405   14000002    14077375               BRU  EVERYL                                           6
000406   00000020    00000020        DLYTIM CON  G,SECND*4                                        6
                                     DISCOF EQL  /2777          TEMP-T1L-RE-ASSEMBLY              6
000407   00006200    00006200        THRTY2 CON  D,3200                                           6
000410   06200000    06200000        EIGHTH CON  D,800B12                                         6
000411   00000000    00000000        JCOUNT CON  0,0                                              6
000412   00000000    00000000        JINX   CON  0,0                                              6
000413   00000000    00000000        LIRFLG CON  0,0                                              6
000414   00063200    00063200        FILEX  CON  0,63200                                          6
000415   00017000    00017000        TIMEQ  CON  D,30B15                                          6
000416   00000000    00000000        AREG   CON  0,0                                              6
000417   00000213    00000213        CORCAL LDA  MPAR+5                                           6
000420   00000214    00000214               LDA  MPAR+6                                           6
000421   300000226   300000226        FILEX1 BSS  150                                             6
000647   33000404    33000404        TRNOFF SPB  OFFC01         TURN PROG OFF                     6
000650   10000000    10077130               PRG  0,1,0,E014,0                                     6

END                                                   7
000651   300000000   300000000              BSS  0                                                 1
000651   300000000   300000000        $FXCON BSS  0                                                1
000651   20600000    20600000         $FLCON CON  0,20600000                                      1
000652   300000000   300000000        $ST3RU BSS  0                                                1
000652   300000001   300000001        $TEMP  BSS  1                                                1
000653   300000001   300000001        NCELL  BSS  1                                                1
000654   300000001   300000001        CTABLE BSS  1                                                1
000655   300000001   300000001        NFCELL BSS  1                                                1
000656   300000001   300000001        ALPHA  BSS  1                                                1
000657   300000001   300000001        PFCELL BSS  1                                                1
000660   300000001   300000001        C      BSS  1                                                1
000661   300000001   300000001        RG     BSS  1                                                1
000662   300000001   300000001        ST     BSS  1                                                1
000663   300000001   300000001        CORR   BSS  1                                                1

*PROGRAM END.   0 FORTRAN ERRORS                             1

*00000000   *00000000            END                                                          1

0 ASSEMBLY ERRORS.
                                     000664 PROGRAM OCTAL SIZE.
                                     000314 EQL TABLE OCTAL SIZE.
```

Program Listing For Program Forty-Two (FIGS. 17-20)

The following listing is presented to illustrate the extent of the programming effort to implement the flow charts of FIGS. 17-20. It will be observed that the implementation of these flow charts together with the changes previously indicated herein and any necessary debugging is within the routine skill of the art.

```
103756 COMPILE
         814030060   814030060           IDN 000000                                                1
         814030060   814030060                                                                     1

EQUIVALENCE(POPAC,OUTABL(1)),(YAR89,OUTABL(2)),(CYCLE,    7
                                        1FILEX(11)),(BH,   MPAR(5)),                               7
                                        1(TOPAC,OUTABL(3)),(XTRI,OUTABL(4)),(YTRI,OUTABL(5)),      7
                                        2(ZTRI,OUTABL(6)),(LH,OUTABL(7)),(AH,OUTABL(8)),           7
                                        3(BH,OUTABL(9)),(BRRINF,OUTABL(10))                        7

INTEGER CYCLE                                             7

REAL K,LNAX,KTABL,MPAR,LH                                 7

NX = 0                                                    7
000000   00001527    00041527             LDA  $FXCON                                              1
000001   32001560    32041557             STA  NX                                                  1

DIMENSION TMPSAV (128)                                    7

DIMENSION FILEX(0/11)                                     7
```

```
                              DIMENSION RZTABL(0/7),TTABL(0/7),RITABL(0/7)                  7
                              DIMENSION STABL(0/7),KTABL(0/7),MPAR(0/6)                     7
                             1,STTABL(0/7,0/1),RGTABL(0/7,0/1),VTABL(0/7,0/1),SGTABL(0/7,0/1)7
                             2,OUTABL(0/9),RSTABL(0/7,0/1)                                  7
                                      GO TO 5                                               7
 000002   14000071    14040067        BRU $5                                                1
                              C GET TABLE OF SPECIFIC GRADE CORR. FACTORS FROM BULK TABLE.  7
                                      CALL GET TABLE (NX,TMPSAV,IRR)                        7
 000003   33000514    33000514        SPB GETTAB                                            1
 000004   07301560    07341554        LXK NX,3                                              1
 000005   07301606    07341601        LXK TMPSAV,3                                          1
 000006   07301561    07341553        LXK IRR,3                                             1

IF (IRR) 11,20,11                                     7
 000007   00001561    00041552        LDA IRR                                               1
 000010   05004727    05004727        TOD 23                                                1
 000011   34000015    34040004        BTS $11                                               1
 000012   05004670    05004670        TZE                                                   1

000013   34000032    34040017        BTS $20                                               1
 000014   14000015    14040001        BRU $11                                               1

11      PRINT (1)31                                           7
 000015   40000023    40040006    $11 LDK $31                                               1
 000016   45004330    45004330        MAQ                                                   1
 000017   00001530    00041511        LDA $FXCON+1                                          1
 000020   33000561    33000561        SPB $PRINT                                            1
 000021   33000564    33000564        SPB $HLOUT                                            1

31      FORMAT ($ OMOD DT $)
 000022   14000030    14040006        BRU $MO                                               1
 000023   40110000    40110000    $31 CON 0,40110000                                        1
 000024   10047515    10047515        CON A,3, OM                                           1
 000025   23642040    23642040        CON A,3,OD                                            1
 000026   21052040    21052040        CON A,3,DT                                            1
 000027   60077773    60077773        CON 0,60077773                                        1

STOP                                                  7
 000030   33000405    33000405    $MO SPB OFFC02                                            1
 000031   10000000    10000000        PRG 0,1,0,0,0                                         1

20      CONTINUE                                              7
 000032   300000000   300000000   $20 BSS 0                                                 1

C COPY PERM. CORE FILE AT /63200 INTO PROG. WORKING AREA AT FILEX1  7
 000032   16301526    16341474        LDX FILADD,3                                          6
 000033   40000226    40000226        LDK 150                                               6
 000034   32000005    32000005        STA 5                                                 6
 000035   00002023    00002023        LDA ZERO                                              6
 000036   32000004    32000004        STA 4                                                 6
 000037   00300000    00300000    NOTDON LDA 0,3                                            6
 000040   32401102    32441042        STA FILEX1,4                                          6
 000041   26300001    26300001        INX 1,3                                               6
 000042   26400001    26400001        INX 1,4                                               6
 000043   06000005    06000005        DMT 5                                                 6
 000044   34000037    34077773        BTS NOTDON                                            6

*GET INC TO CONSTANT TABLE FROM OPERATOR ENTERED MOD.FILE     6
 000045   16401331    16441264        LDX MOD,4                                             6
 000046   00400001    00400001        LDA 1,4                                               6
 000047   50000010    50000010        SKA 8                  TEST FOR GRADE INCREMENT IN LIMITS  6
 000050   05004727    05004727        TOD 23                                                6
 000051   30000054    30040003        BTR *+3                                               6
 000052   05000000    05000000        LDZ                                                   6
 000053   14000055    14040002        BRU *+2                                               6
 000054   00400001    00400001        LDA 1,4                                               6

*MULTIPLY BY 16 TO GET INCRIMENT                              6
 000055   05014047    05014047        SRA 7                                                 6

000056   32000004    32000004        STA 4                                                 6

C OVERLAY SPECIFIC GRADE CORR. FACTOR TABLE IN WORKING AREA   7

C AT FILEX1<76 WITH 16 WORD TABLE SELECTED BY OPERATOR ENTERED NO. 7
 000057   00025177    00025177        LDA FIFTEN                                            6
 000060   32000003    32000003        STA 3                                                 6
 000061   00002023    00002023        LDA ZERO                                              6
 000062   32000005    32000005        STA 5                                                 6
 000063   00401606    00441523    RELOOP LDA TMPSAV,4                                       6
 000064   32501216    32541132        STA SGTABL,5                                          6
 000065   26400001    26400001        INX 1,4                                               6
 000066   26500001    26500001        INX 1,5                                               6
 000067   06000003    06000003        DMT 3                                                 6
 000070   34000063    34077773        BTS RELOOP                                            6

5       CONTINUE                                              7
 000071   300000000   300000000   $5  BSS 0                                                 1

C CHECK IF CYCLE(NO. OF FILTER WHEEL REV. REQUIRED FOR NEW CALC.)  7
                              CHAS BEEN COUNTED DOWN TO ZERO BY PROG. 14.                   7
                                      IF(CYCLE)10,10,120                                    7
```

```
000071   00001114   00041023         LDA CYCLE                                                              1
000072   05004727   05004727         TOD 23                                                                 1
000073   34000077   34040004         BTS $10                                                                1
000074   05004670   05004670         TZE                                                                    1
000075   34000077   34040002         BTS $10                                                                1
000076   14001100   14041002         BRU $120                                                               1

C SET UP J>1 TO INDEX TRANS. PARAMETERS.                                7

10    J=1                                                                 7
000077   00001530   00041431      $10 LDA $FXCON+1                                                          1
000100   32001562   32041462         STA J                                                                  1

I=0                                                                 7
000101   00001527   00041426         LDA $FXCON                                                             1
000102   32001563   32041461         STA I                                                                  1

C LOAD TRANSMITTANCE SPECIFIC GRADE CORR. FOR ITH FILTER                   7

15    SGCF=SGTABL(I,J)                                                    7
000103   00001562   00041457      $15 LDA J                                                                 1
000104   45004330   45004330         MAQ                                                                    1
000105   11001563   11041456         ADD I                                                                  1
000106   55001531   55041423         MPY $FXCON+2                                                           1
000107   45006467   45006467         DLA 23                                                                 1
000110   32001555   32041445         STA $TEMP                                                              1

000111   16301555   16341444         LDX $TEMP,3                                                            1
000112   00301216   00341104         LDA SGTABL,3                                                           1
000113   32001564   32041451         STA SGCF                                                               1

C LOAD DIFFUSOR TRANS. CONST. FROM RGTABL FOR ITH FILTER INTO TD.          7

TD=RGTABL(I,J)                                                      7
000114   00001562   00041446         LDA J                                                                  1
000115   45004330   45004330         MAQ                                                                    1
000116   11001563   11041445         ADD I                                                                  1
000117   55001531   55041412         MPY $FXCON+2                                                           1
000120   45006467   45006467         DLA 23                                                                 1
000121   32001555   32041434         STA $TEMP                                                              1
000122   16401555   16441433         LDX $TEMP,4                                                            1
000123   00401156   00441033         LDA RGTABL,4                                                           1
000124   32001565   32041441         STA TD                                                                 1

C LOAD SMOOTHED AND STANDARDIZE CORRECTED TRANS. RATIO INTO TDP.           7

TDP=VTABL(I,J)                                                      7
000125   00001562   00041435         LDA J                                                                  1
000126   45004330   45004330         MAQ                                                                    1
000127   11001563   11041434         ADD I                                                                  1
000130   55001531   55041401         MPY $FXCON+2                                                           1
000131   45006467   45006467         DLA 23                                                                 1
000132   32001555   32041423         STA $TEMP                                                              1
000133   16501555   16541422         LDX $TEMP,5                                                            1
000134   00501176   00541042         LDA VTABL,5                                                            1
000135   32001566   32041431         STA TDP                                                                1

C CORRECT TDP FOR SPECIFIC GRADE.                                          7

TDP=TDP*SGCF                                                        7
000136   00001566   00041430         LDA TDP                                                                1
000137   72001564   72041425         FMP SGCF                                                               1
000140   32001566   32041426         STA TDP                                                                1

C SET UP J>0 FOR REFLECTANCE PARAMETERS.                                   7

J=0                                                                 7
000141   00001527   00041366         LDA $FXCON                                                             1
000142   32001562   32041420         STA J                                                                  1

C LOAD BACKING PLATE REFLECTANCE FROM RGTABL INTO RG FOR ITH FILTER.       7

RG=RGTABL(I,J)                                                      7
000143   00001562   00041417         LDA J                                                                  1
000144   45004330   45004330         MAQ                                                                    1
000145   11001563   11041416         ADD I                                                                  1
000146   55001531   55041363         MPY $FXCON+2                                                           1

000147   45006467   45006467         DLA 23                                                                 1
000150   32001555   32041405         STA $TEMP                                                              1
000151   16601555   16641404         LDX $TEMP,6                                                            1
000152   00601156   00641004         LDA RGTABL,6                                                           1
000153   32001567   32041414         STA RG                                                                 1

C LOAD REFLECTANCE SPECIFIC GRADE CORR. FACTOR FOR ITH FILTER.             7

SGCF=SGTABL(I,J)                                                    7
000154   00001562   00041406         LDA J                                                                  1
000155   45004330   45004330         MAQ                                                                    1
000156   11001563   11041405         ADD I                                                                  1
000157   55001531   55041352         MPY $FXCON+2                                                           1
000160   45006467   45006467         DLA 23                                                                 1
000161   32001555   32041374         STA $TEMP                                                              1
000162   16301555   16341373         LDX $TEMP,3                                                            1
000163   00301216   00341033         LDA SGTABL,3                                                           1
000164   32001564   32041400         STA SGCF                                                               1

C LOAD SMOOTHED AND STANDARDIZE CORRECTED REFLEC. RATIO INTO R.            7
```

```
                                              R=VTABL(I,J)                              7
000165   00001562   00041375         LDA  J                                             1
000166   45004330   45004330         MAQ                                                1
000167   11001563   11041374         ADD  I                                             1
000170   55001531   55041341         MPY  $FXCON+2                                     1
000171   45006467   45006467         DLA  23                                            1
000172   32001555   32041363         STA  $TEMP                                         1
000173   16401555   16041362         LDX  $TEMP,4                                       1
000174   00401176   00441002         LDA  VTABL,4                                       1
000175   32001570   32041373         STA  R                                             1

C CORRECT R FOR SPECIFIC GRADE.                     7

R=R*SGCF                                  7
000176   00001570   00041372         LDA  R                                             1
000177   72001564   72041365         FMP  SGCF                                          1
000200   32001570   32041370         STA  R                                             1

C CALC. RZERO FOR ITH FILTER.                        7

RZERO=(R-RG*(TDP/TD)**2)/(1.-(RG*TDP/TD)**2)  7
000201   00001566   00041365         LDA  TDP                                           1
000202   73001565   73041363         FDV  TD                                            1
000203   32001555   32041352         STA  $TEMP                                         1
000204   00001567   00041363         LDA  RG                                            1
000205   72001566   72041361         FMP  TDP                                           1
000206   73001565   73041357         FDV  TD                                            1
000207   32001556   32041347         STA  $TEMP+1                                       1
000210   00001532   00041322         LDA  $FXCON+3                                      1
000211   74020027   74020027         FLO  23                                            1
000212   33002036   33041624         SPB  XXXEXP                                        1
000213   00001556   00041343         LDA  $TEMP+1                                       1
000214   71001542   71041326         FSU  $FLCON                                        1
000215   32001557   32041342         STA  $TEMP+2                                       1
000216   00001532   00041314         LDA  $FXCON+3                                      1
000217   74020027   74020027         FLO  23                                            1
000220   33002036   33041616         SPB  XXXEXP                                        1
000221   00001555   00041334         LDA  $TEMP                                         1
000222   72001567   72041345         FMP  RG                                            1
000223   71001570   71041345         FSU  R                                             1
000224   73001557   73041333         FDV  $TEMP+2                                       1
000225   32001571   32041344         STA  RZERO                                         1

C CALC. TRANSMITTANCE T FOR ITH FILTER.              7

T=(TDP*(1.-RG*R))/(TD*(1.-(RG*TDP/TD)**2))  7
000226   00001567   00041341         LDA  RG                                            1
000227   72001566   72041337         FMP  TDP                                           1
000230   73001565   73041335         FDV  TD                                            1
000231   32001555   32041324         STA  $TEMP                                         1
000232   00001532   00041300         LDA  $FXCON+3                                      1
000233   74020027   74020027         FLO  23                                            1
000234   33002036   33041602         SPB  XXXEXP                                        1
000235   00001555   00041320         LDA  $TEMP                                         1
000236   71001542   71041304         FSU  $FLCON                                        1
000237   72001565   72041326         FMP  TD                                            1
000240   32001556   32041316         STA  $TEMP+1                                       1
000241   00001567   00041326         LDA  RG                                            1
000242   72001570   72041326         FMP  R                                             1
000243   71001542   71041277         FSU  $FLCON                                        1
000244   72001566   72041322         FMP  TDP                                           1
000245   73001556   73041311         FDV  $TEMP+1                                       1
000246   32001572   32041324         STA  T                                             1

C CALC. INTERM. VARIABLE AI                          7

AI=(1.0+RZERO**2-T**2)/(2.0*RZERO)        7
000247   00001543   00041274         LDA  $FLCON+1                                      1
000250   72001571   72041321         FMP  RZERO                                         1
000251   32001555   32041304         STA  $TEMP                                         1
000252   00001532   00041260         LDA  $FXCON+3                                      1
000253   74020027   74020027         FLO  23                                            1
000254   33002036   33041562         SPB  XXXEXP                                        1
000255   00001571   00041314         LDA  RZERO                                         1
000256   70001542   70041264         FAD  $FLCON                                        1
000257   32001556   32041277         STA  $TEMP+1                                       1
000260   00001532   00041252         LDA  $FXCON+3                                      1
000261   74020027   74020027         FLO  23                                            1
000262   33002036   33041554         SPB  XXXEXP                                        1

000263   00001572   00041307         LDA  T                                             1
000264   71001556   71041272         FSU  $TEMP+1                                       1
000265   73001555   73041270         FDV  $TEMP                                         1
000266   05004670   05004670         TZE                                                1
000267   34000271   34040002         BTS  *+2                                           1
000270   05047027   05047027         CBK  23                                            1
000271   32001573   32041302         STA  AI                                            1

C CALC. INTERM. VARIABLE BI                          7

BI=SQRTF(AI**2-1)                         7
000272   00001532   00041240         LDA  $FXCON+3                                      1
000273   74020027   74020027         FLO  23                                            1
000274   33002036   33041542         SPB  XXXEXP                                        1
000275   00001573   00041276         LDA  AI                                            1
000276   32001555   32041257         STA  $TEMP                                         1
000277   00001530   00041231         LDA  $FXCON+1                                      1
000300   74020027   74020027         FLO  23                                            1
```

```
000301   71001555   71041254              FSU $TEMP                                              1
000302   05004670   05004670              TZE                                                    1
000303   34000305   34040002              BTS *+2                                                1
000304   05047027   05047027              CBK 23                                                 1
000305   33002037   33041532              SPB SQRTF                                              1
000306   32001574   32041266              STA BJ                                                 1
```

C CALC. REFLECTANCE WITH INFINITE BACKING RINF>AI-BI                                              7

```
                                          RINF=AI-BI                                             7
000307   00001573   00041264              LDA AI                                                 1
000310   71001574   71041264              FSU BI                                                 1
000311   32001575   32041264              STA RINF                                               1
```

C CALC. ARG. OF LOG FUNCTION, AX                                                                  7

```
                                          AX=(BI+SQRTF(BI*BI+T*T))/(T*(BI+AI))                   7
000312   00001574   00041262              LDA BI                                                 1
000313   72001574   72041261              FMP BI                                                 1
000314   32001555   32041241              STA $TEMP                                              1
000315   00001572   00041255              LDA T                                                  1
000316   72001572   72041254              FMP T                                                  1
000317   70001555   70041236              FAD $TEMP                                              1
000320   33002037   33041517              SPB SQRTF                                              1
000321   32001556   32041235              STA $TEMP+1                                            1
000322   00001574   00041252              LDA BI                                                 1
000323   70001573   70041250              FAD AI                                                 1
000324   72001572   72041246              FMP T                                                  1
000325   32001557   32041232              STA $TEMP+2                                            1
000326   00001574   00041246              LDA BI                                                 1
000327   70001556   70041227              FAD $TEMP+1                                            1
000330   73001557   73041227              FDV $TEMP+2                                            1
000331   32001576   32041245              STA AX                                                 1
```

C CALC. NAT. LOG OF AX                                                                            7

```
                                          LNAX=LOGF(AX)                                          7
000332   00001576   00041244              LDA AX                                                 1
000333   33002040   33041505              SPB LOGF                                               1
000334   32001577   32041243              STA LNAX                                               1
000335   16601111   16640554              LDX FILEX1+7,6                                         6
000336   00600001   00600001              LDA 1,6                                                6
000337   74020010   74020010              FLO 8                                                  6
000340   32001314   32040754              STA BW                                                 6
```

C CALC. SCATTER COEF S PER LB. BASIS WT.                                                          7

```
                                          S=LNAX/(BI*BW)                                         7
000341   00001574   00041233              LDA BI                                                 1
000342   72001314   72040752              FMP BW                                                 1
000343   32001555   32041212              STA $TEMP                                              1
000344   00001577   00041233              LDA LNAX                                               1
000345   73001555   73041210              FDV $TEMP                                              1
000346   32001600   32041232              STA S                                                  1
```

C CALC. ABSORPTION COEF. K PER LB. BASIS WT.                                                      7

```
                                          K=S*(AI-1.)                                            7
000347   00001573   00041224              LDA AI                                                 1
000350   71001542   71041172              FSU $FLCON                                             1
000351   72001600   72041227              FMP S                                                  1
000352   32001601   32041227              STA K                                                  1
```

C SAVE RZERO, T, RINF IN TEMPORARY ARRAYS.                                                        7

```
                                          RZTABL(I)=RZERO                                        7
000353   00001571   00041216              LDA RZERO                                              1
000354   16501563   16541207              LDX I,5                                                1
000355   32502006   32541431              STA RZTABL,5                                           1

TTABL(I)=T                                             7
000356   00001572   00041214              LDA T                                                  1
000357   32502016   32541437              STA TTABL,5                                            1

RITABL(I)=RINF                                         7
000360   00001575   00041215              LDA RINF                                               1
000361   32502026   32541445              STA RITABL,5                                           1
```

C SAVE S AND K IN FILEX1 TABLES

```
                                          STABL(I)=S                                             7
000362   00001600   00041216              LDA S                                                  1

000363   32501250   32540665              STA STABL,5                                            1

KTABL(I)=K                                             7
000364   00001601   00041215              LDA K                                                  1
000365   32501260   32540673              STA KTABL,5                                            1

IF(I-6)30,60,60                                       7
000366   00001563   00041175              LDA I                                                  1
000367   31001533   31041144              SUB $FXCON+4                                           1
000370   05004727   05004727              TOD 23                                                 1
000371   34000375   34040004              BTS $30                                                1
000372   05004670   05004670              TZE                                                    1
000373   34000403   34040010              BTS $60                                                1
000374   14000403   14040007              BRU $60                                                1
```

```
000375   00001530   00041133        30    J=1
000376   32001562   32041164        $30   LDA $FXCON+1
                                          STA J

I=I+1
000377   00001563   00041164              LDA I
000400   11001530   11041130              ADD $FXCON+1
000401   32001563   32041162              STA I

GO TO 15
000402   14000103   14077501              BRU $15

C CALC DIFF. IN Z REFLECT. WITH AND WITHOUT FLUOR + MULT. BY IMP.CON.

60    ZFLUOR=(VTABL(6,0)-VTABL(3,0))*MPAR(0)
000403   00001204   00040601        $60   LDA VTABL+6
000404   71001201   71040575              FSU VTABL+3
000405   72001310   72040703              FMP MPAR
000406   32001602   32041174              STA ZFLUOR

C ADD DIFF. TO RINF FOR Z FILTER WITHOUT FLUOR. TO GET Z WITH FLUOR.

ZRINF=RITABL(3)+ZFLUOR
000407   00002031   00041422              LDA RITABL+3
000410   70001602   70041172              FAD ZFLUOR
000411   32001603   32041172              STA ZRINF

C CALC. TRI STIM. XSUBB REFLECTANCE WITH FLUORECENCE BY ADDING
                                    C EMPIRICAL FRACT OF CHANGE IN Z REFL INPUTS DUE TO FLUOR

XBRINF=RITABL(1)+ZFLUOR*MPAR(1)
000412   00001602   00041170              LDA ZFLUOR
000413   72001311   72040676              FMP MPAR+1
000414   70002027   70041413              FAD RITABL+1

C CALC. TAPPI OPACITY

TOPAC=RZTABL(5)/YAR89
000442   00002013   00041351              LDA RZTABL+5
000443   73001237   73040574              FDV YAR89
000444   32001240   32040574              STA TOPAC

C CALC. TRI-STIM X WITH XSUBB INCLUDING FLUOR.

XTRI=.196*XBRINF+.784*RITABL(2)
000445   00001545   00041100              LDA $FLCON+3
000446   72001604   72041136              FMP XBRINF 000447   32001555   32041106              STA $TEMP
000450   00001546   00041076              LDA $FLCON+4
000451   72002030   72041357              FMP RITABL+2
000452   70001555   70041103              FAD $TEMP
000453   32001241   32040566              STA XTRI

C CALC. TRI-STIM Y WITH ILLUM. C

YTRI=RITABL(4)
000454   00002032   00041356              LDA RITABL+4
000455   32001242   32040565              STA YTRI 000415   32001604   32041167              STA XBRINF

C CALC BRIGHTNESS FILTER REFLECTANCE WITH FLUOR. BY ADDING
                                    C EMPIRICAL FRACT OF CHANGEIN Z REFL INPUTS DUE T FLUOR.

BRRINF=RITABL(0)+ZFLUOR*MPAR(2)
000416   00001602   00041164              LDA ZFLUOR
000417   72001312   72040673              FMP MPAR+2
000420   70002026   70041406              FAD RITABL
000421   32001247   32040626              STA BRRINF

C CALC. PRINTING OPACITY AS RATIO OF RZERO/RINF FOR YSUBC FILTER.

POPAC=RZTABL(4)/RITABL(4)
000422   00002012   00041370              LDA RZTABL+4
000423   73002032   73041407              FDV RITABL+4
000424   32001236   32040612              STA POPAC

C CALC. TRI-STIM Y REFL. WITH ILLUM. A + .89 BACKING.

YAR89=RZTABL(5)+(.89*TTABL(5)*TTABL(5))
                                          1/(1.-.89*RZTABL(5))
000425   00001544   00041117              LDA $FLCON+2
000426   72002013   72041365              FMP RZTABL+5
000427   71001542   71041113              FSU $FLCON
000430   32001555   32041125              STA $TEMP
000431   00001544   00041113              LDA $FLCON+2
000432   72002023   72041371              FMP TTABL+5
000433   72002023   72041370              FMP TTABL+5
000434   73001555   73041121              FDV $TEMP
000435   71002013   71041356              FSU RZTABL+5
000436   05004670   05004670              TZE
000437   34000441   34040002              BTS *+2
000440   05047027   05047027              CBK_23
000441   32001237   32040576              STA YAR89
```

```
                                    C CALC. TRI-STIM Z WITH FLUOR.                              7
                                          ZTRI=1.18*ZRINF                                       7
000456   00001547   00041071              LDA $FLCON+5                                          1
000457   72001603   72041124              FMP ZRINF                                             1
000460   32001243   32040563              STA ZTRI                                              1

C CALC. HUNTER L COORD.                                     7
                                          LH=100.0*SQRTF(YTRI)                                  7
000461   00001242   00040561              LDA YTRI                                              1
000462   33002037   33041355              SPB SQRTF                                             1
000463   32001555   32041072              STA $TEMP                                             1
000464   00001550   00041064              LDA $FLCON+6                                          1
000465   72001555   72041070              FMP $TEMP                                             1
000466   32001244   32040556              STA LH                                                1

C CALC. HUNTER SMALL A                                      7
                                          AH=175.*(1.02*XTRI-YTRI)/LH                           7
000467   00001552   00041063              LDA $FLCON+8                                          1
000470   72001241   72040551              FMP XTRI                                              1
000471   71001242   71040551              FSU YTRI                                              1
000472   72001551   72041057              FMP $FLCON+7                                          1
000473   73001244   73040551              FDV LH                                                1
000474   32001245   32040551              STA AH                                                1

C CALC. HUNTER SMALL B                                      7
                                          BH=70.*(YTRI-.847*ZTRI)/LH                            7
000475   00001554   00041057              LDA $FLCON+10                                         1
000476   72001243   72040545              FMP ZTRI                                              1
000477   71001242   71040543              FSU YTRI                                              1
000500   72001553   72041053              FMP $FLCON+9                                          1
000501   73001244   73040543              FDV LH                                                1
000502   05004670   05004670              TZE                                                   1
000503   34000505   34040002              BTS *+2                                               1
000504   05047027   05047027              CBK 23                                                1

000505   32001246   32040541              STA BH                                                1

C RESET FILTER CYCLE SLOWDOWN INDEX TO INITIAL VALUE IN MPAR<3   7
                                    CAND STORE IN PERM. CORE FILE AT /63200<10 BASE 10          7
                                          FILEX(10)=MPAR(3)                                     7
000506   00001313   00040605              LDA MPAR+3                                            1
000507   32001114   32040405              STA FILEX+10                                          1
                                          CONTINUE                                              7
000510   16301526   16341016              LDX FILADD,3           SAVE WORKING CYCLE COUNT IN PERM CORE  6
000511   00001114   00040403              LDA FILEX1+10                                         6
000512   32300012   32300012              STA 10,3                                              6

PRINT 600,(RZTABL(M),M=0,7)                           7
000513   40000756   40040243              LDK $600                                              1
000514   45004330   45004330              MAQ                                                   1
000515   33000561   33000561              SPB $PRINT                                            1
000516   00001527   00041011              LDA $FXCON                                            1
000517   32001605   32041066              STA M                                                 1
000520   16601605   16641065       $M1    LDX M,6                                               1
000521   40602006   40641265              LDK RZTABL,6                                          1
000522   32001555   32041033              STA $TEMP                                             1
000523   33000563   33000563              SPB $OUTRP                                            1
000524   16701555   16741031              LDX $TEMP,7                                           1
000525   05003000   05003000              LDO 0                                                 1
000526   11001605   11041057              ADD M                                                 1
000527   32001605   32041056              STA M                                                 1
000530   31001540   31041010              SUB $FXCON+9                                          1
000531   05004670   05004670              TZE                                                   1
000532   05004527   05004527              SOD 23                                                1
000533   34000520   34077765              BTS $M1                                               1
000534   33000564   33000564              SPB $HLOUT                                            1

PRINT 600,(TTABL(M),M=0,7)                            7
000535   40000756   40040221              LDK $600                                              1
000536   45004330   45004330              MAQ                                                   1
000537   33000561   33000561              SPB $PRINT                                            1
000540   00001527   00040767              LDA $FXCON                                            1
000541   32001605   32041044              STA M                                                 1
000542   16301605   16341043       $M2    LDX M,3                                               1
000543   40302016   40341253              LDK TTABL,3                                           1
000544   32001555   32041011              STA $TEMP                                             1
000545   33000563   33000563              SPB $OUTRP                                            1
000546   16701555   16741007              LDX $TEMP,7                                           1
000547   05003000   05003000              LDO 0                                                 1
000550   11001605   11041035              ADD M                                                 1
000551   32001605   32041034              STA M                                                 1
000552   31001540   31040766              SUB $FXCON+9                                          1

000553   05004670   05004670              TZE                                                   1
000554   05004527   05004527              SOD 23                                                1
000555   34000542   34077765              BTS $M2                                               1
000556   33000564   33000564              SPB $HLOUT                                            1

PRINT 600,(RITABL(M),M=0,7)                           7
000557   40000756   40040177              LDK $600                                              1
000560   45004330   45004330              MAQ                                                   1
000561   33000561   33000561              SPB $PRINT                                            1
```

| | | | | | |
|---|---|---|---|---|---|
| 000562 | 00001527 | 00040745 | | LDA $FXCON | 1 |
| 000563 | 32001605 | 32041022 | | STA M | 1 |
| 000564 | 16401605 | 16441021 | $M3 | LDX M,4 | 1 |
| 000565 | 40402026 | 40441241 | | LDK RITABL,4 | 1 |
| 000566 | 32001555 | 32040767 | | STA $TEMP | 1 |
| 000567 | 33000563 | 33000563 | | SPB $OUTRP | 1 |
| 000570 | 16701555 | 16740765 | | LDX $TEMP,7 | 1 |
| 000571 | 05003000 | 05003000 | | LDO 0 | 1 |
| 000572 | 11001605 | 11041013 | | ADD M | 1 |
| 000573 | 32001605 | 32041012 | | STA M | 1 |
| 000574 | 31001540 | 31040744 | | SUB $FXCON+9 | 1 |
| 000575 | 05004670 | 05004670 | | TZE | 1 |
| 000576 | 05004527 | 05004527 | | SOD 23 | 1 |
| 000577 | 34000564 | 34077765 | | BTS $M3 | 1 |
| 000600 | 33000564 | 33000564 | | SPB $HLOUT | 1 |
| | | | | PRINT 600,(STABL(M),M=0,7) | 7 |
| 000601 | 40000756 | 40040155 | | LDK $600 | 1 |
| 000602 | 45004330 | 45004330 | | MAQ | 1 |
| 000603 | 33000561 | 33000561 | | SPB $PRINT | 1 |
| 000604 | 00001527 | 00040723 | | LDA $FXCON | 1 |
| 000605 | 32001605 | 32041000 | | STA M | 1 |
| 000606 | 16501605 | 16540777 | $M4 | LDX M,5 | 1 |
| 000607 | 40501250 | 40540441 | | LDK STABL,5 | 1 |
| 000610 | 32001555 | 32040745 | | STA $TEMP | 1 |
| 000611 | 33000563 | 33000563 | | SPB $OUTRP | 1 |
| 000612 | 16701555 | 16740743 | | LDX $TEMP,7 | 1 |
| 000613 | 05003000 | 05003000 | | LDO 0 | 1 |
| 000614 | 11001605 | 11040771 | | ADD M | 1 |
| 000615 | 32001605 | 32040770 | | STA M | 1 |
| 000616 | 31001540 | 31040722 | | SUB $FXCON+9 | 1 |
| 000617 | 05004670 | 05004670 | | TZE | 1 |
| 000620 | 05004527 | 05004527 | | SOD 23 | 1 |
| 000621 | 34000606 | 34077765 | | BTS $M4 | 1 |
| 000622 | 33000564 | 33000564 | | SPB $HLOUT | 1 |
| | | | | PRINT 600,(KTABL(M),M=0,7) | 7 |
| 000623 | 40000756 | 40040133 | | LDK $600 | 1 |
| 000624 | 45004330 | 45004330 | | MAQ | 1 |
| 000625 | 33000561 | 33000561 | | SPB $PRINT | 1 |
| 000626 | 00001527 | 00040701 | | LDA $FXCON | 1 |
| 000627 | 32001605 | 32040756 | | STA M | 1 |
| 000630 | 16601605 | 16640755 | $M5 | LDX M,6 | 1 |
| 000631 | 40601260 | 40640427 | | LDK KTABL,6 | 1 |
| 000632 | 32001555 | 32040723 | | STA $TEMP | 1 |
| 000633 | 33000563 | 33000563 | | SPB $OUTRP | 1 |
| 000634 | 16701555 | 16740721 | | LDX $TEMP,7 | 1 |
| 000635 | 05003000 | 05003000 | | LDO 0 | 1 |
| 000636 | 11001605 | 11040747 | | ADD M | 1 |
| 000637 | 32001605 | 32040746 | | STA M | 1 |
| 000640 | 31001540 | 31040700 | | SUB $FXCON+9 | 1 |
| 000641 | 05004670 | 05004670 | | TZE | 1 |
| 000642 | 05004527 | 05004527 | | SOD 23 | 1 |
| 000643 | 34000630 | 34077765 | | BTS $M5 | 1 |
| 000644 | 33000564 | 33000564 | | SPB $HLOUT | 1 |
| | | | | PRINT 600,(STTABL(M,0),M=0,7) | 7 |
| 000645 | 40000756 | 40040111 | | LDK $600 | 1 |
| 000646 | 45004330 | 45004330 | | MAQ | 1 |
| 000647 | 33000561 | 33000561 | | SPB $PRINT | 1 |
| 000650 | 00001527 | 00040657 | | LDA $FXCON | 1 |
| 000651 | 32001605 | 32040734 | | STA M | 1 |
| 000652 | 16301605 | 16340733 | $M6 | LDX M,3 | 1 |
| 000653 | 40301136 | 40340263 | | LDK STTABL,3 | 1 |
| 000654 | 32001555 | 32040701 | | STA $TEMP | 1 |
| 000655 | 33000563 | 33000563 | | SPB $OUTRP | 1 |
| 000656 | 16701555 | 16740677 | | LDX $TEMP,7 | 1 |
| 000657 | 05003000 | 05003000 | | LDO 0 | 1 |
| 000660 | 11001605 | 11040725 | | ADD M | 1 |
| 000661 | 32001605 | 32040724 | | STA M | 1 |
| 000662 | 31001540 | 31040656 | | SUB $FXCON+9 | 1 |
| 000663 | 05004670 | 05004670 | | TZE | 1 |
| 000664 | 05004527 | 05004527 | | SOD 23 | 1 |
| 000665 | 34000652 | 34077765 | | BTS $M6 | 1 |
| 000666 | 33000564 | 33000564 | | SPB $HLOUT | 1 |
| | | | | PRINT 600,(STTABL(M,1),M=0,7) | 7 |
| 000667 | 40000756 | 40040067 | | LDK $600 | 1 |
| 000670 | 45004330 | 45004330 | | MAQ | 1 |
| 000671 | 33000561 | 33000561 | | SPB $PRINT | 1 |
| 000672 | 00001527 | 00040635 | | LDA $FXCON | 1 |
| 000673 | 32001605 | 32040712 | | STA M | 1 |
| 000674 | 16401605 | 16440711 | $M7 | LDX M,4 | 1 |
| 000675 | 40401146 | 40440251 | | LDK STTABL+8,4 | 1 |
| 000676 | 32001555 | 32040657 | | STA $TEMP | 1 |
| 000677 | 33000563 | 33000563 | | SPB $OUTRP | 1 |
| 000700 | 16701555 | 16740655 | | LDX $TEMP,7 | 1 |
| 000701 | 05003000 | 05003000 | | LDO 0 | 1 |
| 000702 | 11001605 | 11040703 | | ADD M | 1 |
| 000703 | 32001605 | 32040702 | | STA M | 1 |
| 000704 | 31001540 | 31040634 | | SUB $FXCON+9 | 1 |
| 000705 | 05004670 | 05004670 | | TZE | 1 |
| 000706 | 05004527 | 05004527 | | SOD 23 | 1 |
| 000707 | 34000674 | 34077765 | | BTS $M7 | 1 |
| 000710 | 33000564 | 33000564 | | SPB $HLOUT | 1 |
| | | | | PRINT 600,(RGTABL(M,0),M=0,7) | 7 |

```
000711  40000756  40040045           LDK  $600                        1
000712  45004330  45004330           MAQ                               1
000713  33000561  33000561           SPB  $PRINT                       1
000714  00001527  00040613           LDA  $FXCON                       1
000715  32001605  32040670           STA  M                            1
000716  16501605  16540667     $M8   LDX  M,5                          1
000717  40501156  40540237           LDK  RGTABL,5                     1
000720  32001555  32040635           STA  $TEMP                        1
000721  33000563  33000563           SPB  $OUTRP                       1
000722  16701555  16740633           LDX  $TEMP,7                      1
000723  05003000  05003000           LDO  0                            1
000724  11001605  11040661           ADD  M                            1
000725  32001605  32040660           STA  M                            1
000726  31001540  31040612           SUB  $FXCON+9                     1
000727  05004670  05004670           TZE                               1
000730  05004527  05004527           SOD  23                           1
000731  34000716  34077765           BTS  $M8                          1
000732  33000564  33000564           SPB  $HLOUT                       1

PRINT 600,(RGTABL(M,1),M=0,7)    7
000733  40000756  40040023           LDK  $600                         1
000734  45004330  45004330           MAQ                               1
000735  33000561  33000561           SPB  $PRINT                       1
000736  00001527  00040571           LDA  $FXCON                       1
000737  32001605  32040646           STA  M                            1
000740  16601605  16640645     $M9   LDX  M,6                          1
000741  40601166  40640225           LDK  RGTABL+8,6                   1
000742  32001555  32040613           STA  $TEMP                        1
000743  33000563  33000563           SPB  $OUTRP                       1
000744  16701555  16740611           LDX  $TEMP,7                      1
000745  05003000  05003000           LDO  0                            1
000746  11001605  11040637           ADD  M                            1
000747  32001605  32040636           STA  M                            1
000750  31001540  31040570           SUB  $FXCON+9                     1
000751  05004670  05004670           TZE                               1
000752  05004527  05004527           SOD  23                           1
000753  34000740  34077765           BTS  $M9                          1
000754  33000564  33000564           SPB  $HLOUT                       1

600  FORMAT(8F10.5)                   7
000755  14000760  14040003           BRU  $M10                         1
000756  02470056  02470056     $600  CON  0,02470056                   1
000757  60077776  60077776           CON  0,60077776                   1

PRINT 600,(VTABL(M,0),M=0,7)     7
000760  40000756  40077776    $M10   LDK  $600                         1
000761  45004330  45004330           MAQ                               1
000762  33000561  33000561           SPB  $PRINT                       1
000763  00001527  00040544           LDA  $FXCON                       1
000764  32001605  32040621           STA  M                            1
000765  16301605  16340620    $M11   LDX  M,3                          1
000766  40301176  40340210           LDK  VTABL,3                      1
000767  32001555  32040566           STA  $TEMP                        1
000770  33000563  33000563           SPB  $OUTRP                       1
000771  16701555  16740564           LDX  $TEMP,7                      1
000772  05003000  05003000           LDO  0                            1
000773  11001605  11040612           ADD  M                            1
000774  32001605  32040611           STA  M                            1
000775  31001540  31040543           SUB  $FXCON+9                     1
000776  05004670  05004670           TZE                               1
000777  05004527  05004527           SOD  23                           1
001000  34000765  34077765           BTS  $M11                         1
001001  33000564  33000564           SPB  $HLOUT                       1

PRINT 600,(VTABL(M,1),M=0,7)     7
001002  40000756  40077754           LDK  $600                         1
001003  45004330  45004330           MAQ                               1
001004  33000561  33000561           SPB  $PRINT                       1
001005  00001527  00040522           LDA  $FXCON                       1
001006  32001605  32040577           STA  M                            1
001007  16401605  16440576    $M12   LDX  M,4                          1
001010  40401206  40440176           LDK  VTABL+8,4                    1
001011  32001555  32040544           STA  $TEMP                        1
001012  33000563  33000563           SPB  $OUTRP                       1
001013  16701555  16740542           LDX  $TEMP,7                      1
001014  05003000  05003000           LDO  0                            1
001015  11001605  11040570           ADD  M                            1
001016  32001605  32040567           STA  M                            1
001017  31001540  31040521           SUB  $FXCON+9                     1
001020  05004670  05004670           TZE                               1
001021  05004527  05004527           SOD  23                           1
001022  34001007  34077765           BTS  $M12                         1
001023  33000564  33000564           SPB  $HLOUT                       1

PRINT 700,(MPAR(M),M=0,6)        7
001024  40001047  40040023           LDK  $700                         1
001025  45004330  45004330           MAQ                               1
001026  33000561  33000561           SPB  $PRINT                       1
001027  00001527  00040500           LDA  $FXCON                       1
001030  32001605  32040555           STA  M                            1
001031  16501605  16540554    $M13   LDX  M,5                          1
001032  40501310  40540256           LDK  MPAR,5                       1
001033  32001555  32040522           STA  $TEMP                        1
001034  33000563  33000563           SPB  $OUTRP                       1

001035  16701555  16740520           LDX  $TEMP,7                      1
001036  05003000  05003000           LDO  0                            1
001037  11001605  11040546           ADD  M                            1
```

```
001040  32001605  32040545        STA M                                    1
001041  31001533  31040472        SUB $FXCON+4                             1
001042  05004670  05004670        TZE                                      1
001043  05004527  05004527        SOD 23                                   1
001044  34001031  34077765        BTS $M13                                 1
001045  33000564  33000564        SPB $HLOUT                               1

700   FORMAT(3F10.5,I10,3F10.5)                7
001046  14001053  14040005        BRU $M14                                 1
001047  02420056  02420056  $700  CON 0,02420056                           1
001050  22401602  22401602        CON 0,22401602                           1
001051  02420056  02420056        CON 0,02420056                           1
001052  60077774  60077774        CON 0,60077774                           1

PRINT 500,(OUTABL(M),M=0,9)              7
001053  40001076  40040023  $M14  LDK $500                                 1
001054  45004330  45004330        MAQ                                      1
001055  33000561  33000561        SPB $PRINT                               1
001056  00001527  00040451        LDA $FXCON                               1
001057  32001605  32040526        STA M                                    1
001060  16601605  16640525  $M15  LDX M,6                                  1
001061  40601236  40640155        LDK OUTABL,6                             1
001062  32001555  32040473        STA $TEMP                                1
001063  33000563  33000563        SPB $OUTRP                               1
001064  16701555  16740471        LDX $TEMP,7                              1
001065  05003000  05003000        LDO 0                                    1
001066  11001605  11040517        ADD M                                    1
001067  32001605  32040516        STA M                                    1
001070  31001541  31040451        SUB $FXCON+10                            1
001071  05004670  05004670        TZE                                      1
001072  05004527  05004527        SOD 23                                   1
001073  34001060  34077765        BTS $M15                                 1
001074  33000564  33000564        SPB $HLOUT                               1

500   FORMAT(10F10.5)                          7
001075  14001100  14040003        BRU $M16                                 1
001076  02510056  02510056  $500  CON 0,02510056                           1
001077  60077776  60077776        CON 0,60077776                           1

120   CONTINUE                                 7
001100  300000000 300000000 $M16  BSS 0                                    1
001100  300000000 300000000 $120  BSS 0                                    1

C TURN PROG. 42 OFF. WILL BE TURNED ON BY PROG. 14   7
                                  STOP                                     7
001100  33000405  33000405        SPB OFFC02                               1

001101  10000000  10000000        PRG 0,1,0,0,0                            1
001102  300000014 300000014       FILEX1 BSS 12                            6
001116  300000020 300000020       CTABL1 BSS 16                            6
001136  300000020 300000020       STTAB1 BSS 16                            6
001156  300000020 300000020       RGTAB1 BSS 16                            6
001176  300000020 300000020       VTABL1 BSS 16                            6
001216  300000020 300000020       SGTAB1 BSS 16                            6
001236  300000012 300000012       OUTAB1 BSS 10                            6
001250  300000010 300000010       STABL1 BSS 8                             6
001260  300000010 300000010       KTABL1 BSS 8                             6
001270  300000020 300000020       RSTAB1 BSS 16                            6
001310  300000020 300000020       MPAR1  BSS 16                            6
001330  00070632  00070632        BWPFA CON 0,70632                        6
001331  00073261  00073261        MOD   CON 0,73261                        6
                                  CON   EQL *                              6
001332  300000174 300000174       BSS 124                                  6
001526  00063200  00063200        FILADD CON 0,63200                       6

DEFINE CTABL(CTABL1),FILEX(FILEX1)       7
                                  CTABL EQL CTABL1                         1
                                  FILEX EQL FILEX1                         1

DEFINE STTABL(STTAB1),RGTABL(RGTAB1)     7

1,VTABL(VTABL1),SGTABL(SGTAB1),OUTABL(OUTAB1),STABL(STABL1),  7
                                  2KTABL(KTABL1),RSTABL(RSTAB1)            7
                                  STTABL EQL STTAB1                        1
                                  RGTABL EQL RGTAB1                        1
                                  VTABL  EQL VTABL1                        1
                                  SGTABL EQL SGTAB1                        1
                                  OUTABL EQL OUTAB1                        1
                                  STABL  EQL STABL1                        1
                                  KTABL  EQL KTABL1                        1
                                  RSTABL EQL RSTAB1                        1

DEFINE MPAR(MPAR1)                       7
                                  MPAR  EQL MPAR1                          1

END                                      7
001527  300000000 300000000       BSS 0                                    1
001527  00000000  00000000  $FXCON CON 0,00000000                          1
001530  00000001  00000001        CON 0,00000001                           1
001531  00000010  00000010        CON 0,00000010                           1
001532  00000002  00000002        CON 0,00000002                           1
001533  00000006  00000006        CON 0,00000006                           1
001534  00000003  00000003        CON 0,00000003                           1
001535  00000004  00000004        CON 0,00000004                           1
001536  00000005  00000005        CON 0,00000005                           1
001537  00000012  00000012        CON 0,00000012                           1
```

```
001540   00000007    00000007                 CON  0,00000007                                          1
001541   00000011    00000011                 CON  0,00000011                                          1
001542   20600000    20600000     $FLCON      CON  0,20600000                                          1
001543   21200000    21200000                 CON  0,21200000                                          1
001544   20343656    20343656                 CON  0,20343656                                          1
001545   17310550    17310550                 CON  0,17310550                                          1
001546   20310550    20310550                 CON  0,20310550                                          1
001547   20627024    20627024                 CON  0,20627024                                          1
001550   23710000    23710000                 CON  0,23710000                                          1
001551   24257000    24257000                 CON  0,24257000                                          1
001552   20602437    20602437                 CON  0,20602437                                          1
001553   23614000    23614000                 CON  0,23614000                                          1
001554   20330652    20330652                 CON  0,20330652                                          1
001555   300000000   300000000    $STBRU      BSS  0                                                   1
001555   300000003   300000003    $TEMP       BSS  3                                                   1
                                  POPAC       EQL  OUTABL                                              1
                                  YAR89       EQL  OUTABL+1                                            1
                                  CYCLE       EQL  FILEX+10                                            1
                                  BW          EQL  MPAR+4                                              1
                                  TOPAC       EQL  OUTABL+2                                            1
                                  XTRI        EQL  OUTABL+3                                            1
                                  YTRI        EQL  OUTABL+4                                            1
                                  ZTRI        EQL  OUTABL+5                                            1
                                  LH          EQL  OUTABL+6                                            1
                                  AH          EQL  OUTABL+7                                            1
                                  BH          EQL  OUTABL+8                                            1
                                  BRRINF      EQL  OUTABL+9                                            1
001560   300000001   300000001    NX          BSS  1                                                   1
001561   300000001   300000001    IRR         BSS  1                                                   1
001562   300000001   300000001    J           BSS  1                                                   1
001563   300000001   300000001    I           BSS  1                                                   1
001564   300000001   300000001    SGCF        BSS  1                                                   1
001565   300000001   300000001    TD          BSS  1                                                   1
001566   300000001   300000001    TDP         BSS  1                                                   1
001567   300000001   300000001    RG          BSS  1                                                   1
001570   300000001   300000001    R           BSS  1                                                   1
001571   300000001   300000001    RZERO       BSS  1                                                   1
001572   300000001   300000001    T           BSS  1                                                   1
001573   300000001   300000001    AI          BSS  1                                                   1
001574   300000001   300000001    BI          BSS  1                                                   1
001575   300000001   300000001    RINF        BSS  1                                                   1
001576   300000001   300000001    AX          BSS  1                                                   1
001577   300000001   300000001    LNAX        BSS  1                                                   1
001600   300000001   300000001    S           BSS  1                                                   1
001601   300000001   300000001    K           BSS  1                                                   1
001602   300000001   300000001    ZFLUOR      BSS  1                                                   1
001603   300000001   300000001    ZRINF       BSS  1                                                   1
001604   300000001   300000001    XBRINF      BSS  1                                                   1
001605   300000001   300000001    H           BSS  1                                                   1
001606   300000200   300000200    TMPSAV      BSS  128                                                 1

002006   300000010   300000010    RZTABL      BSS  8                                                   1
002016   300000010   300000010    TTABL       BSS  8                                                   1
002026   300000010   300000010    RITABL      BSS  8                                                   1
002036   926054130   926054130    XXXEXP      LIB                                                      1
         921254120   921254120                                                                         1
002037   924650522   924650522    SQRTF       LIB                                                      1
         925043040   925043040                                                                         1
002040   923047507   923047507    LOGF        LIB                                                      1
         921420040   921420040                                                                         1

*PROGRAM END.   0 FORTRAN ERRORS                         1
         *00000000   *00000000                END                                                      1
                                                              0 ASSEMBLY ERRORS.
                                                        002342 PROGRAM OCTAL SIZE.
                                                        000470 EQL TABLE OCTAL SIZE.
```

PROPOSED OPTICAL CONTROL STRATEGY

While the on-line automatic control of paper optical properties is an ultimate objective of the work reported herein, the claimed subject matter relates to on-machine monitoring of paper optical properties whether used as an aid to conventional manual control or for other purposes. Nevertheless, in order to provide a disclosure of the best mode presently contemplated for automatic control as a separate but related area of endeavor, the following discussion is presented.

The optical properties of a sheet of paper are dependent upon all of the materials of which it is made but primarily upon the furnished pulp, fillers, pigments, dyes, and some additives. If is often very difficult to maintain the optical attributes of the pulp, fillers and additives constant within a given production run. Such variation is even greater between runs. The optical properties of the finished paper may, however, be reasonably controlled to specified standards by varying the additions of dyes and fillers and pigments until the desired compensations are achieved. The problem is that each furnished ingredient affects each of the resulting paper optical properties in a rather complicated manner. Indeed the intuition of experienced papermakers has essentially been the sole method of optical property control. Unfortunately, this approach is inefficient, resulting in consideable off-standard paper and/or waste of costly materials. Accordingly, a dire need exists within the paper industry for a highly reliable and continuous optical property monitor coupled with a closed loop computer control system.

The value of such closed loop control, based on a feedback color detector, has already been demonstrated for the continuous addition of two and sometimes three dyes. (1) (2) Target dye concentrations changes of up to three dyes can be determined by solving three simultaneous equations containing three unknowns. (1) One disadvantage of such control is that accurate color monitoring is not presently available unless large and fresix percent (56%). With the illustrated embodiment, once the system is properly adjusted with respect to the zero reflectance readings (as by the use of a black sheet of known minimal reflectance) the system maintains such zero adjustment quite stably; accordingly the higher the reflectance value of the optical window, the more effective is the reflectance standardization by means of the optical window. On the other hand a transmittance value which is of a reasonable magnitude is also desirable, so that the provision of an optical window with substantial values of absolute reflectance and transmittance is advantageous.

With the illustrated embodiment, the transmittance readings for the moving web are relatively more nearly independent of misalignment of the upper and lower sensing heads than the reflectance readings. Further it is considered that tilting of the lower sensing head relative to the optical axis of the upper sensing head has less effect on transmittance readings than on reflectance readings. Thus it is considered that it would be advantageous to have an optical window such as 135 with an absolute reflectance value of seventy percent (70%) or more. A value of reflectance as high as ninety percent (90%) would not be unreasonable and would generally still permit a transmittance value of a subtantial magnitude to give reasonably comparable accuracy of reflectance and transmittance readings for on-line operation as herein described.

While separate photometric sensing means for the reflectance and transmittance readings have been shown, it is possible with the use of fiber optics, for example, to use a common photometric sensor and alternately supply light energy from the reflectance and transmittance light paths thereto, providing the response time of the sensor enables reflectance and transmittance readings to be obtained for essentially the same region of the moving web. Generally the possibility of such time multiplexing of reflectance and transmittance readings will depend on the speed of movement of the web and the degree of uniformity of sheet formation and the like.

It is very desirable that the system of the present invention be applicable to sheet materials having a wide range of characteristics such as basis weight and sheet formation, and operable at high speeds of movement such as 100 to 3000 feet per minute. Further, for maximum accuracy, it is necessary that a region of the sheet material being sampled have substantially uniform opacity. Accordingly, especially for sheet material of relatively low basis weight and relatively poor sheet formation, greater accuracy can be expected when the response of the photometric sensor is relatively fast, and when reflectance and transmittance readings are taken simultaneously and are a measure of the characteristics of a common sampling region of minimum area (consistent with adequate signal to noise ratios). Thus multiplexing of reflectance and transmittance readings is not preferred for the case of high speed paper machinery and comparable environments, nor is it desirable to use reflectance and transmittance light paths which intersect the web at spacially offset regions.

With respect to speed of response of the photometric sensing means substantial improvements over the previously described components are deemed presently available. If the spectral response and other necessary characteristics are suitable, a sensor with such a higher speed of response is preferred for the illustrated embodiment. Good experience has been had with a silicon photocell presently considered as having an appropriate spectral response characteristics for color and other measurements in accordance with the present invention. The specific silicon cell referred to is identified as a Schottky Planar Diffuse Silicon Pin 10 DP photodiode of a standard series supplied by United Detector Technology Incorporated, Santa Monica, Ca.

In place of a rotatable filter wheel arrangement as shown in FIGS. 3 and 4, a set of twelve fiber optic light paths may define six simultaneously operative reflectance light paths in upper sensing head 11 and six simultaneously operative transmittance light paths in lower sensing head 12. The six reflectance fiber optic paths would include respective filters corresponding to filters 281–286 and respective individual photocells and would be located to receive respective portions of the reflected light which is reflected generally along path 137 in FIG. 3. The six transmittance fiber optic paths would also include respective filters corresponding to filters 281–286 and respective individual photocells, and would be located to receive respective portions of the transmitted light which is transmitted generally along paths such as 141–143 in FIG. 3. The filter means in the incident light path such as indicated at 133 in FIG. 3 might include a filter in series with filters 271 and 272 for filtering out the ultraviolet component from the incident beam, so that the twelve simultaneous photocell readings corresponding to those designated RSD1 through RSD6, and TSD1 through TSD6 (when the device is off-sheet), and corresponding to those designated RSP1 through RSP6, and TSP1 through TSP6 (when the device is on-sheet) will exclude a fluorescent contribution. (See Table 3 where this notation is introduced.)

If a reflectance reading corresponding to RSD7 (when the device is off-sheet) and corresponding to RSP7 (when the device is on-sheet) is desired so as to enable computation of fluorescent contribution to brightness, it would be necessary to mechanically remove the ultraviolet filter from the incident light path, or otherwise introduce an ultraviolet component of proper magnitude, and obtain another brightness (Z) reading, for example from the number four reflectance photocell.

As an alternative to the above fiber optic system with a common incident light path, seven fiber optical tubes incorporating filters corresponding to 281–287 of FIGS. 3 and 4, respectively, at say the light exit points of the tubes, could be used to supply the incident light to seven different points on the paper web. The reflected light from each of these seven points could be monitored by seven different systems, each involving lenses and a photocell, and the number seven reflected light path including also a filter corresponding to filter 288, FIG. 4. The transmitted light from the first six points would also need to be kept separately, and this could be accomplished by six integrating cavities and six photocells.

As a further alternative the seven fiber optical tubes defining the seven incident light paths could have a second set of seven fiber optical tubes and photocells respectively disposed to receive reflected light from the respective illuminated points. Another set of six fiber optical tubes and photocells could be associated with the first six illuminated points for receiving transmitted light. This could eliminate the need for the light collecting lenses in the upper sensing head and the integrating cavities in the lower sensing head.

quent empirically determined correction factors are applied to the original output results. A second disadvantage arises when opacity and the fluorescence must also be simultaneously controlled. In this case the number of independently controlled continuous additions increases from three to five. An optical brightener and an opacifying pigment constitute the two additional factors.

An object of this invention is to demonstrate a method by which fluorescence can be continuously monitored. A means by which the optical brightener addition can be separately and independently controlled is inherently implied. The paper color is also analyzed without the fluorescent contribution. It is, of course, this latter characterization (without fluorescence) which should be, but which has not in the past been, used to determine the required addition of the conventional dyes. In other words, the effect of the optical brightener is decoupled from the three conventional dyes making possible the simultaneous control of all four dyes.

Another portion of this invention demonstrates a means of continuously determining the scattering coefficient of the moving web for each of the six available light spectrums. It is possible to determine the scattering coefficient required to achieve a given opacity specification whenever the basis weight and absorption coefficient are known. When the latter are set equal to a given set of product specifications, then the calculated scattering coefficient becomes the target scattering coefficient. (The absorption coefficient can be acquired by off-line testing of a sample of the standard color to be matched. In reality, this becomes a target absorption coefficient as well.) The dyes have little, if any, effect on the scattering coefficient but the effect of the slurry pigment is very large. Thus the target scattering coefficient is used as the sole feedback variable to control the slurry pigment feed. This will insure that the opacity is at or near the specification as long, as the absorption coefficient and basis weight are also on target. The absorption coefficient should, of course, be on target by virtue of the independent color control. A completely independent system controls the basis weight.

A method by which the decoupling of three conventional dyes, one optical brightener and one opacifying pigment has hereby been explained. Heretofore, such decoupling as revealed in the prior art has been limited to three absorptive dyes and thereby neglecting the need to also achieve a specified degree of fluorescence and opacity.

References

1. The development of dynamic color control on a paper machine by H. Chao and W. Wickstrom; Automatica, Vol. 6 PP 5–18, Pergamon Press, 1970.
2. Another consideration for color and formation by Henry H. Chao and Warren A. Wickstrom, color engineering, September/October 1971.

DISCUSSION OF THE CLAIM TERMINOLOGY AND SCOPE

The present invention is for the purpose of obtaining a quantitative measure of an optical property such as brightness, color, opacity or fluorescence of single thickness sheet material.

The sheet material is substantially homogeneous in its thickness dimension such that the optical property of interest can be reliably calculated from reflectance and transmittance measurements on the basis of existing theory. Thus the present invention is not applicable to the sensing of localized surface effects (such as due to surface migration of light absorbing powder particles, for example). To the contrary the present invention is concerned with the average or bulk optical characteristics of the sheet material considered as a whole, and especially is concerned with the characteristics of paper sheet material as it is delivered from a paper machine after completion of the paper manufacturing process.

The present invention in its broader aspect does not require strictly homogeneous material since empirical correction factors can be applied for cases where theory is less effective. For example, the paper optical properties of calendered and coated papers may be effectively measured by the system of the present invention using grade correction factors to correlate on-machine results with the measurements obtained by standard off-line instruments.

The optical system of the monitoring device includes components such as those shown in FIG. 3 which define or optically affect the incident, reflected and transmitted light paths such as indicated at 133, 137 and 141–143 in FIG. 3. For the case of a filter wheel as indicated in FIG. 4, each filter wheel position may be considered to define a separate light energy path with its own predetermined spectral response characteristics.

In each filter wheel position, there are two distinct light energy paths for measuring a reflectance value and a transmittance value, respectively. In the illustrated embodiment each such light energy path includes a common incident light path 133, but the paths diverge, one coinciding with the reflectance sensing light path 137 and the other including the transmittance sensing light path. The photometric sensors 203 and 260 thus provide simultaneous reflectance and transmittance output signals with respect to essentially a common region of the web. The reflectance sensing light path collects light from a circular region with a diameter of about 3/16 inch, and the transmittance sensing light path collects light from a total elliptical region which includes substantially the same circular region as mentioned above. Because of sheet formation effects and other localized variations in web characteristics it is considered valuable that the reflectance and transmittance output signals are based on readings from essentially a common region of the web.

By taking at least one reading in each traverse of the web, and taking such readings at different points along the width in successive traverses, it is considered that accuracies equal to or superior to those of an off-line sampling of a finished reel can be achieved, while at the same time the readings are available immediately instead of after completion of a manufacturing run.

By way of example, in the illustrated system a traversal of the web by the sensing head takes about forty-five seconds, so that the sensing head operates at a rate of at least one traversal of the width of the web per minute in the time intervals between the hourly off-sheet standardizing operations.

In accordance with the teachings of an improvement to the present invention, the optical window 135 is itself selected as to its optical characteristics so as to provide the basis for off-sheet standardization. To this end it is advantageous that the optical window exhibit an absolute reflectance value as measured by the standard automatic color-brightness tester of at least about thirty-five percent (35%). The corresponding absolute transmittance value as measured on the G.E. Recording Spectrophotometer with conventional optics is about fifty- The last two mentioned alternatives with seven fiber optical tubes defining the incident light paths appear to be rather complicated systems, but they do offer means of eliminating both the mechanical filter wheel as well as any mechanical device to control the presence of ultraviolet light in the incident beam.

Still another alternative is to use "screens" in addition to the filters in the embodiment of FIGS. 1–5. The new photodiodes are considered sensitive enough to measure reduced light intensites so that screens with different transmittance values could be used with six of the incident beam filters so that the net photocell output for each reflectance light path, and for each transmittance light path, would be similar enough so that separate and individual pre-amplification for the respective reflectance outputs would not be necessary, and so that separate and individual pre-amplification for each transmittance output would not be necessary. This means that reed switches 341–347 and 351–357, and relays $K_1$ through $K_7$ in FIG. 6 could be eliminated, and that the feedback paths for amplifiers 361 and 429 could have the same resistance value in each filter wheel position. A means of sensing filter wheel position would still be necessary, but this could be done in a number of simple ways, one of which would be a single reed switch such as reed switch 358 shown in FIG. 6. The number of necessary conductors in the cables 51 and 52, FIG. 5, would, of course, be reduced in this modification.

The term "screen" is understood in the art as referring to a network of completely opaque regions and intervening openings or completely translucent regions, such that light energy is uniformly attenuated over the entire spectrum by an amount dependent on the proportion of opaque to transmitting area.

The device of FIGS. 1 and 2 has been tested on a machine operating at about 1000 feet per minute, and no problems have appeared in maintaining the necessary uniform and stable contact geometry between the head and the moving web.

It will be apparent that many further modifications and variations may be effected without departing from the scope of the novel concepts of the present invention.

DESCRIPTION OF FIGS. 21 AND 22

An instrument 1010 is shown in FIG. 21 made up of two scanning sensing heads 1011 and 1012, one above and one below the moving paper web 14, and a dedicated computer with appropriate couplers for input and output forms part of digital computer system 1996, FIG. 22. The bottom head 1012 receives light transmitted through the sheet and subsequently analyzed for its X, Y, and Z tristimulus components. It also contains a backing 1135 of some specified effective reflectance (for example a black body of zero, or near zero, reflectance) located just ahead or behind (machine direction) relative to entrance 1154 of the transmitted light receptor compartment indicated at 1145-T, FIG. 22.

The upper head 1011 contains light source means 1201 as well as a reflected light receptor indicated at 1145-R, FIG. 22. The latter receives light energy after reflection from the moving web at a point just above the backing 1135, on the bottom head 1012 and the reflected light energy would also be analyzed for its X, Y, and Z tristimulus components. Both light receivers 1145-R and 1145-T and, for that matter, the light source means 1201 itself may be integrating cavities of a type. This would be one way to insure the uniform distribution of emitted, transmitted, and reflected light in the X-direction in addition to providing identical samples of light going to each photoelectric cell installed with filters within the cavities themselves, this arrangement being represented in FIG. 22. The flux of the light source means 1201 could be monitored or controlled by a third partial, or full, set of filter-photocell combinations. The availability of both the transmitted (T) and reflected ($R_g$) light signals described above and as indicated in FIGS. 21 and 22 allows for precise computation of the reflectance with an infinite backing ($R_{oo}$). It is the latter, $R_{oo}$ value, which is required to characterize color, brightness, and an index of fluorescence. In addition, it would eliminate the need for any grade corrections in measuring either printing or TAPPI opacity, both of which could be made available if desired.

A small, rather low-cost, dedicated computer such as that forming part of system 1996 with appropriate interface equipment such as indicated at 1997 could be used to receive all signals, compute all pertinent optical properties, and determine the signal for direct, closed loop control of:

a. 2–5 separate conventional dye additions;
 b. fluorescent dye feed to the size press; and
 c. PKT, $TiO_2$, or other slurry flow;

so that brightness, opacity, color (L, a,b) and fluorescene could be maintained almost exactly as chosen by, perhaps even a master computer, if desired.

Kubelka-Munk equations, quantitative color descriptions, and their inter-relationships, recently acquired wet end mathematical models, along with existing control theory, are all presently available in some form or other to convert the input signals from the scanning heads 1011 and 1012 to optical measurements and flow feeds with which paper manufacturers are familiar. The combined mathematical technology above is also sufficient for adequate decoupling of this otherwise complicated information so that overlapped control is avoided.

Use of a dedicated computer would eliminate most of the electronics now associated with optical measuring equipment. It could also be used to integrate results across the web and simplify and/or maintain calibration. The package would lend itself to rather universal application and minimize the time and effort on the part of the purchaser.

The key feature of the instrument 1010 which distinguishes it from existing on-line optical testers, is that it provides for the measurement of both transmitted and reflected light without undue complications. This, in turn, can cause a great deal of improvements regarding sensitivity, accuracy, flexibility, and thoroughness of a continuous optical property measuring device.

DESCRIPTION OF FIGS. 23 and 24

FIGS. 23 and 24 show further means by which the incorporated patent applications can be employed without the use of a mechanically operated filter wheel.

In FIG. 23, an ultra violet light absorbing filter is located at 2271, and the U.V. filtered incident light beam 2133 is directed to impinge upon the moving web 14.

Transmitted light is collected within the integrating cavity 2145-T below the web, just as in the embodiment of FIGS. 1–6. The resulting intensity and color of this light is analyzed in a manner comparable to such embodiment by employing, for example, six separate ports containing six different filter-photocell combinations including filters such as 2281-T, 2282-T and 2283-T (and as shown in FIG. 22) representing Brightness, $X_R$, $X_B$, Z, $Y_C$, and $Y_A$, respectively. The output of each photocell could be read continuously or intermittently by means of a computer equipped with appropriate interface electronics as in the previous embodiments.

The reflected light component is directed through an appropriate lens system 2273 into a second integrating cavity 2145-R located above the moving web. Its intensity and color is, likewise, analyzed by the use of six filter-photocell combinations including filters such as 2281-R, 2282-R and 2283-R (and as shown in FIG. 22) and connected eventually to the same computer.

FIG. 24 is similar to FIG. 23 except that fiber optics (light conveying tubes) are utilized in place of the integrating cavities. A representative portion of the transmitted light is directed into each of six such tubes (five of the tubes being indicated at 3001-3005 in FIG. 24) which are ended by means of specific spectral response filters (Br, $X_R$, $X_B$, Z, $Y_C$, $Y_A$,) and corresponding photocells, five of the filter-photocell combinations being indicated at 3011-3015. The same is done for the reflected light by means of filter-photocell combinations five being indicated at 3021-3025. All twelve outputs of this example are again read either continuously or intermittently by a computer.

The fluorescent component of light resulting from the use of "optical brightners" is not included in any of the above measurements. It can be measured, of course, by mechanically removing the U.V. incident beam filter and synchronizing such change with a status change to the computer. A short time later the U.V. filter is reinstated back into position. A rotating U.V. filter-chopper could be employed at 3271 providing proper synchronization of the computer data storage is also accomplished.

The set of twelve fiber optic light paths as shown in FIG. 24 may define six simultaneously operative reflectance light paths in upper sensing head 3011 and six simultaneously operative transmittance light paths in lower sensing head 3012. The six reflectance fiber optic paths include respective filters corresponding to filters 281-286 and respective individual photocells located to receive respective portions of the reflected light which is reflected generally along a path such as that indicated at 137 in FIG. 3. The six transmittance fiber optic paths would also include respective filters corresponding to filters 281-286 and respective individual photocells located to receive respective portions of the transmitted light which is transmitted generally along paths corresponding to paths 141-143 in FIG. 3. The filter means in the incident light path includes a filter 3271 similar to filters 271 and 272 for filtering out the ultraviolet component from the incident beam, so that the twelve simultaneous photocell readings corresponding to those designated RSD1 through RSD6, and TSD1 through TSD6 (when the device is off-sheet), and corresponding to those designated RSP1 through RSP6, and TSP1 through TSP6 (when the device is on-sheet) will exclude a fluorescent contribution. (See Table 3 where this notation is introduced.).

If a reflectance reading corresponding to RSD7 (when the device is off-sheet) and corresponding to RSP7 (when the device is on-sheet) is desired so as to enable computation of fluorescent contribution to brightness, it is necessary to mechanically remove the ultraviolet filter 3271 from the incident light path, or otherwise introduce an ultraviolet component of proper magnitude, and obtain another brightness (Z) reading, for example from the number four reflectance photocell.

As an alternative to the above filter optic system with a common incident light path as shown in FIG. 24, seven fiber optical tubes incorporating filters corresponding to 281-287 of FIGS. 3 and 4, respectively, at say the light exit points of the tubes, could be used to supply the incident light to seven different points on the paper web. The reflected light from each of these seven points could be monitored by seven different systems, each involving lenses and a photocell such as shown in FIG. 24, and the number seven reflected light path including also a filter corresponding to filter 288, FIG. 4. The transmitted light from the first six points would also need to be kept separately, and this could be accomplished by six integrating cavities and six photocells.

As a further alternative the seven fiber optical tubes defining the seven incident light paths could have a second set of seven filter optical tubes and photocells respectively disposed to receive reflected light from the respective illuminated points as in FIG. 24. Another set of six fiber optical tubes and photocells could be associated with the first six illuminated points for receiving transmitted light as in FIG. 24. This could eliminate the need for the light collecting lenses in the upper sensing head and the integrating cavities in the lower sensing head.

The last two mentioned alternatives with seven fiber optical tubes defining the incident light paths appear to be rather complicated systems, but they do offer means of eliminating both the mechanical filter wheel as well as any mechanical device to control the presence of ultraviolet light in the incident beam.

Still another alternative is to use "screens" in addition to the filters in the embodiments of FIGS. 21-24. The new photodiodes are considered sensitive enough to measure reduced light intensities so that screens with different transmittance values could be used with six of the incident beam filters or with the reflectance and transmittance filters so that the net photocell output for each reflectance light path, and for each transmittance light path, would be similar enough so that separate and individual pre-amplification for the respective reflectance outputs would not be necessary, and so that separate and individual preamplification for each transmittance output would not be necessary. This means that the feedback paths for the twelve amplifiers of components 1361-R and 1361-T in FIG. 22, for example, could have the same resistance values.

The term "screen" is understood in the art as referring to a network of completely opaque regions and intervening openings or completely translucent regions, such that light energy is uniformly attenuated over the entire spectrum by an amount dependent on the proportion of opaque to transmitting area.

I claim as my invention:

1. A method of measuring Tappi opacity comprising the steps of:

(a) calibrating a transmittance measurement (TSP6) to obtain a calibrated transmittance value (TPD/TD) which is a measure of the transmittance of light having a spectral distribution for characterizing Tappi opacity, (b) separately calibrating a reflectance measurement (RSP6) to obtain a calibrated reflectance value (RPD6) which is a measure of the reflectance of light having a spectral distribution for characterizing Tappi opacity, (c) calculating a transmittance value (T) based on the calibrated transmittance value (TPD/TD) and the calibrated reflectance value (RPD6) such that the calculated transmittance value (T) corresponds to the absolute transmittance as measured on a scale from zero to one hundred, (d) calculating a reflectance value ($R_o$) based on the calibrated reflectance value (RPD6) and the calibrated transmittance value (TPD/TD) such that the calculated reflectance value ($R_o$) corresponds to the absolute reflectance as measured on a scale from zero to one hundred, and (e) calculating a value for Tappi opacity ($R_o/R.89$) based both on said calculated transmittance value (T) and on said calculated reflectance value ($R_o$) utilizing a nonlinear mathematical relationship between Tappi opacity and the absolute transmittance and absolute reflectance values, (f) arranging a light source on one side of a moving web of paper sheet material, (g) directing light from the light source along a common incident light path so as to impinge on said one side of said moving web, and so as to provide wavelengths of light incident on the moving web having a spectral distribution for characterizing Tappi opacity, (h) arranging transmitted light and reflected light detectors on the respective opposite sides of the moving web to receive light of said spectral distribution from the light source after passage along said common incident light path and respectively after being transmitted through said moving web and respectively after being reflected from said one side of said moving web, thereby to obtain from a common region of the moving web a transmittance signal from the transmitted light detector and a reflectance signal from the reflected light detector, and (i) separately transmitting the transmittance and reflectance signals to provide a transmittance measurement (TSP6) and a reflectance measurement (RSP6) and separately converting said measurements to digital form for processing at least according to the foregoing steps (a) through (e).

2. A method according to claim 1 further comprising backing the moving web on the side of the moving web opposite said one side of the moving web at a region aligned with the common incident light path, and processing at least the reflectance measurement (RSP6) to take account of the reflectance of said backing (RD6).

3. A method of measuring printing opacity comprising the steps of:

(a) calibrating a transmittance measurement (TSP5) to obtain a calibrated transmittance value (TPD/TD) which is a measure of the transmittance of light having a spectral distribution for characterizing printing opacity, (b) separately calibrating a reflectance measurement (RSP5) to obtain a calibrated reflectance value (RPD5) which is a measure of the reflectance of light having a spectral distribution for characterizing printing opacity, (c) calculating a transmittance value (T) based on the calibrated transmittance value (TPD/TD) and the calibrated reflectance value (RPD5) such that the calculated transmittance value (T) corresponds to the absolute transmittance as measured on a scale from zero to one hundred, (d) calculating a reflectance value ($R_o$) based on the calibrated reflectance value (RPD5) and the calibrated transmittance value (TPD/TD) such that the calculated reflectance value ($R_o$) corresponds to the absolute reflectance as measured on a scale from zero to one hundred, and (e) calculating a value for printing opacity ($R_o/R_{oo}$) based both on said calculated transmittance value (T) and on said calculated reflectance value ($R_o$) utilizing a nonlinear mathematical relationship between printing opacity and the absolute transmittance and absolute reflectance values, (f) arranging a light source on one side of a moving web of paper sheet material, (g) directing light from the light source along a common incident light path so as to impinge on said one side of said moving web, and so as to provide wavelengths of light incident on the moving web having a spectral distribution for characterizing printing opacity, (h) arranging transmitted light and reflected light detectors on the respective opposite sides of the moving web to receive light of said spectral distribution from the light source after passage along said common incident light path and respectively after being transmitted through said moving web and respectively after being reflected from said one side of said moving web, thereby to obtain from a common region of the moving web a transmittance signal from the transmitted light detector and a reflectance signal from the reflected light detector, and (i) separately transmitting the transmittance and reflectance signals to provide a transmittance measurement (TSP5) and a reflectance measurement (RSP5) and separately converting said measurements to digital form for processing at least according to the foregoing steps (a) through (e).

4. A method according to claim 3 further comprising backing the moving web on the side of the moving web opposite said one side of the moving web at a region aligned with the common incident light path, and processing at least the reflectance measurement (RSP5) to take account of the reflectance (RD5) of said backing.

* * * * *